(12) United States Patent
Bohm et al.

(10) Patent No.: US 11,638,543 B2
(45) Date of Patent: May 2, 2023

(54) ANALYTE SENSOR ELECTRODE ARRANGEMENTS

(71) Applicant: DexCom, Inc., San Diego, CA (US)

(72) Inventors: Sebastian Bohm, San Diego, CA (US); Wenjie Lan, Westford, MA (US); Thomas Robert Porter, San Diego, CA (US); Daiting Rong, San Diego, CA (US); Jason Halac, Solana Beach, CA (US)

(73) Assignee: Dexcom, Inc., San Diego, CA (US)

( * ) Notice: Subject to any disclaimer, the term of this patent is extended or adjusted under 35 U.S.C. 154(b) by 180 days.

(21) Appl. No.: 16/929,906

(22) Filed: Jul. 15, 2020

(65) Prior Publication Data

US 2021/0015407 A1    Jan. 21, 2021

Related U.S. Application Data

(60) Provisional application No. 62/874,842, filed on Jul. 16, 2019.

(51) Int. Cl.
*A61B 5/1468* (2006.01)
*A61B 5/145* (2006.01)
*C09D 133/08* (2006.01)

(52) U.S. Cl.
CPC ........ *A61B 5/14532* (2013.01); *A61B 5/1468* (2013.01); *A61B 2562/125* (2013.01); *C09D 133/08* (2013.01)

(58) Field of Classification Search
None
See application file for complete search history.

(56) References Cited

U.S. PATENT DOCUMENTS

| 6,001,067 A | 12/1999 | Shults et al. |
| 6,424,847 B1 | 7/2002 | Mastrototaro et al. |
| 6,464,848 B1 * | 10/2002 | Matsumoto .......... G01N 27/301 |
| | | 204/290.01 |
| 6,477,395 B2 | 11/2002 | Schulman et al. |
| 6,484,046 B1 | 11/2002 | Say et al. |
| 6,512,939 B1 | 1/2003 | Colvin et al. |
| 6,565,509 B1 | 5/2003 | Say et al. |
| 6,579,690 B1 | 6/2003 | Bonnecaze et al. |
| 7,494,465 B2 | 2/2009 | Brister et al. |
| 7,799,191 B2 | 9/2010 | Yu et al. |
| 8,682,608 B2 | 3/2014 | Tsuzuki et al. |
| 9,044,199 B2 | 6/2015 | Brister et al. |
| 2005/0027463 A1 | 2/2005 | Goode et al. |

(Continued)

FOREIGN PATENT DOCUMENTS

DE    19533059 A1    3/1997

OTHER PUBLICATIONS

International Search Report and Written Opinion for Application No. PCT/US2020/042175 dated Oct. 14, 2020, 12 pages.

*Primary Examiner* — Meredith Weare
(74) *Attorney, Agent, or Firm* — Schwegman Lundberg & Woessner, P.A.

(57) ABSTRACT

Various examples are directed to a glucose sensor comprising a working electrode to support an oxidation reaction and a reference electrode to support a redox reaction. The reference electrode may comprise silver and silver chloride. The Glucose sensor may also comprise an anti-mineralization agent positioned at the reference electrode to reduce formation of calcium carbonate at the reference electrode.

20 Claims, 26 Drawing Sheets

(56) References Cited

U.S. PATENT DOCUMENTS

| | | |
|---|---|---|
| 2006/0020187 A1 | 1/2006 | Brister et al. |
| 2007/0027385 A1 | 2/2007 | Brister et al. |
| 2007/0197890 A1 | 8/2007 | Boock et al. |
| 2007/0235331 A1* | 10/2007 | Simpson .............. A61B 5/1473 |
| | | 204/403.01 |
| 2008/0108942 A1 | 5/2008 | Brister et al. |
| 2008/0119703 A1 | 5/2008 | Brister et al. |
| 2010/0108509 A1* | 5/2010 | Curry .................... C12Q 1/002 |
| | | 204/403.14 |
| 2010/0236923 A1* | 9/2010 | Oviatt, Jr. .............. C12Q 1/001 |
| | | 204/403.14 |
| 2012/0186999 A1* | 7/2012 | Walton ................ G01N 33/497 |
| | | 977/773 |
| 2012/0262298 A1 | 10/2012 | Böhm et al. |
| 2014/0262775 A1 | 9/2014 | Papadimitrakopoulos et al. |
| 2018/0328877 A1* | 11/2018 | Vaddiraju .......... G01N 27/3277 |
| 2019/0120785 A1 | 4/2019 | Halac et al. |

\* cited by examiner

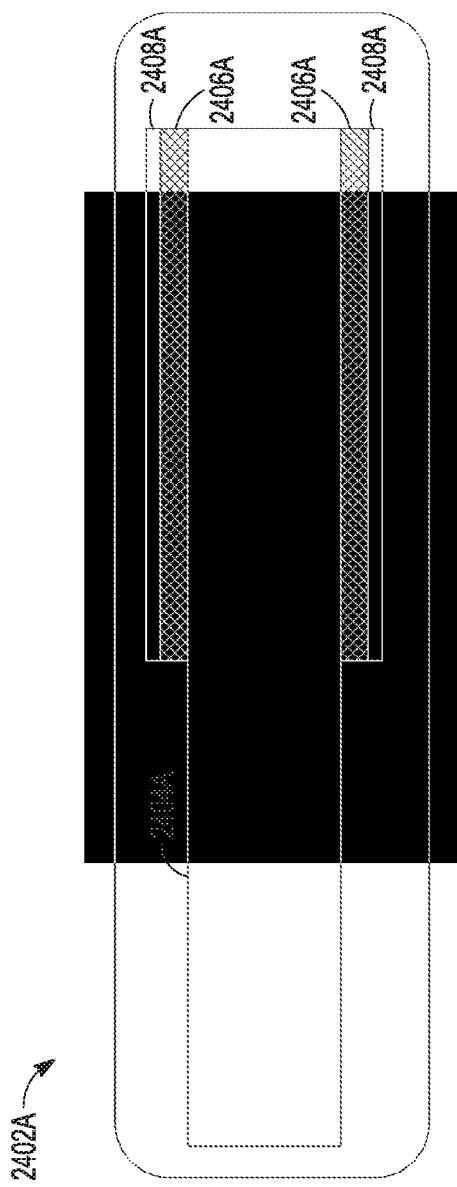
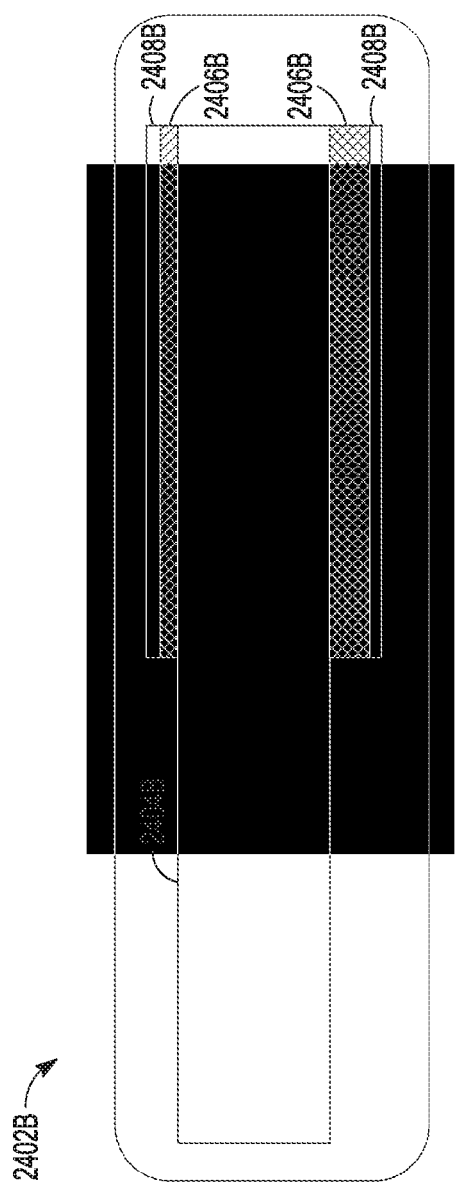
FIG. 24A
FIG. 24B

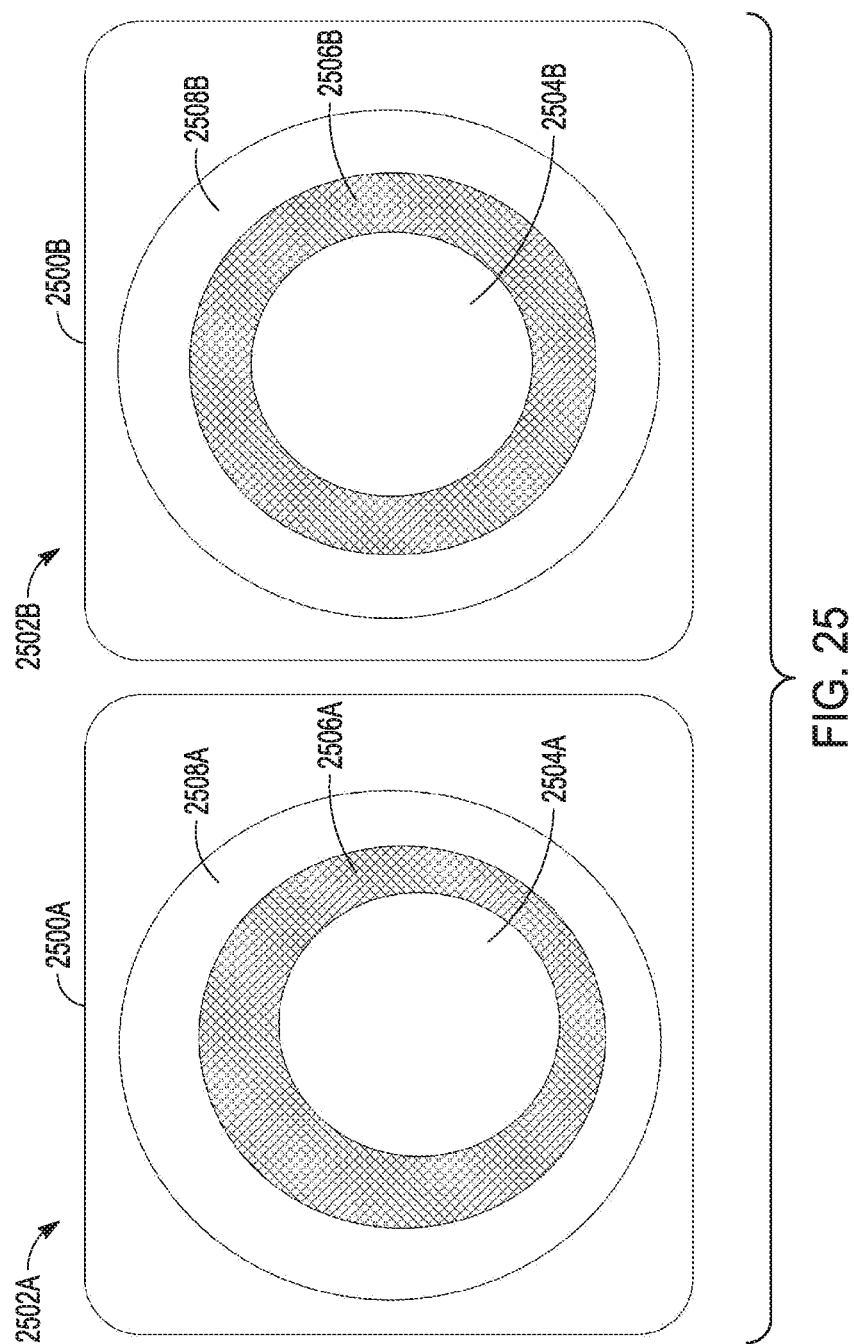

ANALYTE SENSOR ELECTRODE ARRANGEMENTS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application Ser. No. 62/874,842 filed on Jul. 16, 2019. The aforementioned application is incorporated by reference herein in its entirety, and is hereby expressly made a part of this specification.

TECHNICAL FIELD

The present development relates generally to medical devices such as analyte sensors, and more particularly, but not by way of limitation, to systems, devices, and methods that mitigate degradation in analyte sensor performance due to changes in the reference (e.g., counter-reference) electrode.

BACKGROUND

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels. A glucose sensor can provide an estimated glucose concentration level, which can be used as guidance by a patient or caregiver.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Blood sugar concentration levels may be monitored with an analyte sensor, such as a continuous glucose monitor. A continuous glucose monitor may provide the wearer (patient) with information, such as an estimated blood glucose level or a trend of estimated blood glucose levels.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

This present application discloses, among other things, systems, devices, and methods for mitigating break-in in an analyte sensor, such as a glucose sensor.

Example 1 is a glucose sensor comprising: a working electrode to support an oxidation reaction; and a reference electrode to support a redox reaction, the reference electrode comprising: silver; silver chloride; and a mediator material to catalyze oxygen redox at the reference electrode at least in part with the silver.

In Example 2, the subject matter of Example 1 includes the mediator material comprising a quinone derivative.

In Example 3, the subject matter of Example 2 includes, 2-ethyl-anthroquinone.

In Example 4, the subject matter of Example 3 further includes the quinone derivative configured to undergo an electrolytic cycle comprising: a first reaction including the quinone to generate 2-ethyl-anthroquinol, the first reaction occurring when an operating potential at the reference electrode is below a threshold potential; a second reaction including the 2-ethyl-anthroquinol and oxygen to regenerate the quinone; and a third reaction including at least one product of the second reaction to regenerate silver chloride.

In Example 5, the subject matter of Example 4 includes the threshold potential being between about 0.020 volts and about 0.155 volts.

In Example 6, the subject matter of Examples 1-5 includes the mediator material comprising a quinone derivative selected from the group consisting of biquinone, 1-napthaquinone, 4-napthaquinone.

In Example 7, the subject matter of Examples 1-6 includes the mediator material being selected from the group consisting of a transition metal porphyrins, a nitroxyl species, and a hydrazine.

In Example 8, the subject matter of Examples 1-7 includes the reference electrode configured to support silver chloride redox at a first operating potential and oxygen redox at a second operating potential and the second operating potential being within about 0.05 volts of the first operating potential.

In Example 9, the subject matter of Examples 1-8 includes the silver comprising microscale silver particles having an average width of between about 1 micron and about 10 microns and nanoscale silver particles having an average size that is less than 100 nanometers, wherein the nanoscale silver particles make up between about 0.1% and about 10% of the silver by volume.

Example 10 is a glucose sensor comprising: a working electrode to support an oxidation reaction; and a reference electrode to support a redox reaction, the reference electrode comprising: a binder material; silver chloride particles incorporated into the binder material; and silver particles incorporated into the binder material, the silver particles comprising a mixture of microscale silver particles and nanoscale silver particles, wherein the nanoscale silver particles have an average size that is less 100 nanometers and microscale silver particles having an average width of between about 1 micron and about 10 microns.

In Example 11, the subject matter of Example 10 includes, the nanoscale silver particles making up between about 0.1% and about 10% of the silver particles by volume.

In Example 12, the subject matter of Examples 10-11 includes the reference electrode further comprising a mediator material.

In Example 13, the subject matter of Example 12 includes the mediator material comprising a quinone derivative.

In Example 14, the subject matter of Examples 10-13 includes the reference electrode further comprising a transition metal in contact with at least a portion of the silver particles.

In Example 15, the subject matter of Example 14 includes the transition metal being selected from the group consisting of zinc, aluminum, manganese, magnesium, titanium, and copper.

In Example 16, the subject matter of Examples 10-15 includes the reference electrode further comprising platinum incorporated into the binder material to catalyze oxygen redox at the reference electrode.

In Example 17, the subject matter of Examples 10-16 includes an anti-mineralization agent positioned at the reference electrode to reduce formation of calcium carbonate at the reference electrode.

In Example 18, the subject matter of Examples 10-17 includes, a membrane system, the membrane system comprising: a resistance domain positioned at least in part over the reference electrode; and a hydrophilic domain positioned at least in part over the reference electrode.

Example 19 is a glucose sensor comprising: a working electrode to support an oxidation reaction; and a reference electrode to support a redox reaction, the reference electrode comprising: silver chloride; and silver; and a transition metal in contact with the silver.

In Example 20, the subject matter of Example 19 includes the transition metal being selected from the group consisting of zinc, aluminum, manganese, magnesium, titanium, and copper.

In Example 21, the subject matter of Example 20 includes at least a portion of the silver and at least a portion of the transition metal comprising silver/transition metal particles.

Example 22 is a glucose sensor comprising: a working electrode to support an oxidation reaction; and a reference electrode to support a redox reaction, the reference electrode comprising: a binder material; silver particles incorporated into the binder material; silver chloride particles incorporated into the binder material; and platinum incorporated into the binder material to catalyze oxygen redox at the reference electrode.

In Example 23, the subject matter of Example 22 includes the platinum comprising platinum particles incorporated into the binder material.

In Example 24, the subject matter of Example 23 includes an average size of the platinum particles being about equal to an average size of the silver particles and about equal to an average size of the silver chloride particles.

In Example 25, the subject matter of Examples 23-24 includes an average size of the platinum particles being between about 0.4 microns and about 5 microns.

In Example 26, the subject matter of Example 25 includes an average size of the platinum particles being between about 0.8 microns and about 2.5 microns. microns.

In Example 27, the subject matter of Examples 23-26 includes an average size of the platinum particles being between about 50 nanometers and about 200 nanometers.

In Example 28, the subject matter of Examples 22-27 includes the platinum being between about 1% of a metal volume added to the binder material and about 20% of the metal volume added to the binder material and the metal volume including a sum of a volume of the silver particles, a volume of silver chloride particles, and a volume of platinum.

In Example 29, the subject matter of Examples 22-28 includes the platinum comprising platinum deposits positioned on at least one of a set of surfaces of the silver particles or a set of surfaces of the silver chloride particles.

In Example 30, the subject matter of Example 29 includes an average diameter of the platinum deposits being between about 50 nanometers and about 200 nanometers.

In Example 31, the subject matter of Example 30 includes the average diameter of the platinum deposits is about 100 nanometers.

In Example 32, the subject matter of Examples 22-31 includes an anti-mineralization agent.

In Example 33, the subject matter of Example 32 includes the anti-mineralization agent comprising at least one of a polyacrylate or a carboxylate-containing polymer.

In Example 34, the subject matter of Examples 22-33 includes the silver particles comprising: microscale silver particles having an average width of between about 1 micron and about 10 microns; and nanoscale silver particles having an average size that is less than 100 nanometers, wherein the nanoscale silver particles make up between about 0.1% and about 10% of the silver particles by volume.

Example 35 is a glucose sensor comprising: a working electrode to support an oxidation reaction; and a reference electrode to support a redox reaction, the reference electrode comprising: silver; and silver chloride; and an anti-mineralization agent positioned at the reference electrode to reduce formation of calcium carbonate at the reference electrode.

In Example 36, the subject matter of Example 35 includes, the reference electrode further comprising platinum.

In Example 37, the subject matter of Examples 35-36 includes the anti-mineralization agent selected from the group consisting of a polyacrylate and a carboxylate-containing polymer.

In Example 38, the subject matter of Examples 35-37 includes, a membrane system comprising an anti-mineralization layer positioned at least in part over the reference electrode, the anti-mineralization layer comprising at least a portion of the anti-mineralization agent.

In Example 39, the subject matter of Example 38 includes the membrane system further comprising an interference domain positioned at least in part over the working electrode, the interference domain comprising a first interference agent and at least a portion of the anti-mineralization agent.

In Example 40, the subject matter of Examples 35-39 includes the reference electrode comprising a binder material and the silver, silver chloride, and the anti-mineralization agent being positioned within the binder material.

In Example 41, the subject matter of Examples 35-40 includes the anti-mineralization agent comprising a polyacrylate.

In Example 42, the subject matter of Examples 35-41 includes the anti-mineralization agent comprising a carboxylate-containing polymer.

In Example 43, the subject matter of Example 42 includes the carboxylate-containing polymer being selected from the group consisting of a poly(maleate), a polysulfonate, or a polyphosphonate.

In Example 44, the subject matter of Examples 35-43 includes the silver comprising microscale silver particles having an average width of between about 1 micron and about 10 microns, the nanoscale silver particles having an average size that is less than 100 nanometers and the nanoscale silver particles making up between about 0.1% and about 10% of the silver by volume.

Example 45 is a method for treating a glucose sensor comprising a working electrode and a silver/silver-chloride reference electrode positioned proximally from the working electrode, the method comprising: dipping a distal end of the glucose sensor into a first solution to a first depth from the distal end, the first solution comprising a first agent, wherein at the first depth, the first solution covers the working electrode; and dipping the distal end of the glucose sensor into a second solution to a second depth from the distal end, the second solution comprising an anti-mineralization agent, and the second depth covering the working electrode and at least a portion of the reference electrode, wherein the first agent and the anti-mineralization agent form an interference domain over the working electrode.

In Example 46, the subject matter of Example 45 includes the dipping of the distal end of the glucose sensor into the second solution being after the dipping of the distal end of the glucose sensor into the first solution, and further comprising, after dipping the distal end of the glucose sensor into the second solution, re-dipping the distal end of the glucose sensor into the first solution to the first depth.

In Example 47, the subject matter of Examples 45-46 includes the dipping of the distal end of the glucose sensor into the first solution being after the dipping of the distal end of the glucose sensor into the second solution, and further comprising, after dipping the distal end of the glucose sensor into the first solution, re-dipping the distal end of the glucose sensor into the second solution to the second depth.

In Example 48, the subject matter of Examples 45-47 includes dipping the distal end of the glucose sensor into a third solution comprising glucose oxidase.

In Example 49, the subject matter of Examples 45-48 includes the anti-mineralization agent comprising a polyacrylate.

In Example 50, the subject matter of Examples 45-49 includes the anti-mineralization agent comprises a carboxylate-containing polymer.

In Example 51, the subject matter of Example 50 includes, wherein the carboxylate-containing polymer is selected from the group consisting of a poly(maleate), a polysulfonate, a polyphosphonate.

Example 52 is a method for operating a glucose sensor comprising a working electrode and a silver/silver-chloride reference electrode, the method comprising: applying a first current between the working electrode and the reference electrode; and after applying the first current, generating a sensor current with the glucose sensor, a magnitude of the sensor current indicating glucose concentration at the glucose sensor, the first current being larger than the sensor current.

In Example 53, the subject matter of Example 52 includes a current density of the reference electrode at the first current being more than about five times larger than a current density of the reference electrode at the sensor current.

In Example 54, the subject matter of Examples 52-53 includes, before generating the sensor current, immersing at least the reference electrode in a solution of chlorine bleach.

Example 55 is a method for operating a glucose sensor comprising a working electrode and a silver/silver-chloride reference electrode, the method comprising: immersing at least the reference electrode in a solution of chlorine bleach; and after the immersing, generating a sensor current with the glucose sensor, a magnitude of the sensor current indicating glucose concentration at the glucose sensor.

In Example 56, the subject matter of Example 55 includes the immersing being maintained for about two minutes.

In Example 57, the subject matter of Examples 55-56 includes the solution of chlorine bleach being between about 5% chlorine bleach and 100% chlorine bleach.

In Example 58, the subject matter of Examples 55-57 includes the solution of chlorine bleach being about 10% chlorine bleach.

In Example 59, the subject matter of Examples 55-58 includes, before generating the sensor current, applying a first current between the working electrode and the reference electrode.

In Example 60, the subject matter of Example 59 includes a current density of the reference electrode at the first current being more than about five times larger than a current density of the reference electrode at the sensor current.

Example 61 is a glucose sensor comprising: a working electrode to support an oxidation reaction; and a reference electrode to support a redox reaction, the reference electrode comprising: silver; and silver chloride; a membrane system comprising: a resistance domain positioned at least in part over the reference electrode; and a hydrophilic domain positioned at least in part over the reference electrode.

In Example 62, the subject matter of Example 61 includes the resistance domain being positioned between the reference electrode and the hydrophilic domain.

In Example 63, the subject matter of Examples 61-62 includes the hydrophilic domain being positioned between the reference electrode and the resistance domain.

In Example 64, the subject matter of Examples 61-63 includes the hydrophilic domain being between about 2 microns and about 5 microns.

In Example 65, the subject matter of Examples 61-64 includes, the hydrophilic domain comprising an oxidase.

In Example 66, the subject matter of Example 65 includes the hydrophilic domain comprising glucose oxidase and the glucose oxidase also covering at least a portion of the working electrode.

In Example 67, the subject matter of Examples 61-66 includes the hydrophilic domain comprising a hydrophilic polymer.

In Example 68, the subject matter of Examples 61-67 includes the hydrophilic domain comprising a polyelectrolyte.

Example 69 is at least one machine-readable medium including instructions that, when executed by processing circuitry, cause the processing circuitry to perform operations to implement of any of Examples 1-68.

Example 70 is an apparatus comprising means to implement of any of Examples 1-68.

Example 71 is a system to implement of any of Examples 1-68.

Example 72 is a method to implement of any of Examples 1-68.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments described in the present document.

FIGS. 24A and 24B show in-line X-ray images showing example analyte sensors.

FIG. 25 shows cross-sectional X-ray images showing example analyte sensors.

DETAILED DESCRIPTION

Various examples described herein are directed to analyte sensors and methods for using analyte sensors. An analyte sensor is placed in contact with bodily fluid of a host to measure a concentration of an analyte, such as glucose, in the bodily fluid. In some examples, the analyte sensor is inserted under the skin of the host and placed in contact with interstitial fluid below the skin to measure the concentration of the analyte in the interstitial fluid.

When the analyte sensor is exposed to analyte, an electrochemical reaction between the analyte sensor and the analyte causes the analyte sensor to generate a raw sensor signal indicating the analyte concentration. In some examples, the analyte sensor includes a working electrode and a reference electrode. In a three electrode configuration, the analyte sensor also includes a counter electrode. In the presence of analyte, the electrochemical reaction causes a current to flow between the working electrode and the counter electrode, where the raw sensor signal is or is based on the current. In the three-electrode configuration, the reference electrode provides a stable reference potential and conducts very little current.

In two-electrode configurations, the counter electrode is omitted. The electrochemical reaction between the analyte sensor and the analyte causes a current between the working electrode and the reference electrode. Accordingly, the reference electrode both conducts a current, like the counter electrode in the three-electrode configuration and provides a stable reference potential, like the reference electrode in the three-electrode configuration. Accordingly, the reference electrode in a two-electrode configuration is sometimes referred to as a counter-reference electrode. Herein, the term reference electrode may refer to the reference electrode of a three-electrode configuration, the counter-reference electrode of a two-electrode configuration, or similar electrodes in other configurations.

In use, sensor electronics apply a bias potential between the working electrode and the reference (e.g., counter-reference) electrode. The applied bias promotes the electrochemical reaction between the analyte and the analyte sensor, resulting in a current between the working electrode and the reference (e.g., counter-reference) electrode. The current makes up all or part of the raw sensor signal.

Figure 1:
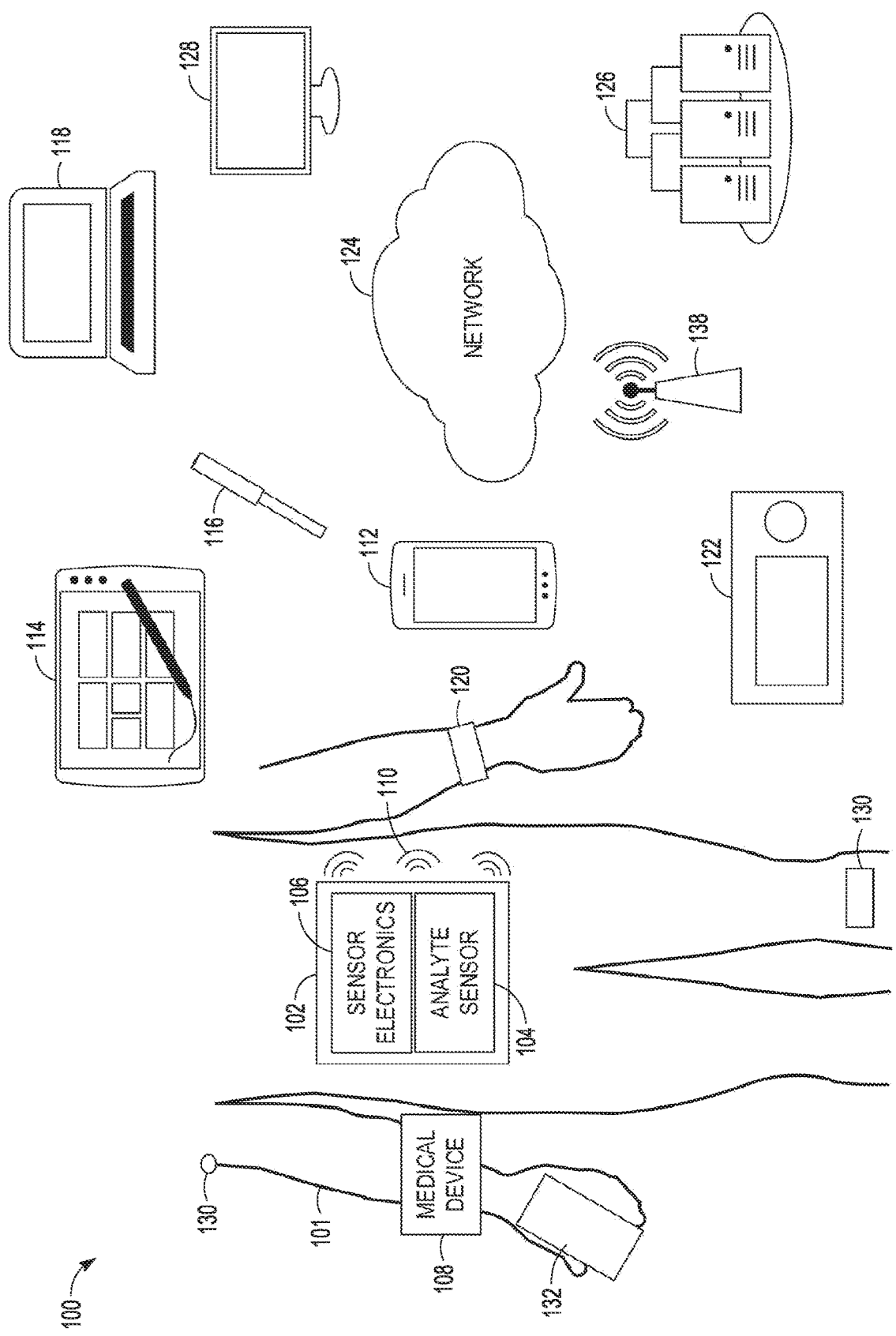
FIG. 1 is a diagram showing one example of an environment including an analyte sensor system.

FIG. 1 is a diagram showing one example of an environment 100 including an analyte sensor system 102. The analyte sensor system 102 is coupled to a host 101, which may be a human patient. In some examples, the host is subject to a temporary or permanent diabetes condition or other health condition that makes analyte monitoring useful.

The analyte sensor system 102 includes an analyte sensor 104. In some examples, the analyte sensor 104 is or includes a glucose sensor configured to measure a glucose concentration in the host 101. The analyte sensor 104 can be exposed to analyte at the host 101 in any suitable way. In some examples, the analyte sensor 104 is fully implantable under the skin of the host 101. In other examples, the analyte sensor 104 is wearable on the body of the host 101 (e.g., on the body but not under the skin). Also, in some examples, the analyte sensor 104 is a transcutaneous device (e.g., with a sensor residing at least partially under or in the skin of a host). It should be understood that the devices and methods described herein can be applied to any device capable of detecting a concentration of an analyte, such as glucose, and providing an output signal that represents the concentration of the analyte.

According to various embodiments, the glucose detected can be D-glucose. However, it is possible to detect any stereoisomer or blend of stereoisomers of glucose as well as any glucose in an open-chain form, cyclic form, or a mixture thereof. In the example of FIG. 1, the analyte sensor system 102 also includes sensor electronics 106. In some examples, the sensor electronics 106 and analyte sensor 104 are provided in a single integrated package. In other examples, the analyte sensor 104 and sensor electronics 106 are provided as separate components or modules. For example, the analyte sensor system 102 may include a disposable (e.g., single-use) sensor mounting unit (FIG. 3) that may include the analyte sensor 104, a component for attaching the sensor 104 to a host (e.g., an adhesive pad), and/or a mounting structure configured to receive a sensor electronics unit including some or all of the sensor electronics 106 shown in FIG. 2. The sensor electronics unit may be reusable.

The analyte sensor 104 may use any known method, including invasive, minimally-invasive, or non-invasive sensing techniques (e.g., optically excited fluorescence, microneedle, transdermal monitoring of glucose), to provide a raw sensor signal indicative of the concentration of the analyte in the host 101. The raw sensor signal may be converted into calibrated and/or filtered analyte concentration data used to provide a useful value of the analyte concentration (e.g., estimated blood glucose concentration level) to a user, such as the host or a caretaker (e.g., a parent, a relative, a guardian, a teacher, a doctor, a nurse, or any other individual that has an interest in the wellbeing of the host 101).

In some examples, the analyte sensor 104 is or includes a continuous glucose sensor. A continuous glucose sensor can be or include a subcutaneous, transdermal (e.g., transcutaneous), and/or intravascular device. In some embodiments, such a sensor or device may recurrently (e.g., periodically or intermittently) analyze sensor data. The glucose sensor may use any method of glucose measurement, including enzymatic, chemical, physical, electrochemical, spectrophotometric, polarimetric, calorimetric, iontophoretic, radiometric, immunochemical, and the like. In various examples, the analyte sensor system 102 may be or include a continuous glucose monitor sensor available from DexCom™ (e.g., the DexCom G5™ sensor or DexCom G6™ sensor or any variation thereof), from Abbott™ (e.g., the Libre™ sensor), or from Medtronic™ (e.g., the Enlite™ sensor).

In some examples, analyte sensor 104 includes an implantable glucose sensor, such as described with reference to U.S. Pat. No. 6,001,067 and U.S. Patent Publication No. US-2005-0027463-A1, which are incorporated by reference. In some examples, analyte sensor 104 includes a transcutaneous glucose sensor, such as described with reference to U.S. Patent Publication No. US-2006-0020187-A1, which is incorporated by reference. In some examples, analyte sensor 104 may be configured to be implanted in a host vessel or extracorporeally, such as is described in U.S. Patent Publication No. US-2007-0027385-A1, co-pending U.S. Patent Publication No. US-2008-0119703-A1 filed Oct. 4, 2006, U.S. Patent Publication No. US-2008-0108942-A1 filed on Mar. 26, 2007, and U.S. Patent Application No. US-2007-0197890-A1 filed on Feb. 14, 2007, all of which are incorporated by reference. In some examples, the continuous glucose sensor may include a transcutaneous sensor such as described in U.S. Pat. No. 6,565,509 to Say et al., which is incorporated by reference. In some examples, analyte sensor 104 may include a continuous glucose sensor that includes a subcutaneous sensor such as described with reference to U.S. Pat. No. 6,579,690 to Bonnecaze et al. or U.S. Pat. No. 6,484,046 to Say et al., which are incorporated by reference. In some examples, the continuous glucose sensor may include a refillable subcutaneous sensor such as described with reference to U.S. Pat. No. 6,512,939 to Colvin et al., which is incorporated by reference. The continuous glucose sensor may include an intravascular sensor such as described with reference to U.S. Pat. No. 6,477,395 to Schulman et al., which is incorporated by reference. The continuous glucose sensor may include an intravascular sensor such as described with reference to U.S. Pat. No. 6,424,847 to Mastrototaro et al., which is incorporated by reference.

The environment 100 may also include a second medical device 108. The second medical device 108 may be or include a drug delivery device such as an insulin pump or an insulin pen. In some examples, the medical device 108 includes one or more sensors, such as another analyte sensor, a heart rate sensor, a respiration sensor, a motion sensor (e.g. accelerometer), posture sensor (e.g. 3-axis accelerometer), acoustic sensor (e.g. to capture ambient sound or sounds inside the body). The medical device 108 may be wearable, e.g., on a watch, glasses, contact lens, patch, wristband, ankle band, or other wearable item, or may be incorporated into a handheld device (e.g., a smartphone). In some examples, the medical device 108 includes a multi-sensor patch that may, for example, detect one or more of an analyte level (e.g., glucose, lactate, insulin or other substance), heart rate, respiration (e.g., using impedance), activity (e.g., using an accelerometer), posture (e.g., using an accelerometer), galvanic skin response, tissue fluid levels (e.g., using impedance or pressure).

In some examples, the analyte sensor system 102 and the second medical device 108 communicate with one another. Communication between the analyte sensor system 102 and medical device 108 may occur over any suitable wired connection and/or via a wireless communication signal 110. For example, the analyte sensor system 102 may be configured to communicate using via radio frequency (e.g., Bluetooth, Medical Implant Communication System (MICS), Wi-Fi, near field communication (NFC), radio frequency identification (RFID), Zigbee, Z-Wave or other communication protocols), optically (e.g., infrared), sonically (e.g., ultrasonic), or a cellular protocol (e.g., Code Division Multiple Access (CDMA) or Global System for Mobiles (GSM)), or via a wired connection (e.g., serial, parallel, etc.).

In some examples, the environment 100 also includes a wearable sensor 130. The wearable sensor 130 can include a sensor circuit (e.g., a sensor circuit configured to detect a glucose concentration or other analyte concentration) and a communication circuit, which may, for example, be an NFC circuit. In some examples, information from the wearable sensor 130 may be retrieved from the wearable sensor 130 using a user computing device 132, such as a smart phone, that is configured to communicate with the wearable sensor 130 via the wearable sensor's communication circuit, for example, when the user device 132 is placed near the wearable sensor 130. For example, swiping the user device 132 over the sensor 130 may retrieve sensor data from the wearable sensor 130 using NFC or other suitable wireless communication. The use of NFC communication may reduce power consumption by the wearable sensor 130, which may reduce the size of a power source (e.g., battery or capacitor) in the wearable sensor 130 or extend the usable life of the power source. In some examples, the wearable sensor 130 may be wearable on an upper arm as shown. In some examples, a wearable sensor 130 may additionally or alternatively be on the upper torso of the patient (e.g., over the heart or over a lung), which may, for example, facilitate detecting heart rate, respiration, or posture. A wearable sensor 136 may also be on the lower body (e.g., on a leg).

In some examples, an array or network of sensors may be associated with the patient. For example, one or more of the analyte sensor system 102, medical device 108, wearable device 120 such as a watch, and an additional wearable sensor 130 may communicate with one another via wired or wireless (e.g., Bluetooth, MICS, NFC or any of the other options described above) communication. The additional wearable sensor 130 may be any of the examples described above with respect to medical device 108. The analyte sensor system 102, medical device 108, and additional sensor 130 on the host 101 are provided for illustration and description and are not necessarily drawn to scale.

The environment 100 may also include one or more computing devices, such as a hand-held smart device (e.g., smart device) 112, tablet 114, smart pen 116 (e.g., insulin delivery pen with processing and communication capability), computer 118, a wearable device 120 such as a watch, or peripheral medical device 122 (which may be a proprietary device such as a proprietary user device available from DexCom), any of which may communicate with the analyte sensor system 102 via a wireless communication signal 110, and may also communicate over a network 124 with a server system (e.g., remote data center) or with a remote terminal 128 to facilitate communication with a remote user (not shown) such as a technical support staff member or a clinician.

The wearable device 120 may include an activity sensor, a heart rate monitor (e.g., light-based sensor or electrode-based sensor), a respiration sensor (e.g., acoustic- or electrode-based), a location sensor (e.g., GPS), or other sensors.

In some examples, the environment 100 includes a server system 126. The server system 126 can include one or more computing devices, such as one or more server computing devices. In some examples, the server system 126 is used to collect analyte data from the analyte sensor system 102 and/or analyte or other data from the plurality of other devices, and to perform analytics on collected data, generate or apply universal or individualized models for glucose levels, and communicate such analytics, models, or information based thereon back to one or more of the devices in the environment 100. In some examples, the server system 126 gathers inter-host and/or intra-host break-in data to generate one or more break-in characteristics, as described herein.

The environment 100 may also include a wireless access point (WAP) 138 used to communicatively couple one or more of analyte sensor system 102, network 124, server system 126, medical device 108 or any of the peripheral devices described above. For example, WAP 138 may provide Wi-Fi and/or cellular connectivity within environment 100. Other communication protocols, such as NFC or Bluetooth, may also be used among devices of the environment 100.

Figure 2:
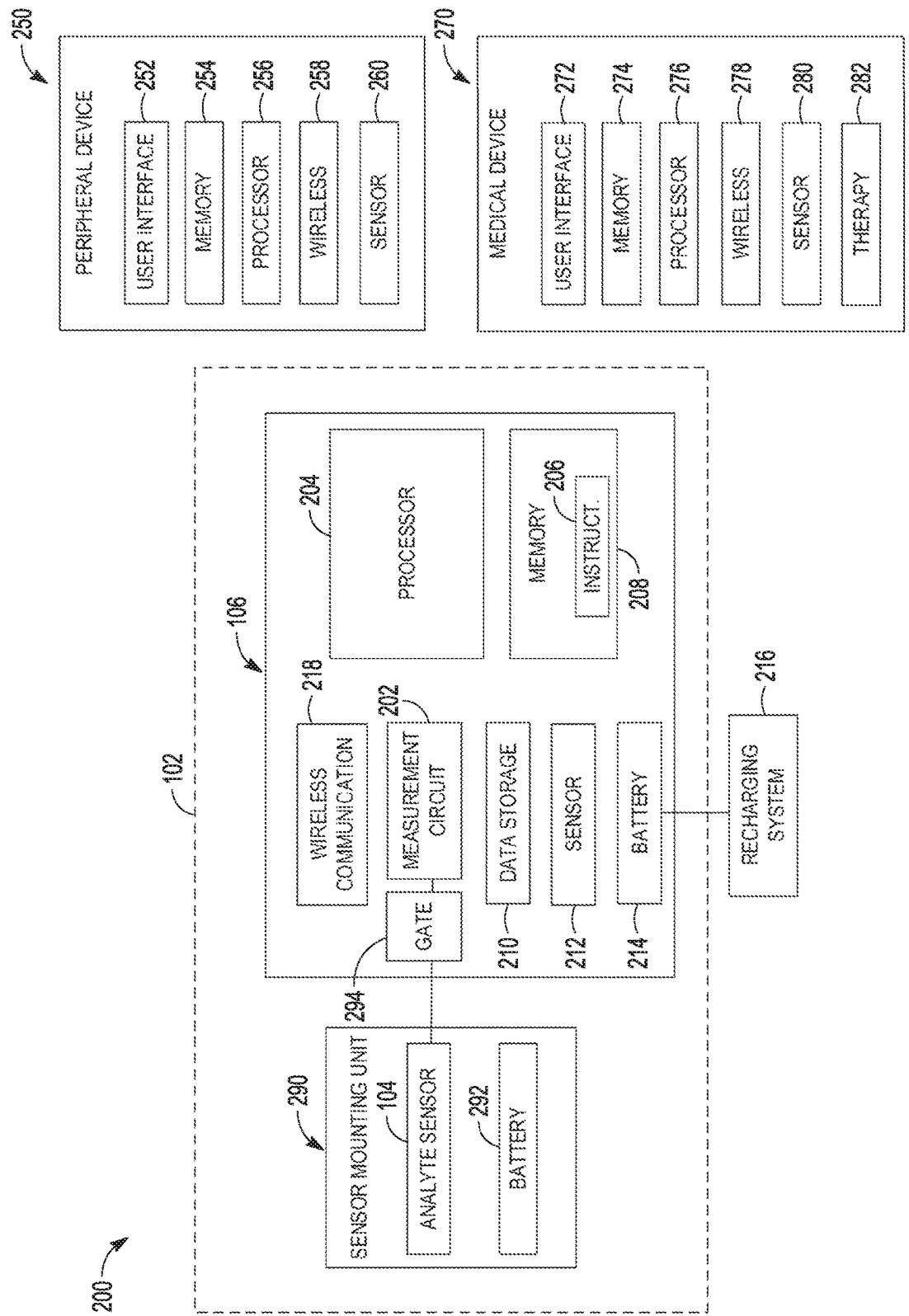
FIG. 2 is a diagram showing one example of a medical device system including the analyte sensor system of FIG. 1.

FIG. 2 is a diagram showing one example of a medical device system 200 including the analyte sensor system 102 of FIG. 1. In the example of FIG. 2, the analyte sensor system 102 includes sensor electronics 106 and a sensor mounting unit 290. While a specific example of division of components between the sensor mounting unit 290 and sensor electronics 106 is shown, it is understood that some examples may include additional components in the sensor mounting unit 290 or in the sensor electronics 106, and that some of the components (e.g., a battery or supercapacitor) that are shown in the sensor electronics 106 may be alternatively or additionally (e.g., redundantly) provided in the sensor mounting unit 290.

In the example shown in FIG. 2, the sensor mounting unit 290 includes the analyte sensor 104 and a battery 292. In some examples, the sensor mounting unit 290 may be replaceable, and the sensor electronics 106 may include a debouncing circuit (e.g., gate with hysteresis or delay) to avoid, for example, recurrent execution of a power-up or power down process when a battery is repeatedly connected and disconnected or avoid processing of noise signal associated with removal or replacement of a battery.

The sensor electronics 106 may include electronics components that are configured to process sensor information, such as raw sensor signals, and generate corresponding analyte concentration values. The sensor electronics 106 may, for example, include electronic circuitry associated with measuring, processing, storing, or communicating continuous analyte sensor data, including prospective algorithms associated with processing and calibration of the raw sensor signal. The sensor electronics 106 may include hardware, firmware, and/or software that enables measurement of levels of the analyte via a glucose sensor. Electronic components may be affixed to a printed circuit board (PCB), or the like, and can take a variety of forms. For example, the electronic components may take the form of an integrated circuit (IC), such as an Application-Specific Integrated Circuit (ASIC), a microcontroller, and/or a processor.

In the example of FIG. 2, the sensor electronics 106 include a measurement circuit 202 (e.g., potentiostat) coupled to the analyte sensor 104 and configured to recurrently obtain analyte sensor readings using the analyte sensor 104. For example, the measurement circuit 202 may continuously or recurrently measure a raw sensor signal indicating a current flow at the analyte sensor 104 between a working electrode and a counter or reference (e.g., counter-reference) electrode. The sensor electronics 106 may include a gate circuit 294, which may be used to gate the connection between the measurement circuit 202 and the analyte sensor 104. For example, the analyte sensor 104 may accumulate charge over an accumulation period. After the accumulation period, the gate circuit 294 is opened so that the measurement circuit 202 can measure the accumulated charge. Gating the analyte sensor 104 may improve the performance of the sensor system 102 by creating a larger signal to noise or interference ratio (e.g., because charge accumulates from an analyte reaction, but sources of interference, such as the presence of acetaminophen near a glucose sensor, do not accumulate, or accumulate less than the charge from the analyte reaction).

The sensor electronics 106 may also include a processor 204. The processor 204 is configured to retrieve instructions 206 from memory 208 and execute the instructions 206 to control various operations in the analyte sensor system 102. For example, the processor 204 may be programmed to control application of bias potentials to the analyte sensor 104 via a potentiostat at the measurement circuit 202, interpret raw sensor signals from the analyte sensor 104, and/or compensate for environmental factors.

The processor 204 may also save information in data storage memory 210 or retrieve information from data storage memory 210. In various examples, data storage memory 210 may be integrated with memory 208, or may be a separate memory circuit, such as a non-volatile memory circuit (e.g., flash RAM). Examples of systems and methods for processing sensor analyte data are described in more detail herein and in U.S. Pat. Nos. 7,310,544 and 6,931,327.

The sensor electronics 106 may also include a sensor 212, which may be coupled to the processor 204. The sensor 212 may be a temperature sensor, accelerometer, or another suitable sensor. The sensor electronics 106 may also include a power source such as a capacitor or battery 214, which may be integrated into the sensor electronics 106, or may be removable, or part of a separate electronics unit. The battery 214 (or other power storage component, e.g., capacitor) may optionally be rechargeable via a wired or wireless (e.g., inductive or ultrasound) recharging system 216. The recharging system 216 may harvest energy or may receive energy from an external source or on-board source. In various examples, the recharge circuit may include a triboelectric charging circuit, a piezoelectric charging circuit, an RF charging circuit, a light charging circuit, an ultrasonic charging circuit, a heat charging circuit, a heat harvesting circuit, or a circuit that harvests energy from the communication circuit. In some examples, the recharging circuit may recharge the rechargeable battery using power supplied from a replaceable battery (e.g., a battery supplied with a base component).

The sensor electronics 106 may also include one or more supercapacitors in the sensor electronics unit (as shown), or in the sensor mounting unit 290. For example, the supercapacitor may allow energy to be drawn from the battery 214 in a highly consistent manner to extend the life of the battery 214. The battery 214 may recharge the supercapacitor after the supercapacitor delivers energy to the communication circuit or to the processor 204, so that the supercapacitor is prepared for delivery of energy during a subsequent high-load period. In some examples, the supercapacitor may be configured in parallel with the battery 214. A device may be configured to preferentially draw energy from the supercapacitor, as opposed to the battery 214. In some examples, a supercapacitor may be configured to receive energy from a rechargeable battery for short-term storage and transfer energy to the rechargeable battery for long-term storage.

The supercapacitor may extend an operational life of the battery 214 by reducing the strain on the battery 214 during the high-load period. In some examples, a supercapacitor removes at least 10% of the strain off the battery during high-load events. In some examples, a supercapacitor removes at least 20% of the strain off the battery during high-load events. In some examples, a supercapacitor removes at least 30% of the strain off the battery during high-load events. In some examples, a supercapacitor removes at least 50% of the strain off the battery during high-load events.

The sensor electronics 106 may also include a wireless communication circuit 218, which may for example include a wireless transceiver operatively coupled to an antenna. The wireless communication circuit 218 may be operatively coupled to the processor 204 and may be configured to wirelessly communicate with one or more peripheral devices or other medical devices, such as an insulin pump or smart insulin pen.

In the example of FIG. 2, the medical device system 200 also includes an optional peripheral device 250. The peripheral device 250 may be any suitable user computing device such as, for example, a wearable device (e.g., activity monitor), such as a wearable device 120. In other examples, the peripheral device 250 may be a hand-held smart device (e.g., smartphone or other device such as a proprietary handheld device available from Dexcom), a tablet 114, a smart pen 116, or special-purpose computer 118 shown in FIG. 1.

The peripheral device 250 may include a UI 252, a memory circuit 254, a processor 256, a wireless communication circuit 258, a sensor 260, or any combination thereof. The peripheral device 250 may not necessarily include all the components shown in FIG. 2. The peripheral device 250 may also include a power source, such as a battery.

The UI 252 may, for example, be provided using any suitable input/output device or devices of the peripheral device 250 such as, for example, a touch-screen interface, a microphone (e.g., to receive voice commands), or a speaker, a vibration circuit, or any combination thereof. The UI 252 may receive information from the host or another user (e.g., instructions, glucose values). The UI 252 may also deliver information to the host or other user, for example, by displaying UI elements at the UI 252. For example, UI elements can indicate glucose or other analyte concentration values, glucose or other analyte trends, glucose or other analyte alerts, etc. Trends can be indicated by UI elements such as arrows, graphs, charts, etc.

The processor 256 may be configured to present information to a user, or receive input from a user, via the UI 252. The processor 256 may also be configured to store and retrieve information, such as communication information (e.g., pairing information or data center access information), user information, sensor data or trends, or other information in the memory circuit 254. The wireless communication circuit 258 may include a transceiver and antenna configured to communicate via a wireless protocol, such as any of the wireless protocols described herein. The sensor 260 may, for example, include an accelerometer, a temperature sensor, a location sensor, biometric sensor, or blood glucose sensor, blood pressure sensor, heart rate sensor, respiration sensor, or other physiologic sensor.

The peripheral device 250 may be configured to receive and display sensor information that may be transmitted by sensor electronics 106 (e.g., in a customized data package that is transmitted to the display devices based on their respective preferences). Sensor information (e.g., blood glucose concentration level) or an alert or notification (e.g., "high glucose level", "low glucose level" or "fall rate alert" may be communicated via the UI 252 (e.g., via visual display, sound, or vibration). In some examples, the peripheral device 250 may be configured to display or otherwise communicate the sensor information as it is communicated from the sensor electronics 106 (e.g., in a data package that is transmitted to respective display devices). For example, the peripheral device 250 may transmit data that has been processed (e.g., an estimated analyte concentration level that may be determined by processing raw sensor data), so that a device that receives the data may not be required to further process the data to determine usable information (such as the estimated analyte concentration level). In other examples, the peripheral device 250 may process or interpret the received information (e.g., to declare an alert based on glucose values or a glucose trend). In various examples, the peripheral device 250 may receive information directly from sensor electronics 106, or over a network (e.g., via a cellular or Wi-Fi network that receives information from the sensor electronics 106 or from a device that is communicatively coupled to the sensor electronics 106).

In the example of FIG. 2, the medical device system 200 includes an optional medical device 270. For example, the medical device 270 may be used in addition to or instead of the peripheral device 250. The medical device 270 may be or include any suitable type of medical or other computing device including, for example, the medical device 108, peripheral medical device 122, wearable device 120, wearable sensor 130, or wearable sensor 136 shown in FIG. 1. The medical device 270 may include a UI 272, a memory circuit 274, a processor 276, a wireless communication circuit 278, a sensor 280, a therapy circuit 282, or any combination thereof.

Similar to the UI 252, the UI 272 may be provided using any suitable input/output device or devices of the medical device 270 such as, for example, a touch-screen interface, a microphone, or a speaker, a vibration circuit, or any combination thereof. The UI 272 may receive information from the host or another user (e.g., glucose values, alert preferences, calibration coding). The UI 272 may also deliver information to the host or other user, for example, by displaying UI elements at the UI 252. For example, UI elements can indicate glucose or other analyte concentration values, glucose or other analyte trends, glucose or other analyte alerts, etc. Trends can be indicated by UI elements such as arrows, graphs, charts, etc.

The processor 276 may be configured to present information to a user, or receive input from a user, via the UI 272. The processor 276 may also be configured to store and retrieve information, such as communication information (e.g., pairing information or data center access information), user information, sensor data or trends, or other information in the memory circuit 274. The wireless communication circuit 278 may include a transceiver and antenna configured communicate via a wireless protocol, such as any of the wireless protocols described herein.

The sensor 280 may, for example, include an accelerometer, a temperature sensor, a location sensor, biometric sensor, or blood glucose sensor, blood pressure sensor, heart rate sensor, respiration sensor, or other physiologic sensor. The medical device 270 may include two or more sensors (or memories or other components), even though only one sensor 280 is shown in the example in FIG. 2. In various examples, the medical device 270 may be a smart handheld glucose sensor (e.g., blood glucose meter), drug pump (e.g., insulin pump), or other physiologic sensor device, therapy device, or combination thereof.

In examples where medical device 270 is or includes an insulin pump, the pump and analyte sensor system 102 may be in two-way communication (e.g., so the pump can request a change to an analyte transmission protocol, e.g., request a data point or request data on a more frequent schedule), or the pump and analyte sensor system 102 may communicate using one-way communication (e.g., the pump may receive analyte concentration level information from the analyte sensor system). In one-way communication, a glucose value may be incorporated in an advertisement message, which may be encrypted with a previously-shared key. In a two-way communication, a pump may request a value, which the analyte sensor system 102 may share, or obtain and share, in response to the request from the pump, and any or all of these communications may be encrypted using one or more previously-shared keys. An insulin pump may receive and track analyte (e.g., glucose) values transmitted from analyte sensor system 102 using one-way communication to the pump for one or more of a variety of reasons. For example, an insulin pump may suspend or activate insulin administration based on a glucose value being below or above a threshold value.

In some examples, the medical device system 200 includes two or more peripheral devices and/or medical devices that each receive information directly or indirectly from the analyte sensor system 102. Because different display devices provide many different user interfaces, the content of the data packages (e.g., amount, format, and/or type of data to be displayed, alarms, and the like) may be customized (e.g., programmed differently by the manufacturer and/or by an end user) for each particular device. For example, referring now to the example of FIG. 1, a plurality of different peripheral devices may be in direct wireless communication with sensor electronics 106 (e.g., such as an on-skin sensor electronics 106 that are physically connected to the continuous analyte sensor 104) during a sensor session to enable a plurality of different types and/or levels of display and/or functionality associated with the displayable sensor information, or, to save battery power in the sensor system 102, one or more specified devices may communicate with the analyte sensor system 102 and relay (i.e., share) information to other devices directly or through a server system (e.g., a network-connected data center) 126.

Figure 3:
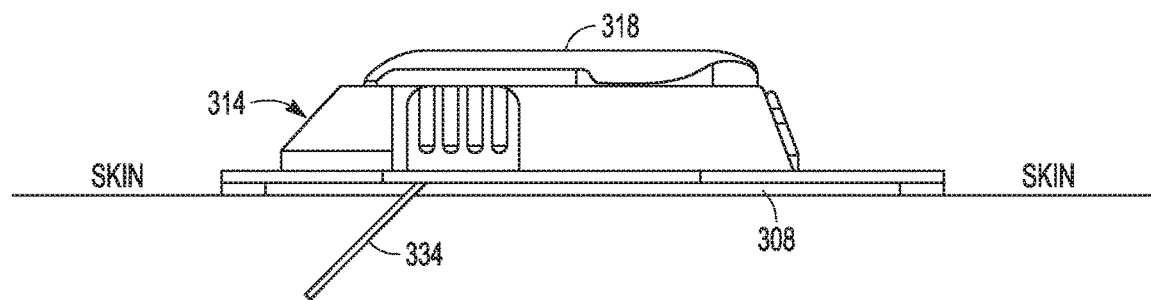
FIG. 3 is an illustration of an example analyte sensor.

FIG. 3 is a side view of an example analyte sensor 334 that may be implanted into a host. A mounting unit 314 may be adhered to the host's skin using an adhesive pad 308. The adhesive pad 308 may be formed from an extensible material, which may be removably attached to the skin using an adhesive. Electronics unit 318 may mechanically couple to the mounting unit 314. In some examples, the electronics unit 318 and mounting unit 314 are arranged in a manner similar to the sensor electronics 106 and sensor mounting unit 290 shown in FIGS. 1 and 2.

Figure 4:
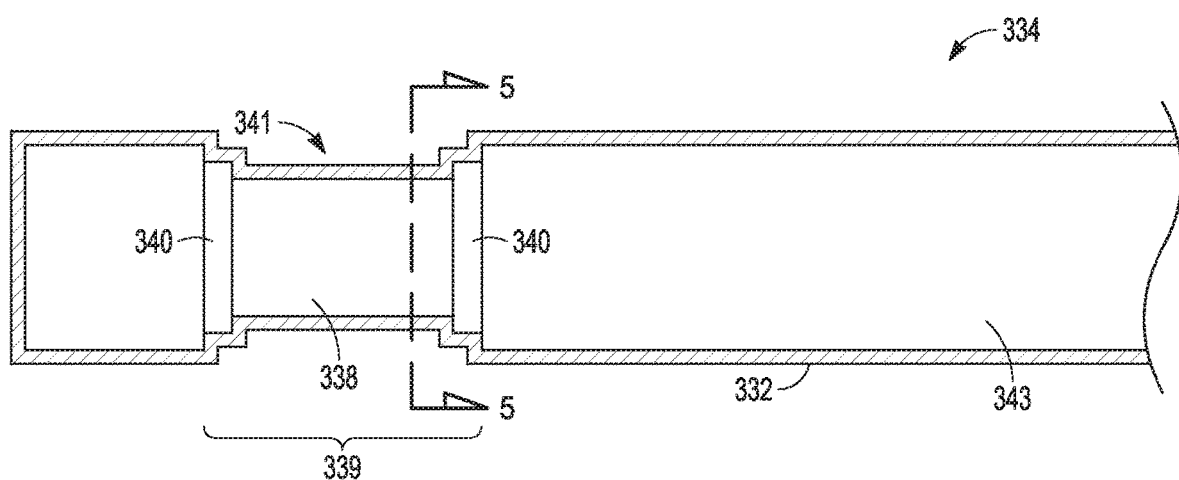
FIG. 4 is an enlarged view of an example analyte sensor portion of the analyte sensor system shown in FIG. 3.

FIG. 4 is an enlarged view of a distal portion of the analyte sensor 334. The analyte sensor 334 may be adapted for insertion under the host's skin and may be mechanically coupled to the mounting unit 314 and electrically coupled to the electronics unit 318. The example analyte sensor 334 shown in FIG. 4 includes an elongated conductive body 341. The elongated conductive body 341 can include a core with various layers positioned thereon. A first layer 338 that at least partially surrounds the core and includes a working electrode, for example located in window 339). In some examples, the core and the first layer 338 are made of a single material (such as, for example, platinum). In some examples, the elongated conductive body 341 is a composite of two conductive materials, or a composite of at least one conductive material and at least one non-conductive material. A membrane system 332 is located over the working electrode and may cover other layers and/or electrodes of the sensor 334, as described herein.

The first layer 338 may be formed of a conductive material. The working electrode (at window 339) is an exposed portion of the surface of the first layer 338. Accordingly, the first layer 338 is formed of a material configured to provide a suitable electroactive surface for the working electrode. Examples of suitable materials include, but are not limited to, platinum, platinum-iridium, gold, palladium, iridium, graphite, carbon, a conductive polymer, an alloy thereof, and/or the like.

A second layer 340 surrounds at least a portion of the first layer 338, thereby defining boundaries of the working electrode. In some examples, the second layer 340 serves as an insulator and is formed of an insulating material, such as polyimide, polyurethane, parylene, or any other suitable insulating materials or materials. According to various embodiments, a polyimide may include a polymer including at least one repeating unit according to Formula I:

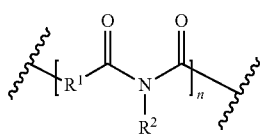

(I)

wherein $R^1$ is chosen from —NH—, or substituted or unsubstituted $(C_1-C_{40})$hydrocarbylene. In further embodiments, $R^1$ is substituted or unsubstituted $(C_1-C_{40})$alkylene, $(C_2-C_{40})$alkylene, $(C_2-C_{40})$alkenylene, $(C_4-C_{20})$arylene, $(C_4-C_{20})$cycloalkylene, and $(C_4-C_{20})$ aralkylene. According to some embodiments $R^2$ is chosen from —H, —OH, $NH_2$, or substituted or unsubstituted $(C_1-C_{40})$hydrocarbyl. In further embodiments, $R^2$ is chosen from substituted or unsubstituted $(C_1-C_{40})$alkyl, $(C_2-C_{40})$alkylenyl, $(C_2-C_{40})$alkenyl, $(C_4-C_{20})$aryl, $(C_4-C_{20})$cycloalkyl, and $(C_4-C_{20})$ aralkyl.

According to various embodiments, a polyurethane is a reaction product of a reaction mixture that includes a diisocyanate, a polyester polyol, which can have a melting temperature of at least about 30° C., and a chain extender. The diisocyanate can range from about 0.5 wt % to about 40 wt % of the reaction mixture, about 1 wt % to about 10 wt %, or less than, equal to, or greater than about 0.5 wt %, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or 40 wt % of the reaction mixture. The amount of the diisocyanate in the reactive mixture can be expressed in terms of an isocyanate index. An isocyanate index can be generally understood to refer to the ratio of the equivalent amount of isocyanate functional groups used relative to the theoretical equivalent amount times of 100. The theoretical equivalent amount is equal to one equivalent isocyanate functional group per one equivalent hydroxyl group; this is an index of 100. According to various examples, the isocyanate index of the reactive mixture is in a range of from about 0.99 to about 1.20, about 1.00 to about 1.10, or less than equal to, or greater than about 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, or 1.20.

An example of a suitable diisocyanate includes a diisocyanate according to Formula II having the structure:

(II)

In Formula II, $R^3$ is chosen from substituted or unsubstituted $(C_1-C_{40})$alkylene, $(C_2-C_{40})$alkenylene, $(C_4-C_{20})$arylene, $(C_4-C_{20})$arylene-$(C_1-C_{40})$alkylene-$(C_4-C_{20})$arylene, $(C_4-C_{20})$cycloalkylene, and $(C_4-C_{20})$aralkylene. In additional examples, the diisocyanate is chosen from dicyclohexylmethane-4,4'-diisocyanate, isophorone diisocyanate, hexamethylene diisocyanate, 1,4-phenylene diisocyanate, 1,3-phenylene diisocyanate, m-xylylene diisocyanate, tolylene-2,4-diisocyanate, toluene 2,4-diisocyanate, tolylene-2,6-diisocyanate, poly(hexamethylene diisocyanate), 1,4-cyclohexylene diisocyanate, 4-chloro-6-methyl-1,3-phenylene diisocyanate, hexamethylene diisocyanate, toluylene diisocyanate, diphenylmethane 4,4'-diisocyanate, 1,4-diisocyanatobutane, 1,8-diisocyanatooctane, 2,6-toluene diisocyanate, 2,5-toluene diisocyanate, 2,4-toluene diisocyanate, m-phenylene diisocyanate, p-phenylene diisocyanate, methylene bis(o-chlorophenyl diisocyanate, methylenediphenylene-4,4'-diisocyanate, (4,4'-diisocyanato-3,3',5,5'-tetraethyl) diphenylmethane, 4,4'-diisocyanato-3,3'-dimethoxybiphenyl (o-dianisidine diisocyanate), 5-chloro-2,4-toluene diisocyanate, 1-chloromethyl-2,4-diisocyanato benzene, tetramethyl-m-xylylene diisocyanate, 1,6-diisocyanatohexane 1,12-diisocyanatododecane, 2-methyl-1,5-diisocyanatopentane, methylenedicyclohexylene-4,4'-diisocyanate, 3-isocyanatomethyl-3,5,5-trimethylcyclohexyl isocyanate, 2,2,4-trimethylhexyl diisocyanate, or a mixture thereof.

The polyester polyol can be in a range of from about 0.5 wt % to about 40 wt % of the reaction mixture, about 1 wt % to about 10 wt %, or less than, equal to, or greater than about 0.5 wt %, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or 40 wt % of the reaction mixture. The polyester polyol can include any suitable number of hydroxyl groups. For example, the polyester polyol can include four hydroxyl groups or three hydroxyl groups. The polyester polyol can even include two hydroxyl groups such that the polyester polyol is a polyester diol. In general, the polyester polyol can be a product of a condensation reaction such as a polycondensation reaction. However, the polyester polyol is not made via a ring opening polymerization reaction products.

In examples where polyester polyol is made according to a condensation reaction, the reaction can be between one or more carboxylic acids and one or more polyols. An example of a suitable carboxylic acid includes a carboxylic acid according to Formula III, having the structure:

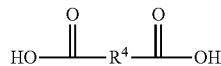
(III)

In Formula III, $R^4$ is chosen from substituted or unsubstituted $(C_1-C_{40})$alkylene, $(C_2-C_{40})$alkylene, $(C_2-C_{40})$alkenylene, $(C_4-C_{20})$arylene, $(C_4-C_{20})$cycloalkylene, and $(C_4-C_{20})$ aralkylene. Specific examples of suitable carboxylic acids include glycolic acid (2-hydroxyethanoic acid), lactic acid (2-hydroxypropanoic acid), succinic acid (butanedioic acid), 3-hydoxybutanoic acid, 3-hydroxypentanoic acid, terepthalic acid (benzene-1,4-dicarboxylic acid), naphthalene dicarboxylic acid, 4-hydroxybenzoic acid, 6-hydroxynaphtalane-2-carboxylic acid, oxalic acid, malonic acid (propanedioic acid), adipic acid (hexanedioic acid), pimelic acid (heptanedioic acid), ethonic acid, suberic acid (octanedioic acid), azelaic acid (nonanedioic acid), sebacic acid (decanedioic acid), glutaric acid (pentanedioic acid), dedecandioic acid, brassylic acid, thapsic acid, maleic acid ((2Z)-but-2-enedioic acid), fumaric acid ((2E)-but-2-enedioic acid), glutaconic acid (pent-2-enedioic acid), 2-decenedioic acid, traumatic acid ((2E)-dodec-2-enedioic acid), muconic acid ((2E,4E)-hexa-2,4-dienedioic acid), glutinic acid, citraconic acid((2Z)-2-methylbut-2-enedioic acid), mesaconic acid ((2E)-2-methyl-2-butenedioic acid), itaconic acid (2-methylidenebutanedioic acid), malic acid (2-hydroxybutanedioic acid), aspartic acid (2-aminobutanedioic acid), glutamic Acid (2-aminopentanedioic acid), tartonic acid, tartaric acid (2,3-dihydroxybutanedioic acid), diaminopimelic acid ((2R,6S)-2,6-diaminoheptanedioic acid), saccharic acid ((2S,3S,4S,5R)-2,3,4,5-tetrahydroxyhexanedioic acid), mexooxalic acid, oxaloacetic acid (oxobutanedioic acid), acetonedicarboxylic acid (3-oxopentanedioic acid), arbinaric acid, phthalic acid (benzene-1,2-dicarboxylic acid), isophtalic acid, diphenic acid, 2,6-naphtalenedicarboxylic acid, or a mixture thereof.

An example of a suitable polyol includes a polyol according to Formula IV, having the structure:

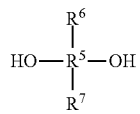
(IV)

In Formula IV, $R^5$ is chosen from substituted or unsubstituted $(C_1-C_{40})$alkylene, $(C_2-C_{40})$alkenylene, $(C_4-C_{20})$ arylene, $(C_1-C_{40})$acylene, $(C_4-C_{20})$cycloalkylene, $(C_4-C_{20})$ aralkylene, and $(C_1-C_{40})$alkoxyene, and $R^6$ and $R^7$ are independently chosen from —H, —OH, substituted or unsubstituted $(C_1-C_{40})$alkyl, $(C_2-C_{40})$alkenyl, $(C_4-C_{20})$aryl, $(C_1-C_{20})$acyl, $(C_4-C_{20})$cycloalkyl, $(C_4-C_{20})$aralkyl, and $(C_1-C_{40})$alkoxy. $R^6$ and $R^7$ are independently chosen from $(C_1-C_{40})$hydrocarbyl. An example of another suitable polyol includes a polyol according to Formula V, having the structure:

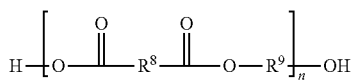
(V)

In Formula V, $R^8$ and $R^9$ are independently chosen from substituted or unsubstituted $(C_1-C_{40})$alkylene, $(C_2-C_{40})$alkenylene, $(C_4-C_{20})$arylene, $(C_1-C_{40})$acylene, $(C_4-C_{20})$cycloalkylene, $(C_4-C_{20})$aralkylene, and $(C_1-C_{40})$alkoxyene and n is a positive integer greater than or equal to 1. An example of another suitable polyol includes a polyol according to Formula VI, having the structure:

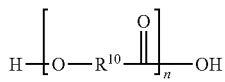
(VI)

In Formula VI, $R^{10}$ is chosen from substituted or unsubstituted $(C_1-C_{40})$alkylene, $(C_2-C_{40})$alkenylene, $(C_4-C_{20})$ arylene, $(C_1-C_{40})$acylene, $(C_4-C_{20})$cycloalkylene, $(C_4-C_{20})$ aralkylene, and $(C_1-C_{40})$alkoxyene and n is a positive integer greater than or equal to 1. In specific examples, the polyester polyol includes one or more of polyglycolic acid (poly[oxy(1-oxo-1,2-ethanediyl)]), polybutylene succinate (poly(tetramethylene succinate)), poly(3-hydroxybutyrate-co-3-hydroxyvalerate), polyethylene terephthalate (poly (ethyl benzene-1,4-dicarboxylate)), polybutylene terephthalate (poly(oxy-1,4-butanediyloxycarbonyl-1,4-phenylenecarbonyl)), polytrimethylene terephthalate (poly(trimethylene terephthalate); poly(oxy-1,3-propanediyloxycarbonyl-1, 4-phenylenecarbonyl)), polyethylene naphthalate (poly(ethylene 2,6-naphthalate)), poly(1,4-butylene adipate), poly(1, 6-hexamethylene adipate), poly(ethylene-adipate), mixtures thereof, and copolymers thereof. However, the polyester polyol is free of polycaprolactone polyol ((1,7)-polyoxepan-2-one). The chain extender can be in a range of from about 0.5 wt % to about 40 wt % of the reaction mixture, about 1 wt % to about 10 wt %, or less than, equal to, or greater than about 0.5 wt %, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, or 40 wt % of the reaction mixture.

The diol chain extender has weight-average molecular weight of less than about 250 daltons. For example a weight-average molecular weight of the diol chain extender can be in a range of from about 30 daltons to about 250 daltons, about 50 daltons to about 150 daltons, or less than equal to, or greater than about 30 daltons, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or about 250 daltons. The diol chain extender can include any suitable number of carbons. For example, the diol chain extender can include a number-average number of about 2 carbons to about 20 carbons, about 3 carbons to about 10 carbons, or less than, equal to, or greater than about 2 carbons, 3, 4, 5, 6, 7, 8, 9, 10, 11, 12, 13, 14, 15, 16, 17, 18, 19, or 20 carbons. Diol chain extenders such as these can help to strengthen base layer 14. This can be because the relatively short chains can be stiffer than a longer chain diol. The short chain diols can be stiffer, for example, because the short chain diol is more restricted in terms of rotation about the individual bonds along the chain. Examples of suitable diol chain extenders include ethylene glycol, diethylene glycol, triethylene glycol, tetraethylene glycol, propylene glycol, dipropylene glycol, tripropylne glycol, 1,3-propanediol, 1,3-butanediol, 1,4-butanediol, neopentyl glycol, 1,6-hexanediol, 1,4-cyclohexanedimethanol, or a mixture thereof.

The thermoplastic polyurethane can include a hard segment. A hard segment generally refers to harder, less flexible polymer segment, which results from polymerization of the diisocyanate and the diol chain extender. Areas where this polymerization can be identified with C-13 NMR. The hard segment can be in a range of from about 30 wt % to about 55 wt % of the thermoplastic polyurethane film, about 40 wt % to about 55 wt %, or less than, equal to, or greater than about 30 wt %, 31, 32, 33, 34, 35, 36, 37, 38, 39, 40, 41, 42, 43, 44, 45, 46, 47, 48, 49, 50, 51, 52, 53, 54, or 55 wt % of the thermoplastic polyurethane film. Hard segments are present as domains, which can interact with each other to effectively form a crosslink therebetween (e.g., through a hydrogen bond). Under stress for example, through a mechanical deformation, the hard segments can become aligned in the stress direction. This alignment coupled with the hydrogen bonding can contribute to the stiffness, elastomeric resilience, or tear resistance of the thermoplastic polymeric film.

In some examples the reactive mixture can include a crosslinker. Examples of crosslinkers include polyhydroxy group compounds and polyisocyanate compound. For example, the polyhydroxy compounds can include 3 hydroxy groups or 4 hydroxy groups. The polyisocyanate can include 3 cyano groups or 4 cyano groups. While there are many suitable crosslinkers the reactive mixture is free of an aziridine crosslinker. If present, the crosslinkers can function link different thermoplastic polyurethane chains (e.g., intermolecular crosslink). Alternatively, the crosslinkers can function to crosslink different sections of the thermoplastic polyurethane chains (e.g., intramolecular crosslinks).

According to various embodiments, the parylene can include a repeating unit according to Formula VII:

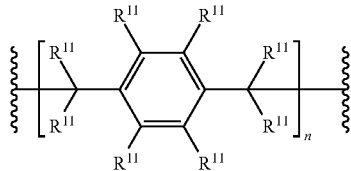

(VII)

wherein at each occurrence, $R^{11}$ is independently chosen from —H, —OH, $NH_2$, or substituted or unsubstituted $(C_1-C_{40})$hydrocarbyl. In further embodiments, $R^1$ and $R^2$ are independently chosen from substituted or unsubstituted $(C_1-C_{40})$alkylene, $(C_2-C_{40})$alkyl, $(C_2-C_{40})$alkenylenyl, $(C_4-C_{20})$aryl, $(C_4-C_{20})$cycloalkyl, and $(C_4-C_{20})$ aralkyl.

In some examples, the second layer 340 is configured such that the working electrode (of the layer 338) is exposed via the window 339.

In some examples, the sensor 334 further includes a third layer 343 comprising a conductive material. The third layer 343 may comprise a reference (e.g., counter-reference) electrode. In some examples, the third layer 343, including the reference (e.g., counter-reference) electrode, comprises a binder material including silver and/or silver chloride that is applied onto the second layer 340 (e.g., an insulator). The binder material can include, for example, a polymer paste, a paint, a polymer-based conducting mixture, an ink, etc.

In some examples, the third layer 343 including the reference electrode is applied as a composite paste including a polymer paste binder material into which is incorporated silver particles and/or silver chloride particles. The composite paste can be applied to the second layer 340. The composite paste may include a polymer, such as, for example, a polyurethane-based polymer.

Particles of silver and silver chloride may be mixed with the paste before the paste is applied to the analyte sensor 334. In some examples, the size of the particles of can be selected to balance electrical conductivity in the reference electrode with available surface area. For example, the polymer may be an electrical insulator. The silver and silver chloride are electrical conductors. Accordingly, individual particles of silver and silver chloride may be independently selected with a size and concentration that allows for suitable physical contact between the particles to allow for electrical conductivity, but also optimize the available surface area. The size of a particle describes a suitable dimension or average dimension of an individual particle. For example, the size of a substantially spherical particle can describe a major diameter of the substantially spherical particle. A size of a substantially non-spherical particle, such as a flake, may describe a major length, width, and/or depth of the particle.

In some examples, the particles of silver are provided as flakes that independently are between about 0.5 microns and 1.5 microns thick and between about 5 microns and 15 microns wide. The average thickness of the silver particles may be independently about 1 micron and the average width is about 10 microns. Also, in some examples, particles of silver chloride are spherical or spheroid independently having a diameter of between 0.5 and 5 microns. The average diameter of silver chloride particles may be independently about 2 microns. It will be appreciated that the particle shapes and sizes for silver and silver chloride in the reference (e.g., counter-reference) electrode material may vary, for example, based on factors such as the binder material that is used, the loading of silver and/or silver chloride, and so on.

The analyte sensor 334 may include two (or more) electrodes, e.g., a working electrode at the layer 338 and exposed at window 339 and at least one additional electrode, such as a reference (e.g., counter-reference) electrode of the layer 343. In the example arrangement of FIGS. 3-5, the reference electrode also functions as a counter electrode, although other arrangements can include a separate counter electrode (See, e.g., FIG. 28). While the analyte sensor 334 may be used with a mounting unit in some examples, in other examples, the analyte sensor 334 may be used with other types of sensor systems. For example, the analyte sensor 334 may be part of a system that includes a battery and sensor in a single package, and may optionally include, for example, a near-field communication (NFC) circuit.

Figure 5:
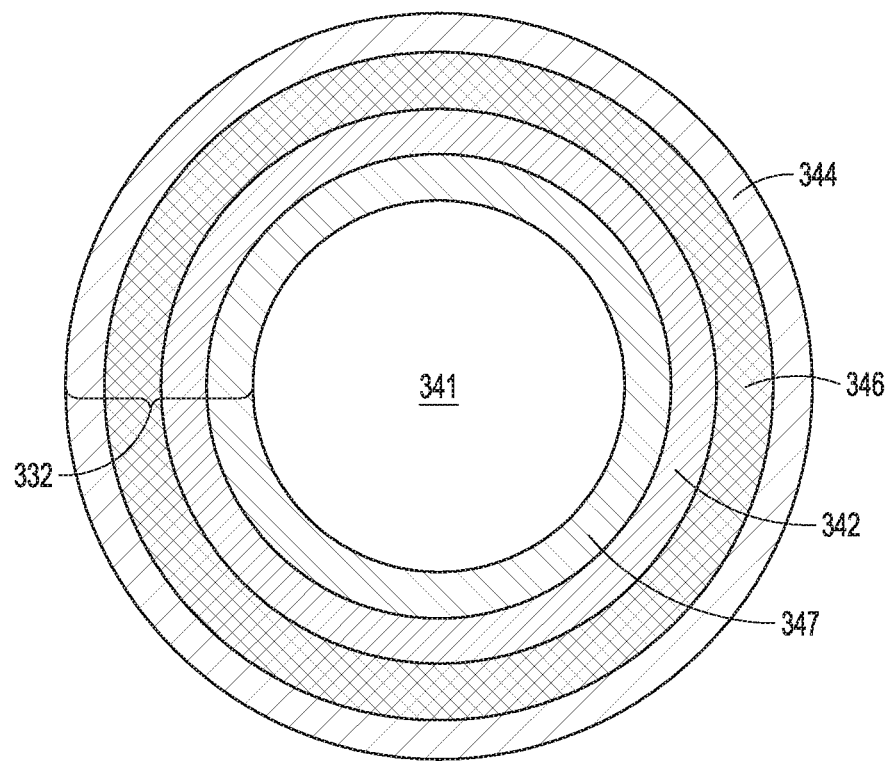
FIG. 5 is a cross-sectional view of the analyte sensor of FIGS. 3 and 4.

FIG. 5 is a cross-sectional view through the sensor 334 of FIG. 4 on plane 2-2 illustrating a membrane system 332. The membrane system 332 may include a number of domains (e.g., layers). In an example, the membrane system 332 may include an enzyme domain 342, a diffusion resistance domain 344, and a bioprotective domain 346 located around the working electrode. In some examples, a unitary diffusion resistance domain and bioprotective domain may be included in the membrane system 332 (e.g., wherein the functionality of both the diffusion resistance domain and bioprotective domain are incorporated into one domain).

The membrane system 332, in some examples, also includes an electrode layer 347. The electrode layer 347 may be arranged to provide an environment between the surfaces of the working electrode and the reference (e.g., counter-reference) electrode that facilitates the electrochemical reaction between the electrodes. For example, the electrode layer 347 may include a coating that maintains a layer of water at the electrochemically reactive surfaces of the sensor 334.

In some examples, the sensor 334 may be configured for short-term implantation (e.g., from about 1 to 30 days). However, it is understood that the membrane system 332 can be modified for use in other devices, for example, by including only one or more of the domains, or additional domains. For example, a membrane system 332 may include a plurality of resistance layers, or a plurality of enzyme layers. In some example, the resistance domain 344 may include a plurality of resistance layers, or the enzyme domain 342 may include a plurality of enzyme layers.

The diffusion resistance domain 344 may include a semi-permeable membrane that controls the flux of oxygen and glucose to the underlying enzyme domain 342. As a result, the upper limit of linearity of glucose measurement is extended to a much higher value than that which is achieved without the diffusion resistance domain 344.

In some examples, the membrane system 332 may include a bioprotective domain 346, also referred to as a domain or biointerface domain, comprising a base polymer. However, the membrane system 332 of some examples can also include a plurality of domains or layers including, for example, an electrode domain, an interference domain, or a cell disruptive domain, such as described in more detail elsewhere herein and in U.S. Pat. Nos. 7,494,465, 8,682,608, and 9,044,199, which are incorporated herein by reference in their entirety.

It is to be understood that sensing membranes modified for other sensors, for example, may include fewer or additional layers. For example, in some examples, the membrane system 332 may comprise one electrode layer, one enzyme layer, and two bioprotective layers, but in other examples, the membrane system 332 may comprise one electrode layer, two enzyme layers, and one bioprotective layer. In some examples, the bioprotective layer may be configured to function as the diffusion resistance domain 344 and control the flux of the analyte (e.g., glucose) to the underlying membrane layers.

In some examples, one or more domains of the sensing membranes may be formed from materials such as silicone, polytetrafluoroethylene, polyethylene-co-tetrafluoroethylene, polyolefin, polyester, polycarbonate, biostable polytetrafluoroethylene, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some examples, the sensing membrane can be deposited on the electroactive surfaces of the electrode material using known thin or thick film techniques (for example, spraying, electro-depositing, dipping, or the like). The sensing membrane located over the working electrode does not have to have the same structure as the sensing membrane located over the reference electrode; for example, the enzyme domain 342 deposited over the working electrode does not necessarily need to be deposited over the reference or counter electrodes.

Although the examples illustrated in FIGS. 4-5 involve circumferentially extending membrane systems, the membranes described herein may be applied to any planar or non-planar surface, for example, the substrate-based sensor structure of U.S. Pat. No. 6,565,509 to Say et al., which is incorporated by reference.

In an example in which the analyte sensor 334 is a glucose sensor, glucose analyte can be detected utilizing glucose oxidase or another suitable enzyme, as described in more detail elsewhere herein. For example, glucose oxidase may react with glucose to product hydrogen peroxide ($H_2O_2$). An oxidation/redox reaction pair as the working and reference electrodes generates a sensor current. The magnitude of the sensor current is indicative of the concentration of hydrogen peroxide, and thereby also indicative of the concentration of glucose.

A calibration curve may be used to generate an estimated glucose concentration level based on the measured sensor current. The magnitude of the sensor current, however, also depends on other factors such as the diffusivity of glucose through the sensor membrane system, the operating potential at the reference electrode, etc. The glucose diffusivity of the membrane system may change over time, which may cause the sensor glucose sensitivity to change over time or "drift." Sensor drift can be compensated, for example, by modeling the sensor drift and making appropriate adjustments to the calibration curve. Changes to the operating potential at the reference (e.g., counter-reference) electrode, described in more detail elsewhere herein, may be mitigated and/or compensated, for example, using the techniques described herein.

Figure 6:
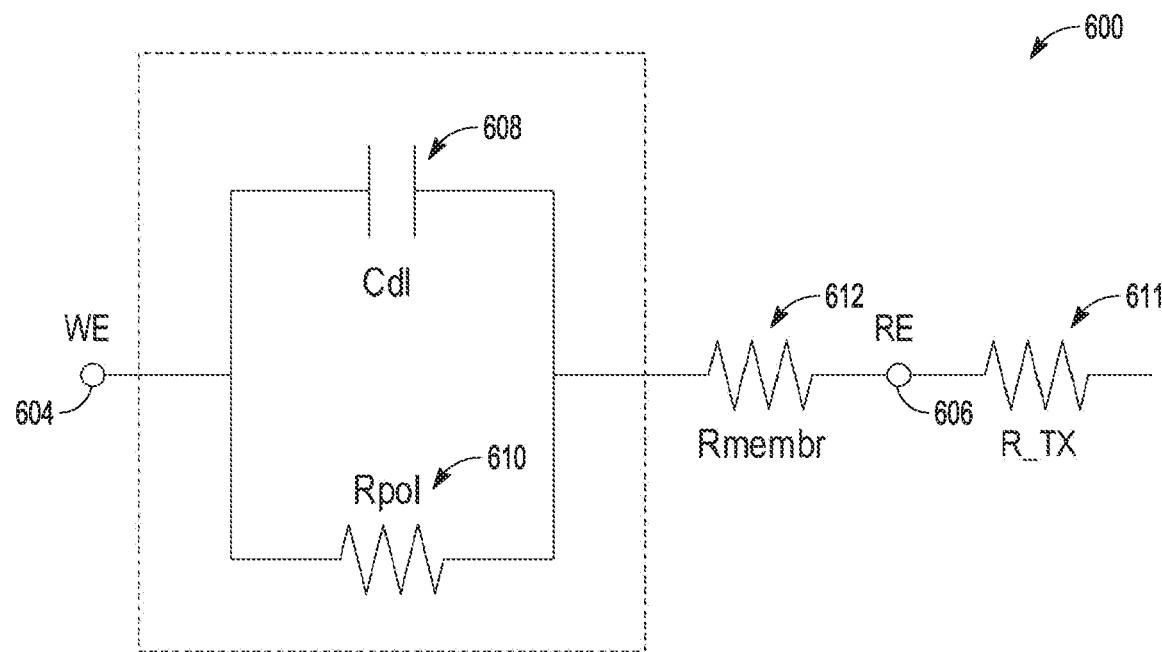
FIG. 6 is a schematic illustration of a circuit that represents the behavior of an example analyte sensor.

FIG. 6 is a schematic illustration of a circuit 600 that represents the behavior of an example analyte sensor, such as the analyte sensor 334 shown in FIGS. 3-5. As described herein, the interaction of hydrogen peroxide (generated from the interaction between glucose analyte and glucose oxidase) and working electrode (WE) 604 produces a voltage differential between the working electrode (WE) 604 and reference (e.g., counter-reference) electrode (RE) 606 which drives a current. The current may make up all or part of a raw sensor signal that is measured by sensor electronics, such as the sensor electronics 106 of FIGS. 1-2, and used to estimate an analyte concentration (e.g., glucose concentration).

The circuit 600 also includes a double-layer capacitance (Cdl) 608, which occurs at an interface between the working electrode (WE) 604 and the adjacent membrane (not shown in FIG. 6, see, e.g., FIGS. 3-5 above). The double-layer capacitance (Cdl) may occur at an interface between the working electrode 604 and the adjacent membrane due to the presence of two layers of ions with opposing polarity, as may occur during application of an applied voltage between the working electrode 604 and reference (e.g., counter-reference) electrode. The equivalent circuit 600 may also include a polarization resistance (Rpol) 610, which may be relatively large, and may be modeled, for example, as a static value (e.g., 100 mega-Ohms), or as a variable quantity that varies as a function of glucose concentration level.

An estimated analyte concentration may be determined from a raw sensor signal based upon a measured current (or charge flow) through the analyte sensor membrane 612 when a bias potential is applied to the sensor circuit 600. For example, sensor electronics or another suitable computing device can use the raw sensor signal and a sensitivity of the sensor, which correlates a detected current flow to a glucose concentration level, to generate the estimated analyte concentration. In some examples, the device also uses a break-in characteristic, as described herein.

The change in glucose diffusivity over time presents a problem, in that two unknown variables (glucose concentration around the membrane 612 and glucose diffusivity in the membrane 612) are present in the system. For example, frequent blood glucose meter calibrations may be used to account for the drift, but this need for meter calibrations may be undesirable for a variety of reasons (e.g., inconvenience to the patient, cost, the potential for inaccurate blood glucose meter data, etc.).

With reference to the equivalent circuit 600, when a voltage is applied across the working and reference (e.g., counter-reference) electrodes 604 and 606, a current may be considered to flow (forward or backward depending on polarity) through the internal electronics of transmitter (represented by R_Tx_internal) 611; through the reference (e.g., counter-reference) electrode (RE) 606 and working electrode (WE) 604, which may be designed to have a relatively low resistance; and through the sensor membrane 612 (Rmembr, which is relatively small). Depending on the state of the circuit, current may also flow through, or into, the relatively large polarization resistance 610 (which is indicated as a fixed resistance, but may also be a variable resistance that varies with the body's glucose level, where a higher glucose level provides a smaller polarization resistance), or into the double-layer capacitance 608 (i.e., to charge the double-layer membrane capacitor formed at the working electrode 604), or both.

The impedance (or conductance) of the membrane (Rmembr) 612 is related to electrolyte mobility in the membrane, which is in turn related to glucose diffusivity in the membrane. As the impedance goes down (i.e., conductance goes up, as electrolyte mobility in the membrane 612 goes up), the glucose sensitivity goes up (i.e., a higher glucose sensitivity means that a particular glucose concentration will produce a larger signal in the form of more current or charge flow). Impedance, glucose diffusivity, and glucose sensitivity are further described in U.S. Patent Publication No. US2012/0262298, which is incorporated by reference in its entirety.

Figure 7:
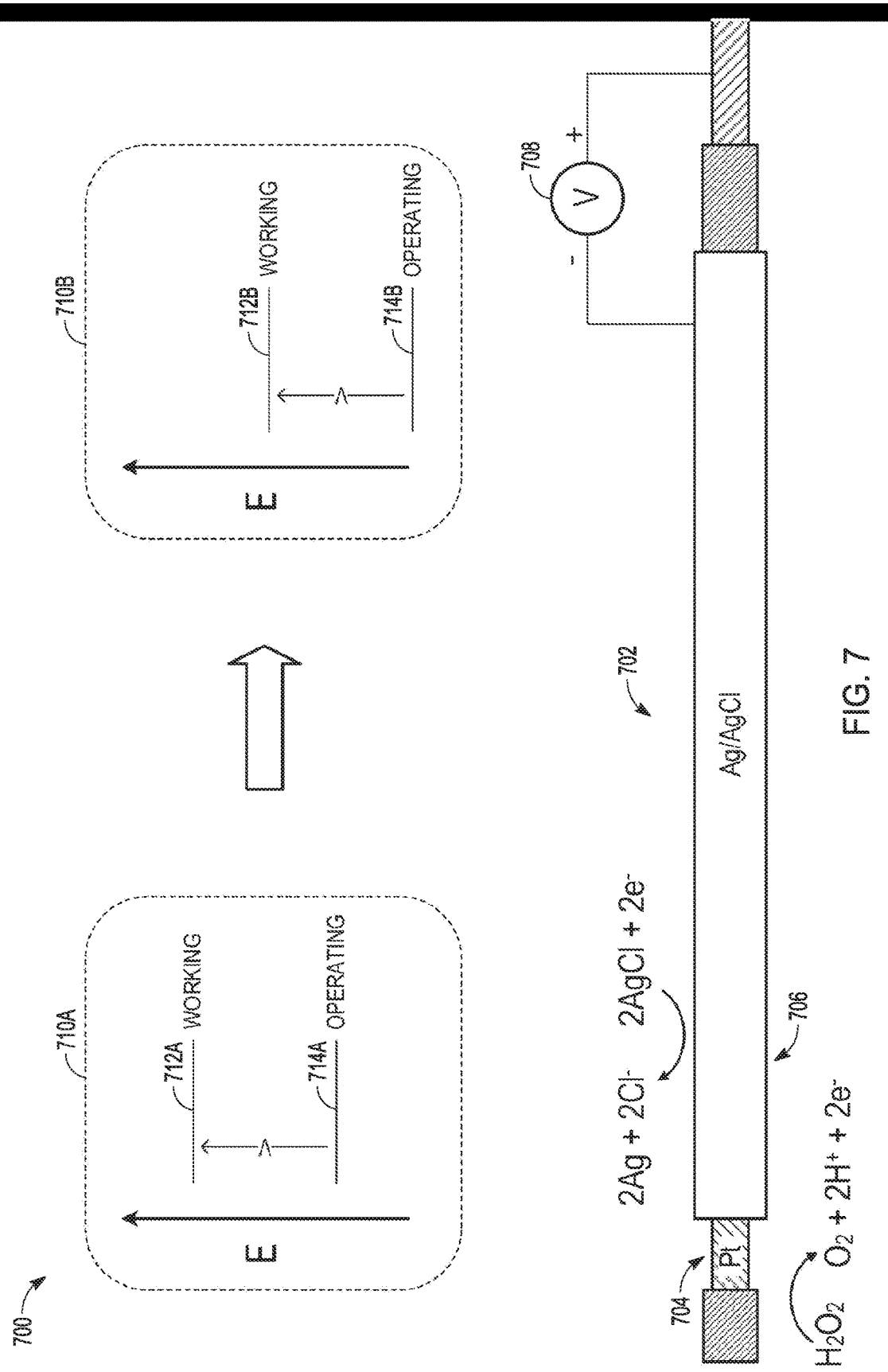
FIG. 7 is a diagram including an example analyte sensor system including a glucose sensor.

FIG. 7 is a diagram including an example analyte sensor system 700 including a glucose sensor 702. The glucose sensor 702 includes a working electrode 704 comprising platinum (Pt) and a reference electrode 706 comprising silver/silver chloride (Ag/AgCl). In some examples, the glucose sensor 702 is arranged in a way similar to that of the analyte sensor 334 of FIGS. 4 and 5.

The glucose sensor 702 may be deployed in conjunction with an enzyme that reacts with glucose, such as glucose oxidase or another suitable enzyme. In some examples, the enzyme is included at an enzyme domain of a membrane system deposited over the glucose sensor 702, similar to the enzyme domain 342 described herein. In examples using glucose oxidase, the glucose oxidase reacts with glucose to produce hydrogen peroxide ($H_2O_2$). As a result, the concentration of hydrogen peroxide at the sensor 702 may be indicative of the concentration of glucose at the sensor 702.

The sensor 702 is configured to generate a sensor current that is indicative of the glucose concentration at least in part with an oxidation/redox reaction pair involving hydrogen peroxide generated from glucose present at the sensor and the enzyme. An oxidation reaction takes place at the working electrode 704. Platinum at the working electrode 704 catalyzes the oxidation of the hydrogen peroxide to produce two protons ($2H^+$), two electrons ($2e^-$) and one molecule of oxygen ($O_2$), as given by [1] below:

$$H_2O_2 \rightarrow O_2 + 2H^+ + 2e^- \quad [1]$$

A corresponding reduction or redox reaction or reactions occur at the reference (e.g., counter-reference) electrode 706. For example, when silver/silver chloride is used at the reference electrode 706, silver chloride reacts with the electrons generated in the oxidation reaction, resulting in two silver atoms (2Ag) and two chloride ions ($2Cl^-$). This reaction is referred to herein as a silver chloride redox reaction. An example silver chloride redox reaction is given by [2] below:

$$2AgCl + 2e^- \rightarrow 2Ag + 2Cl^- \quad [2]$$

The redox reaction drives the reference (e.g., counter-reference) electrode 706 to a operating potential. A voltage source 708 is provided to drive the potential of the working electrode 704 higher than the operating potential by a bias potential, V. For example, the voltage source 708 can be provided by sensor electronics, as described herein.

The voltage diagram 710A shows a operating potential 714A at the reference electrode 706. The potential 712A at the working electrode 704 is higher than the operating potential 714A by the voltage V, as described. This generates the sensor current between the working electrode 704 and the reference electrode 706, where the magnitude of the sensor current is indicative of the glucose concentration at the sensor 702. For example, sensor electronics may apply a calibration curve to the measured sensor current to generate an estimated glucose concentration level based on a measured current.

The magnitude of the sensor current depends on the glucose present at the sensor 702, as described, but can also depend on other factors such as, for example, the operating potential at the reference (e.g., counter-reference) electrode 706. The value of the operating potential at the reference (e.g., counter-reference) electrode 706 is driven by factors such as the concentrations of reactants at the sensor 702, the temperature of the sensor 702, etc. In various examples, the silver chloride redox reaction, such as given by [2], provides a steady operating potential. As the silver chloride of the reference (e.g., counter-reference) electrode 706 is depleted, however, the operating potential may change, for example, dropping to a lower operating potential 714B shown in the voltage diagram 710B. When the operating potential drops, as shown by the voltage diagram 710B, the potential 712B at the working electrode 704 also drops. This can bring about a corresponding drop in the sensor current between the electrodes 704, 706 unrelated to the concentration of glucose, causing a reduction in the sensitivity of the sensor 702, as described in more detail elsewhere herein.

The drop in operating potential at the reference (e.g., counter-reference) electrode 706, in some examples, occurs as the silver chloride redox reaction becomes less dominate at the reference electrode 706 and an electrocatalytic oxygen redox reaction becomes more dominate. An example oxygen redox reaction is given by [3] below:

$$O_2 \rightarrow O_2^{.-} \quad [3]$$

In the oxygen redox reaction, silver (Ag) generated by the silver chloride redox reaction or present in the silver/silver chloride reference electrode 706 catalyzes oxygen molecules ($O_2$) to take on electrons generated by the oxidation reaction at the working electrode 704, resulting, for example, in superoxide radical anion ($O_2^{.-}$), hydroperoxyl radical ($O_2^{.-}$), hydrogen peroxide ($H_2O_2$) or water ($H_2O$). The magnitude of the operating potential change at the reference (e.g., counter-reference electrode) 706 when the oxygen redox reaction is dominant is based on the volume of accessible silver surface area, the oxygen concentration, and the current. For example, lower silver surface area, lower oxygen concentration, and higher sensor current correspond to lower operating potentials. When the sensor 702 is used in vivo, the oxygen redox reaction, such as the one given by [3] above, operates at a lower potential than the chloride redox reaction. This may cause the drop in operating potential shown by the voltage diagrams 710A, 710B.

In use, glucose sensors, such as the glucose sensor 702, tend to suffer a reduction in the sensitivity over time. This effect can be referred to as Progressive Sensitivity Decline (PSD). As described herein, the sensitivity of the sensor 702 describes the magnitude of sensor current generated in the presence of a given quantity of glucose. Consider an example in which the sensor 702 generates a sensor current with a magnitude of X nanoamps when the sensor 702 is in the presence of a glucose concentration of Y mg/dL. An increase in the sensitivity of the sensor 702 would cause the sensor 702 to generate greater than X nanoamps at a glucose concentration Y mg/dL. A decrease in the sensitivity of the sensor 702 would cause the sensor to generate less than X nanoamps at a glucose concentration of Y mg/dL. When sensitivity declines below a usable level, the sensor 702 may no longer be useful. This can be referred to as the sensors End-of-Life (EOL).

Sensitivity decline leading to sensor EOL can be caused, at least in part, by the reduction in operating potential at the reference (e.g., counter-reference) electrode 706 as silver chloride is depleted and oxygen redox becomes dominant over silver chloride redox. For example, the reduction in operating potential may lead to a mismatch between the applied potential V at the working electrode 704 and the potential required for the hydrogen peroxide oxidation reaction at the working electrode 704. Referring again to the voltage diagrams 710A, 710B, if the lower potential 712B at the working electrode 704 approaches or is lower than the operating potential of the hydrogen peroxide oxidation reaction, then the hydrogen peroxide oxidation reaction at the working electrode 704 may slow down or cease, leading to a reduction in sensitivity that can lead to EOL.

Figure 8:
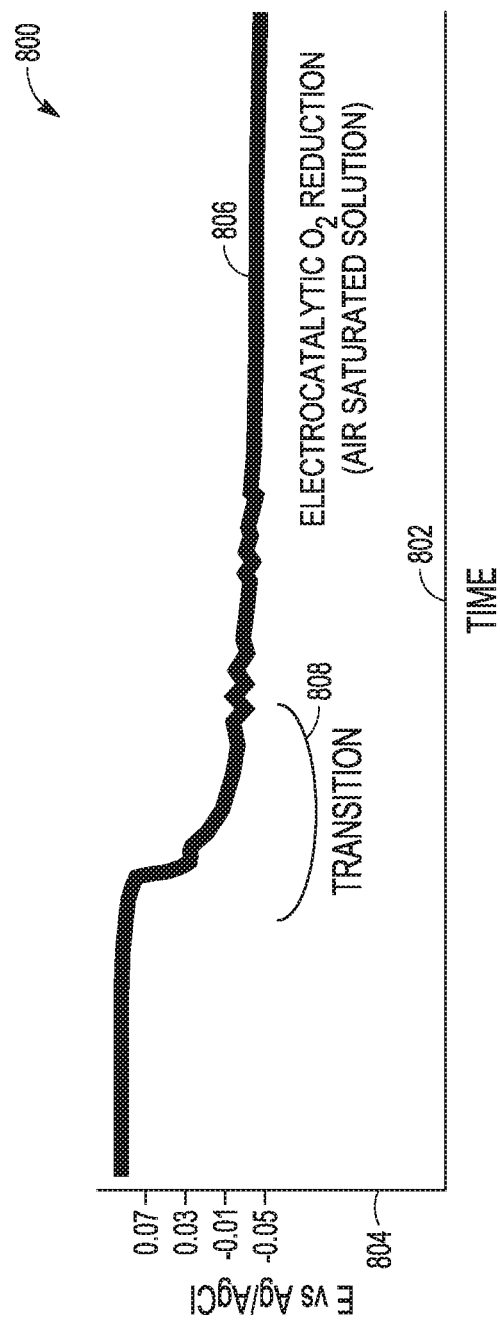
FIG. 8 is a diagram illustrating a change in operating potential at the reference electrode.

FIG. 8 is a diagram 800 illustrating a change in operating potential as the silver chloride at the reference electrode 706 is depleted and the oxygen redox reaction becomes dominant. In the diagram 800, a horizontal axis 802 indicates time and a vertical axis 804 indicates the operating potential at the reference electrode 706. Prior to a transition period 808, the silver chloride redox reaction is dominant. The operating potential, in the example of FIG. 8, is about 0.07 V, although other operating potentials are possible depending the operating conditions of the sensor 702. During the transition period 808, the oxygen redox reaction becomes more dominant. For example, the amount of available silver chloride at the reference electrode 706 may be reduced, reducing the silver chloride redox reaction and thereby increasing the dominance of the oxygen redox reaction. After the transition period 808, the available silver chloride may be depleted, reducing the silver chloride redox reaction and driving the reference potential to the potential associated with the oxygen redox reaction. In some examples, the potential associated with the oxygen redox reaction is low enough to drop the operating potential at the working electrode 704 to a level that does not support or fails to support sufficient oxidation of hydrogen peroxide, thus reducing the sensitivity of the sensor 702.

As described herein, the drop in operating potential from silver chloride redox to oxygen redox is observed when the oxygen redox reaction occurs at a lower potential than the silver chloride redox reaction. The lower operating potential for the oxygen redox reaction may be related, at least in part, to the effectiveness of silver as a catalyst for that reaction. The operation of the sensor 702 may provide sufficient oxygen such that mass transport or availability of oxygen does not limit oxygen redox at the reference electrode 706. For example, as described above, glucose may react with an enzyme and oxygen, as described herein, to generate hydrogen peroxide. The hydrogen peroxide is oxidized at the working electrode 704 to generate oxygen, as shown by [1] above. The amount of oxygen consumed by oxygen redox at the reference electrode 706 may be less than or equal to the amount of hydrogen peroxide consumed by hydrogen peroxide oxidation at the working electrode 704. Accordingly, the lower potential of the oxygen redox reaction relative to the potential of the silver chloride reaction may result more from sluggish kinetics than from any lack of available of oxygen.

When sufficient oxygen is present, sluggish kinetics for the oxygen redox reaction, in some examples, is due to the properties of silver as a catalyst. For example, although silver does catalyze oxygen redox, it may not be as effective as other catalysts. For a given level of accessible catalyst surface area, oxygen concentration, and sensor current density, a silver-catalyzed oxygen redox reaction may exhibit sluggish kinetics, and therefore a lower operating potential, than oxygen redox reactions using other catalysts. Various examples described herein are directed to glucose sensors that incorporate a non-silver catalyst material at the reference (e.g., counter-reference) electrode to replace and/or supplement silver for catalyzing oxygen redox at the reference electrode 706. In some examples, the non-silver catalyst material catalyzes an oxygen redox reaction alone. Also, in some examples, the non-silver catalyst material acts as a mediator to catalyze the oxygen redox reaction in conjunction with silver. The non-silver catalyst material, alone or in conjunction with silver, catalyzes oxygen redox at a higher potential than silver or silver alone. This leads to a higher operating potential at the reference (e.g., counter-reference) electrode 706 after oxygen redox becomes dominant. The higher operating potential may be high enough to keep the potential at the working electrode 704 above or near enough the operating potential of the hydrogen peroxide oxidation so as to maintain sensitivity at an acceptable level for a longer time.

In some examples, the non-silver catalyst material at the reference (e.g., counter-reference) electrode 706 includes an oxygen redox reaction mediator material. The mediator material operates in conjunction with silver to catalyze oxygen redox at a higher potential than silver alone. For example, the mediator material may be selected to accept electrons from silver already present at the reference (e.g., counter-reference) electrode 706 (e.g., from manufacture and/or as the product of the silver chloride redox reaction). The mediator material may also be selected to transfer the received electrons to oxygen more effectively than silver, improving the catalyzation of oxygen redox as described herein.

Example mediator materials that can be included at the reference electrode 706 of a glucose sensor include quinone-derivatives. A quinone or quinone derivative can be understood to refer to a class of organic compounds that include a six carbon cyclic dione structure including two double-bonds. Examples of quinone derivatives include anthraquinone, chloranil, 1,4-benzoquinone, 2-bromoanthraquinone, quinhydrone, 2,6-dibromoanthraquinone, 1,4-dihydroxyanthraquinone, 1,4-diamino anthraquinone, 2-aminoanthraquinone, 2-chloroanthraquinone, 1-chloro anthraquinone, 5-iodoisatin, 1-amino anthraquinone, 1,5-diaminoanthraquinone, 2,5-dibromo-1,4-benzoquinone, 1-amino anthraquinone, 1,5-diaminoanthraquinone, 2-hydroxyanthraquinone, 2,7-dibromo-9,10-phenanthrenedione, tetrahydroxyquinone, and 2-ethyl-anthroquinone (AQN). AQN is a water insoluble quinone derivative. AQN, or another suitable quinone derivative, can act as a mediator for oxygen redox. For example, AQN can accept electrons from the silver already present at the reference electrode. The AQN, however, transfers the received electrons to oxygen more effectively than silver. For this reason, the combination of silver with AQN or another suitable quinone derivative compound may be a more effective catalyst of oxygen redox than silver alone. This can lead to increased kinetics and an increased operating potential relative to oxygen redox that is catalyzed by silver alone.

Figure 9:
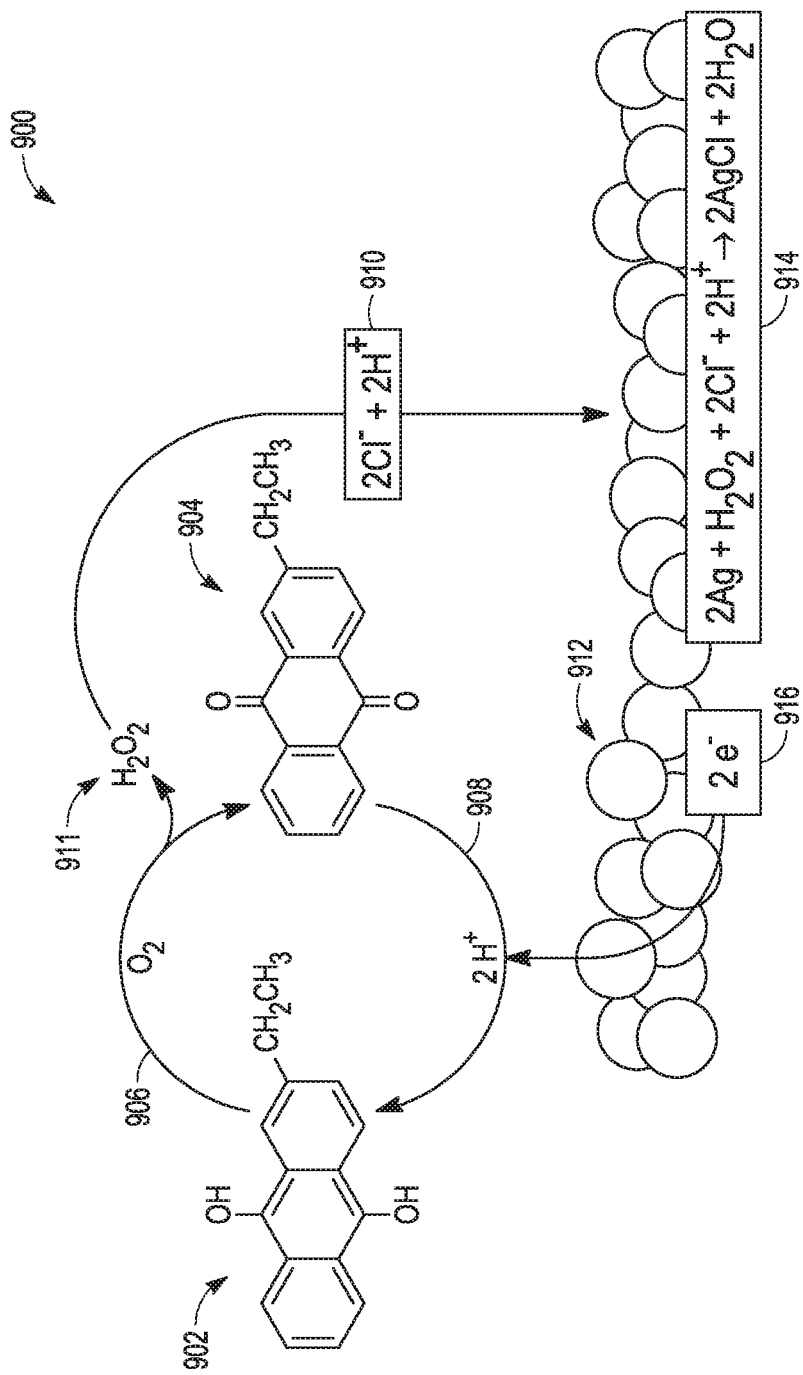
FIG. 9 is a diagram describing the behavior of 2-Ethylanthroquinone (AQN) at the reference electrode of a glucose sensor, such as the glucose sensor of FIG. 7.

In some examples, AQN or another suitable quinone derivative, prompts an electrocatalytic cycle at the reference electrode. The electrocatalytic cycle may tend to mediate oxygen redox, as described, and can also regenerate silver chloride at the reference electrode 706. FIG. 9 is a diagram 900 describing the behavior of AQN 904 at the reference electrode 706 of a glucose sensor, such as the glucose sensor 702 of FIG. 7. When the operating potential at the reference (e.g., counter-reference) electrode drops below a redox potential of the AQN 904, the AQN 904 undergoes an outer-sphere redox at reaction 908 to generate 2-ethyl-anthroquinol ($H_2AQN$) 902. The $H_2AQN$ 902 generated at reaction 908 reacts with oxygen ($O_2$) at reaction 906 to produce hydrogen peroxide ($H_2O_2$) 911 and regenerate the AQN 904. At least some of the hydrogen peroxide 911, at reaction 914, re-oxidizes silver 912 at the reference electrode 706 in the presence of a chloride ion and proton 910 to regenerate silver chloride with water as a byproduct. Regenerated silver chloride may support the silver chloride redox reaction, which may also tend to increase the operating potential, as described herein.

The catalytic cycle shown in FIG. 9 may turn on and off when the operating potential drops crosses the redox potential of the AQN 904. For example, when the operating potential drops below the relevant redox potential, the catalytic cycle is turned on. Reaction 908 occurs, generating $H_2AQN$ 902 and two electrons 916, which may tend to mediate oxygen redox. The redox potential of the AQN, in some examples, is between about 0.02 V and about 0.155 V. The $H_2AQN$ 902 reacts back to AQN 904 at reaction 906. This electrolytic cycle is turned off when the operating potential rises above the relevant redox potential. When this occurs, reaction 908 may cease. Reaction 906 may continue to occur until previously-generated $H_2AQN$ 902 is exhausted. In some examples, when the catalytic cycle of FIG. 9 is turned off, the AQN 904 or other quinone derivative exists at the reference electrode 706 in oxidized form and may not interfere with other aspects of sensor performance.

In various examples, the redox potential of the AQN 904 or other quinone derivative can be tuned to select when the catalytic cycle of FIG. 9 is turned on an off. For example, the redox potential of AQN 904 can be tuned chemically by changing the substituents attached to the anthracene backbone of the AQN 904. A quinone, also referred to as a quinone derivative, can be understood to refer to a class of organic compounds that include a six carbon cyclic dione structure including two double-bonds. An example of a quinone derivative is represented as Formula VIII:

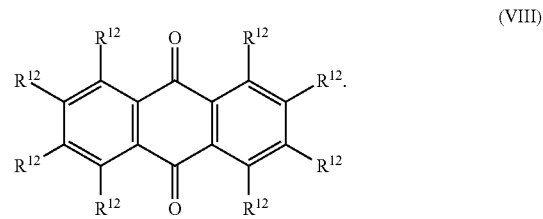

(VIII)

In Formula VIII, at each occurrence $R^{12}$ is independently chosen from —H, —$NH_2$, —$NR^{13}$, —OH, -halo, —$NO_3$, or substituted or unsubstituted ($C_1$-$C_{40}$)hydrocarbyl. $R^{13}$ is substituted or unsubstituted ($C_1$-$C_{40}$)hydrocarbyl. In further embodiments, $R^{12}$ and $R^{13}$ are independently chosen from substituted or unsubstituted ($C_1$-$C_{40}$)alkylene, ($C_2$-$C_{40}$)alkylene, ($C_2$-$C_{40}$)alkenylene, ($C_4$-$C_{20}$)arylene, ($C_4$-$C_{20}$)cycloalkylene, and ($C_4$-$C_{20}$) aralkylene, ($C_2$-$C_{40}$)haloalkyl, or ($C_2$-$C_{40}$)alkoxyl.

Examples of quinone derivatives include anthraquinone, chloranil, 1,4-benzoquinone, 2-bromoanthraquinone, quinhydrone, 2,6-dibromoanthraquinone, 1,4-dihydroxyanthraquinone, 1,4-diamino anthraquinone, 2-aminoanthraquinone, 2-chloroanthraquinone, 1-chloro anthraquinone, 5-iodoisatin, 1-amino anthraquinone, 1,5-diaminoanthraquinone, 2,5-dibromo-1,4-benzoquinone, 1-amino anthraquinone, 1,5-diaminoanthraquinone, 2-hydroxyanthraquinone, 2,7-dibromo-9,10-phenanthrenedione, tetrahydroxyquinone, and 2-ethyl-anthroquinone (AQN). The redox potential selected for the AQN or other quinone derivative can be selected above an operating potential at which the sensitivity of the sensor 702 declines and the sensor 702 is be no longer useful. For example, the redox potential selected for the AQN may be selected such that the sum of the redox potential for the AQN and the bias potential V is near to or greater than the operating potential of the hydrogen peroxide oxidation at the working electrode 704 such that the sensitivity of the sensor 702 remains at an acceptable level.

Figure 10:
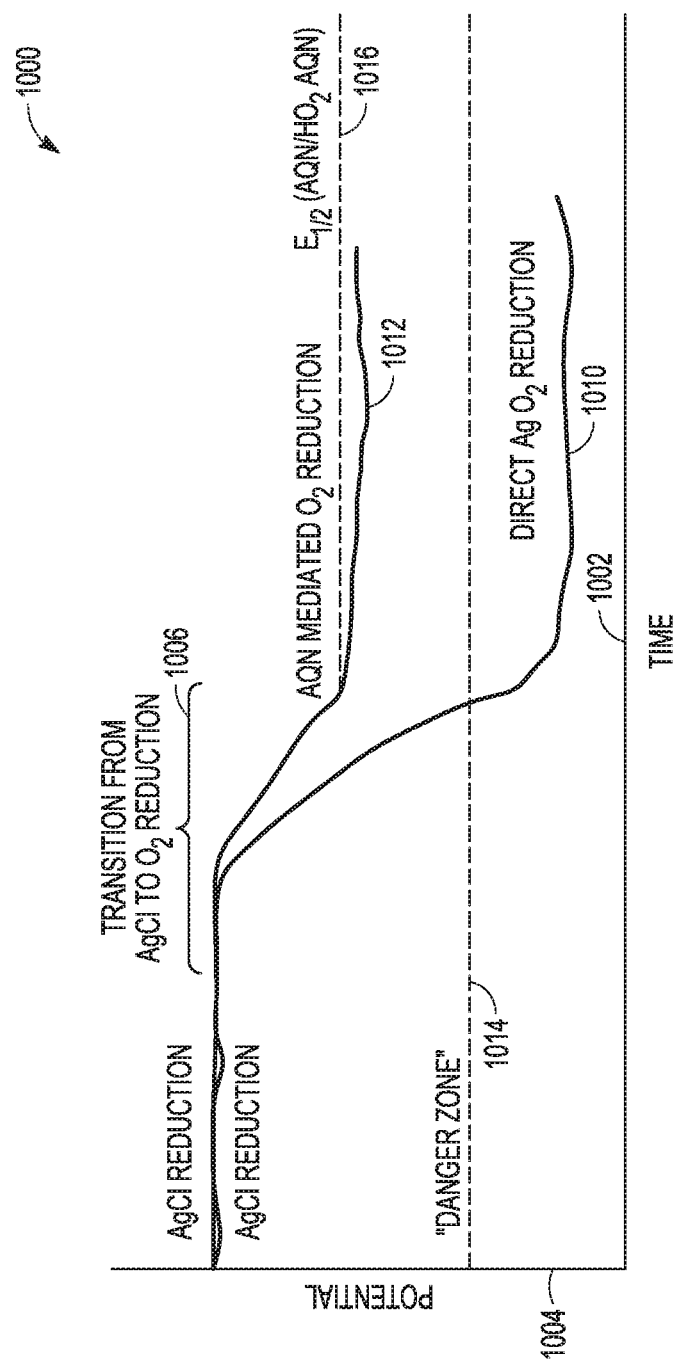
FIG. 10 is a diagram showing one example the operating potential of a reference electrode including a quinone-derivative, as described herein.

FIG. 10 is a diagram 1000 showing one example the operating potential of a reference electrode 706 including a quinone-derivative, as described herein. The diagram 1000 includes a horizontal axis 1002 indicating time and a vertical axis 1004 indicating operating potential (e.g., a potential at the reference electrode 706). A transition from silver chloride redox to oxygen redox is shown by bracket 1006. A first curve 1010 shows the response of the sensor 702 without a quinone derivative. As shown, the operating potential drops off during a transition period until direct silver-catalyzed oxygen redox is dominant. At this point, the operating potential is below a threshold potential 1014 indicating a potentially significant loss of sensor sensitivity. For example, the threshold potential 1014 may indicate the operating potential at which the sum of the operating potential and the bias potential is less than the operating potential of the hydrogen peroxide oxidation at the working electrode 704.

A second curve 1012 shows the response of the sensor 702 with a quinone derivative present. As shown, the quinone mediated oxygen redox is at a potential 1016 that is higher than the potential of the direct silver oxygen redox shown by the curve 1010 and may also be above the threshold level 1014 such that the sensor 702 continues to have a usable sensitivity after the depletion of silver chloride. In some examples, the difference between the potential 1018 and the potential 1014 is about 50 mV.

A quinone derivative may be incorporated into the reference (e.g., counter-reference electrode) 706 in any suitable manner. In some examples, the quinone derivative is incorporated into a coating that is applied to the reference (e.g., counter-reference) electrode 706. For example, the quinone derivative can be incorporated into a membrane domain, such as one or more of the domains of the membrane system 332 of FIG. 5. The selected membrane domain including the quinone derivative, in some examples, is in contact with the reference (e.g., counter-reference) electrode 706. In some examples, a quinone derivative is incorporated into the reference (e.g., counter-reference) electrode 706 itself. For example, referring to the example of FIG. 4, the quinone derivative may be incorporated into a paste, ink, or other material applied to generate the enzyme domain 342.

Other quinone derivatives that may be used to mediate oxygen redox in addition to or instead of AQN may include, for example, ubiquinone, 1-napthaquinone, 4-napthaquinone, etc. Also, in some examples, a quinone derivative can be supplemented and/or replaced with other alternative oxygen redox mediators. Such alternative oxygen redox mediators may include transition metal porphyrins such as iron-porphyrins as well as salens, or lactams. Other suitable oxygen redox mediators that can be used include, nitroxyl species such as TEMPO (2,2,6,6-tetramethylpiperdin-1-yl) or ABNO (9-azaicyclo[3.3.1]nonane N-oxyl). Still other suitable oxygen redox mediators include 1,2-substituted hydrazines such as 1,2-diphenylhydrazine or other hydrazines. These and other suitable oxygen redox catalysts may behave similar to quinone derivatives. For some catalysts, however, the reduction of oxygen (reaction 906 in FIG. 9) may bypass hydrogen peroxide and be reduced directly to water.

Also, in some examples, the reference electrode can include a non-silver catalyst material that is a direct catalyst of oxygen redox. The direct catalyst can be included in addition to or instead of mediator materials such as the quinone derivatives described herein. Example direct catalyst materials can include heterogeneous materials, such as catalysts including platinum or platinum alone. Examples of catalysts including platinum include (2,2'-bipyridine)dichloroplatinum(ii), cis-bis(acetonitrile)dichloroplatinum(ii), cis-bis(benzonitrile)dichloroplatinum(ii), bis(tri-tert-butylphosphine)platinum(0), (1,5-cyclooctadiene)dimethylplatinum (ii), cis-dichlorobis(diethyl sulfide)platinum(ii), cis-dichlorobis(dimethyl sulfoxide)platinum(ii), cis-dichlorobis(pyridine)platinum(ii), cis-dichlorobis(triethylphosphine) platinum(ii), cis-dichlorobis(triphenylphosphine)platinum (ii), trans-dichlorobis(triphenylphosphine)platinum(ii), dichloro(1,5-cyclooctadiene)platinum(ii), dichloro(1,2-diaminocyclohexane)platinum(ii), dichloro(dicyclopentadienyl)platinum(ii), dichloro(ethylenediamine)platinum(ii), dichloro(norbornadiene)platinum(ii), dichloro(1,10-phenanthroline)platinum(ii), ethylenebis(triphenylphosphine)platinum(0), (ethylenediamine)iodoplatinum(ii) dimer dinitrate, platinum(ii) acetylacetonate, or combinations thereof.

The selected direct catalyst material may be a better oxygen redox catalyst than silver, which may increase the kinetics and also the electrical potential of the oxidation redox reaction. As a result, the operating potential at the reference electrode 706 may remain higher after the oxygen redox reaction becomes dominant.

Consider an example in which platinum catalyst is added. The platinum catalyst may catalyze a redox reaction of oxygen to water at the thermodynamic potential of the sensor 702, for example, as given by [4] below:

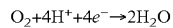

$$O_2 + 4H^+ + 4e^- \rightarrow 2H_2O \qquad [4]$$

The oxygen redox reaction of [4] may operate, in presence of the platinum, at a potential higher than the potential of the silver-catalyzed oxygen redox reaction described above. In arrangements where the primary catalyst for oxygen redox is silver, oxygen redox may begin after silver chloride is depleted such that the operating potential at the reference electrode drops by more than a threshold amount (e.g., about 10 mV). On the other hand, oxygen redox catalyzed by platinum, such as given by [4] above, can begin at higher operating potentials while silver chloride redox is occurring. This may result in a fraction of the current at the reference electrode being driven by platinum-catalyzed oxygen redox while the remaining current is driven by silver chloride redox. Because the silver chloride redox may not be driving all of the reference electrode current, its capacity may be increased.

Figure 11:
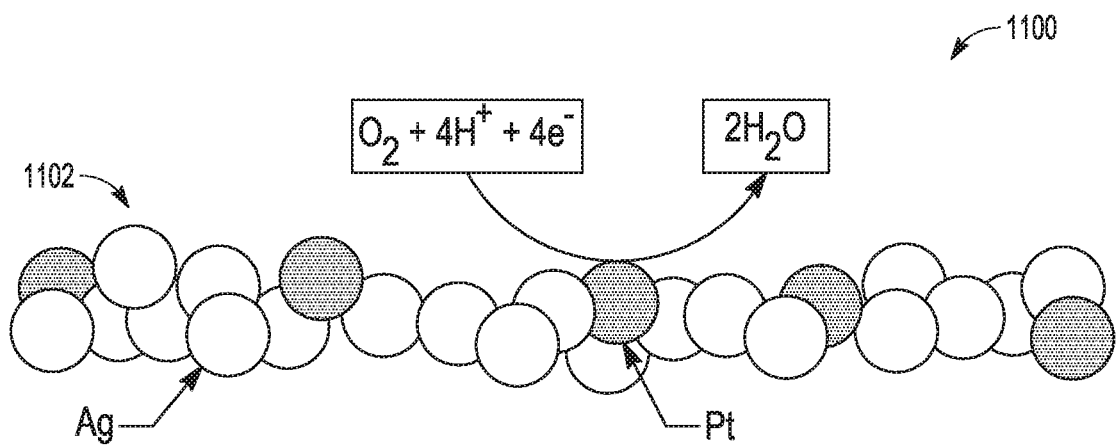
FIG. 11 is a diagram showing a surface of a reference electrode including silver (Ag) and platinum (Pt) catalyzing an oxygen redox reaction.

FIG. 11 is a diagram 1100 showing a surface 1102 of a reference electrode including silver (Ag) and platinum (Pt) catalyzing the oxygen redox reaction given by [4] above. The surface 1102 is heterogeneous, with platinum (Pt) particles interspersed with the existing silver (Ag).

There are a number of different ways that platinum can be incorporated at the reference electrode 706. In some, examples, platinum particles are added to a binder material, such as a polymer paste, polymer-based conducting mixture, ink, paint, or other material applied to the sensor 702 to form the reference electrode 706. The platinum particle may be incorporated into the binder material in the same manner that silver and silver chloride particles are incorporated. In some examples, the platinum particles make up between about 1% and 20% of the metal volume added to the binder material, where the metal volume includes the sum of the volumes of platinum, silver, and silver chloride. In some examples, the platinum particles may be about the same size as the silver and silver chloride particles. For example, the platinum particles may have monomodal size distribution in which an average size of between about 0.4 microns and about 5 microns or, in some examples, between about 0.8 microns and 2.5 microns. In some examples, a median size of about 50% of the individual platinum particles (D50) is about 0.4 microns and about 5 microns, or in some examples about 0.8 microns and 2.5 microns. In some examples, a median size of about 98% of the individual platinum particles (98) is about 0.4 microns and about 5 microns, or in some examples about 0.8 microns and 2.5 microns. In some examples, the size of any individual platinum particle does not exceed 5 microns.

In other examples, platinum is deposited onto surfaces of the particles of silver and/or silver chloride. The silver and/or silver chloride particles with platinum deposits are then incorporated into the reference electrode 706, for example, using a binder material as described herein. In some examples, electrochemical deposition is used to deposit platinum onto existing particles of silver and/or silver chloride. An average size of individual platinum deposits on the silver and/or silver chloride particles may have an average diameter of between about 50 and 200 times smaller than the average diameter of the silver and/or silver chloride particles. For example, when silver chloride particles are provided as spherical and/or spheroid particles having a diameter of between 2.5 and 10 microns, platinum deposits on the silver chloride particles may have a size of between about 12.5 nanometers and 200 nanometers. In some examples, a median size of about 50% of the individual silver chloride particles (D50) is about 2.5 microns and about 10 microns, or in some examples about 12.5 nanometers and 200 nanometers. In some examples, a median size of about 98% of the individual silver chloride particles (98) is about 2.5 microns and about 10 microns, or in some examples about 12.5 nanometers and 200 nanometers.

Similarly, in examples in which silver is provided including flakes with an average thickness of between about 0.5 microns and about 1.5 microns and an average width of between about 5 microns and about 15 microns, platinum deposits on the silver particles may have a size of between about 25 nanometers and 300 nanometers. In some examples, a median thickness of about 50% of the individual silver flakes (D50) is about 0.5 microns and about 1.5 microns. In some examples, a median thickness of about 98% of the individual silver flakes (D98) is about 0.5 microns and about 1.5 microns. In some examples, a median width of about 50% of the individual silver flakes (D50) is about 5 microns and about 15 microns. In some examples, a median width of about 98% of the individual silver flakes (98) is about 5 microns and about 15 microns. In some examples, a median size of about 50% of the platinum deposits (D50) is about 25 nanometers and about 300 nanometers. In some examples, a median size of about 98% of the platinum deposits (98) is about 25 nanometers and about 300 nanometers.

In some examples, platinum deposits on silver and/or silver chloride particles have a size of, for example, between about 50 nanometers and about 200 nanometers. In some examples, the diameter platinum deposits may have a size of about 100 nanometers. In some examples, a median size of about 50% of the individual platinum deposits (D50) is about 50 nanometers and about 200 nanometers. In some examples, a median size of about 98% of the individual platinum deposits (98) is about 50 nanometers and about 200 nanometers.

In some examples, in addition to or instead of depositing platinum onto particles of silver or silver chloride, nanoparticles of platinum may be incorporated into the binder material. The nanoparticles may have an average size that is between 50 and 200 times smaller than the average diameters of the silver particles and/or silver chloride particles. In some examples, the platinum nanoparticles have an average size of, for example, between about 50 nanometers and about 200 nanometers. In some examples, the platinum nanoparticles have an average size of about 100 nanometers.

In some examples, degradations in the operating potential can be caused, at least in part by fouling at the reference (e.g., counter-reference) electrode. For example, the operation of the sensor 702 may tend to cause the pH around the reference electrode 706 to increase. The increase in pH around the reference electrode 706 can cause calcium present at the interstitial fluid around the sensor 702 to come out of solution and precipitate on the reference electrode 706 as calcium carbonate. Calcium carbonate deposits on the reference electrode 706 may cover available silver chloride, silver, and/or other non-silver catalyst material at the reference electrode 706. This makes the covered silver chloride, silver, and/or other non-silver catalyst material unavailable for reacting or catalyzing reactions. This reduces the effective loading of the reference (e.g., counter-reference) electrode 706 and may cause premature EOL at the sensor 702.

Various examples address this and other problems by including an anti-mineralization agent at the reference electrode. The anti-mineralization agent reduces the formation of calcium carbonate at the reference electrode. This may reduce or prevent calcium carbonate precipitation at the reference electrode 706, keeping more of the silver, silver chloride, and/or other non-silver catalyst available for redox at the reference electrode 706 and thereby increasing the life of the reference electrode 706 and sensor 702.

The anti-mineralization agent, in some examples, is incorporated into a binder material, such as a polymer paste, polymer-based conducting mixture, ink, and/or paint that also includes silver, silver chloride and, optionally, a non-silver catalyst material as described herein. In some examples, an anti-mineralization agent is incorporated into a membrane system for the sensor 702, for example, similar to the membrane system 332 described herein with respect to FIGS. 4 and 5. For example, an anti-mineralization layer including the anti-mineralization agent can be positioned at the reference electrode 706. For example, the anti-mineralization agent can be positioned over more than half of the reference electrode 706 or, in some examples, over substantially all of the reference electrode.

Any suitable anti-mineralization agent may be used. In some examples, the anti-mineralization agent comprises a polyacrylate acid. For example, a polyacrylate acid can be incorporated into a solution. The glucose sensor 702 can be dipped into the solution, for example, as described herein, to coat at least the reference electrode 706 with the polyacrylate acid. For example, the polyacrylate acid may form part or all of a membrane system positioned at the reference electrode 706. Other example anti-mineralization agents include carboxylate-containing polymers, such as poly (maleate), polysulfonate, and polyphosphonate.

Where present the polyacrylic acid may be a homopolymer or copolymer including the repeating unit according to Formula IX.

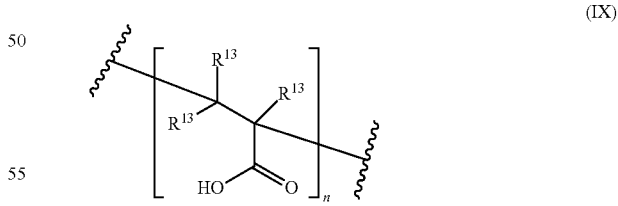

(IX)

wherein at each occurrence, $R^{13}$ is independently chosen from —H or substituted or unsubstituted $(C_1-C_{40})$hydrocarbyl. In further at each occurrence embodiments, $R^{13}$ is independently chosen from substituted or unsubstituted $(C_1-C_{40})$alkyl, $(C_2-C_{40})$alkyl, $(C_2-C_{40})$alkenylenyl, $(C_4-C_{20})$ aryl, $(C_4-C_{20})$cycloalkyl, and $(C_4-C_{20})$ aralkyl. According to further embodiments, the polyacrylic acid may be a homopolymer or copolymer including the repeating unit according to Formula X.

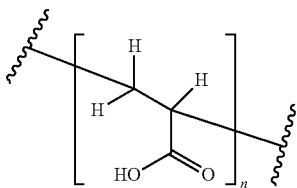

(X)

Figure 12:
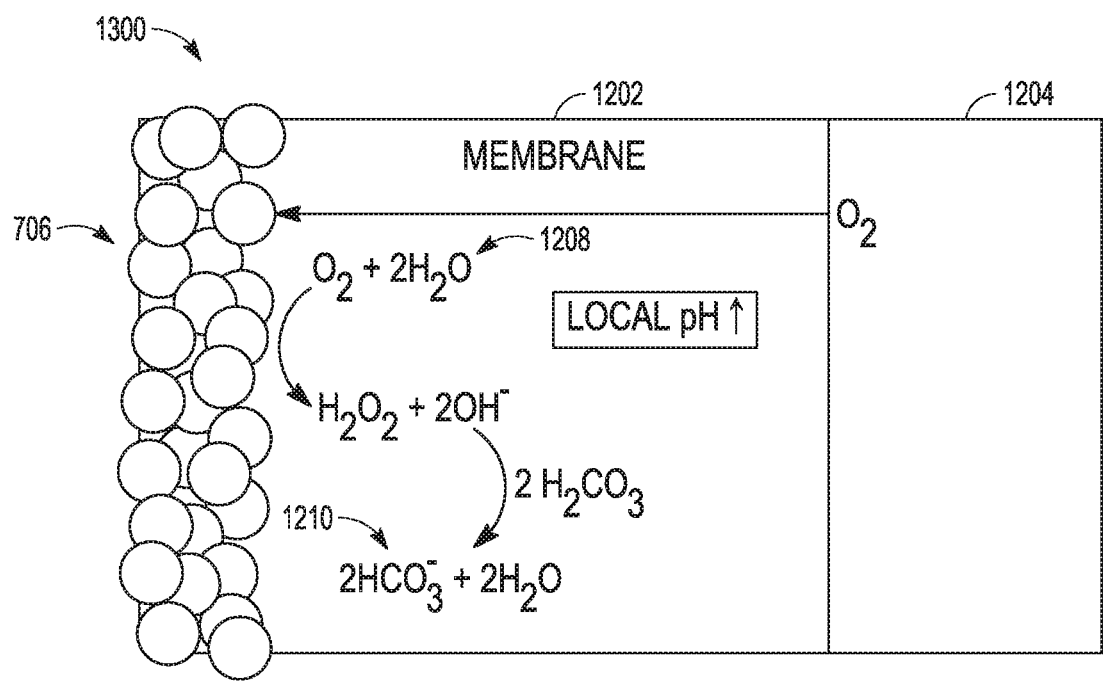
FIG. 12 shows a diagram illustrating an example slice of the reference electrode, an associated membrane system, and interstitial fluid demonstrating how operation of the reference electrode cause the pH to rise in an in vivo environment.

FIG. 12 shows a diagram 1200 illustrating an example slice of the reference electrode 706, an associated membrane system 1202, and interstitial fluid 1204 demonstrating how operation of the reference electrode 706 cause the pH to rise in an in vivo environment. In the diagram 1200 the reference (e.g., counter-reference electrode) 706 includes silver (Ag). For example, the diagram 1200 may depict the reference electrode 706 after available silver chloride is depleted.

As shown, oxygen 1206 from the interstitial fluid 1204 diffuses through the membrane system 1202 to the reference electrode 706. The oxygen 1206 undergoes an oxygen redox reaction 1208 catalyzed by the silver of the reference electrode 706. The reactants of the oxygen redox reaction 1208 include oxygen and protons ($H^+$). The products of the oxygen redox reaction 1208 include hydrogen peroxide and/or water and hydroxide ions ($OH^-$).

The oxygen redox 1208 may tend to increase the pH at the reference electrode 706. In some examples, this is at least partially offset by the oxidation at the working electrode 704 (not shown in FIG. 12), which tends to decrease pH. Carbonic acid buffering from the interstitial fluid 1204, in some examples, causes the pH raising action of the oxygen redox reaction to drive the total pH up. For example, the primary buffer in interstitial fluid 1204 may be carbonic acid ($H_2CO_3/HCO_3^-$). Carbonic acid may react with the hydroxide ions generated by oxygen redox reaction 1208 at reaction 1210 to generate bicarbonate ions ($HCO_3$) and water.

Although the $pK_a$ of carbonic acid is about 3.6, that $pK_a$ can increase based on the pre-equilibrium hydration of dissolved carbon dioxide ($CO_2$) in solution, which can shift the effective $pK_a$ up, for example, to about 6.3. Even at this $pK_a$, however, if the carbonic acid is perturbed from equilibrium by add a strong base, it may take a long time for a new equilibrium to be established because of how slow the consumed $H_2CO_3$ is replenished by a reaction between carbon dioxide and water, given by [5] below:

$$CO_2 + H_2O \rightarrow H_2CO_3 \qquad [5]$$

As described above, the reaction 1208 generates basic hydroxide ions ($OH^-$), which may constantly perturb the equilibrium of the carbonic acid buffer, reducing its buffering resistance and causing the pH at the reference electrode 706 to rise. As the pH increases, deprotonation of bicarbonate may begin, leading to the formation of a bicarbonate/carbonate buffer system that drives the pH to a range from about pH 9.2 to pH 10.8, with the $pK_a$ of the bicarbonate/carbonate buffer system being about 10.3. Accordingly, the pH, at least at the reference electrode 706 may rise to between about pH 9 and pH 11.

Figure 13:
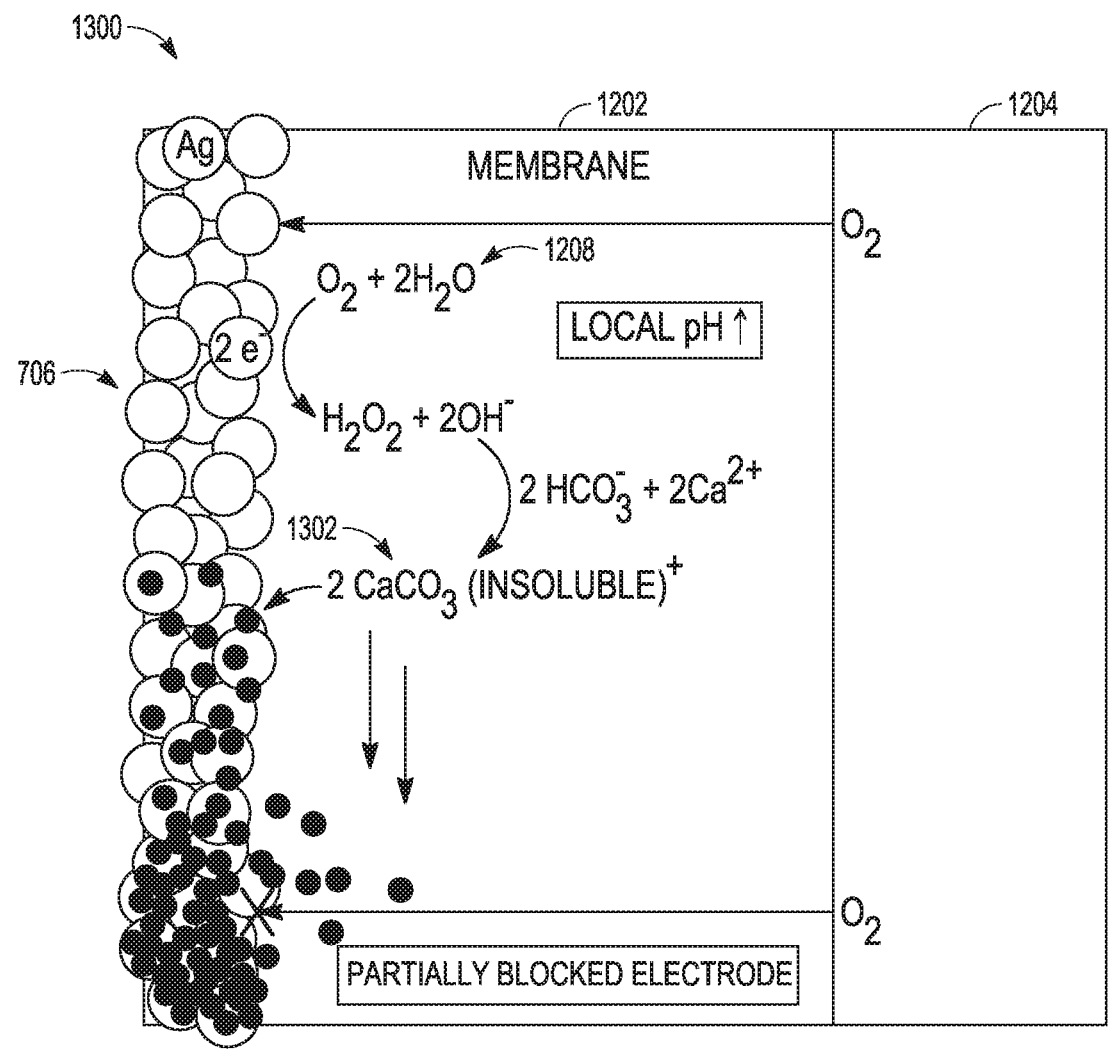
FIG. 13 shows a diagram illustrating an example slice of the reference electrode, the associated membrane system, and the interstitial fluid illustrating the precipitation of calcium carbonate due to elevated pH.

The rise in pH at the reference (e.g., counter-reference) electrode 706, in some examples, can cause calcium carbonate to precipitate on the reference electrode 706. FIG. 13 shows a diagram 1300 illustrating an example slice of the reference electrode 706, the associated membrane system 1202, and the interstitial fluid 1204 illustrating the precipitation of calcium carbonate due to elevated pH. For example, the solubility of calcium in carbonic acid buffered solutions may be sensitive to pH. When the pH of the buffered solution, such as interstitial fluid 1204, rises, the ratios of the protonated to unprotonated forms of the buffer may also change. The aqueous solubility of calcium with different forms of the carbonic acid buffer can be different. For example, calcium bicarbonate ($Ca(HCO_3)_2$) has a high aqueous solubility with a saturation concentration of just over 1 M. Calcium carbonate ($Ca(CO_3)$), on the other hand, is very insoluble in in water, with a saturation concentration of only about 77 μM.

The main form of soluble calcium in interstitial fluid may be calcium bicarbonate ($Ca(HCO_3)_2$). As the pH increases, the ratio of calcium bicarbonate to calcium carbonate decreases, resulting in more water insoluble calcium carbonate. The calcium carbonate reacts with the hydroxide ions generated at reaction 1208 to generate insoluble calcium carbonate at water at reaction 1302. The resulting calcium carbonate is deposited on the silver of the reference electrode 706, covering available silver and making it unavailable for redox. In examples in which silver chloride and/or a non-silver catalyst is present, these can also be covered by the calcium carbonate and made unavailable. Inclusion of the anti-mineralization agents, as described herein, may prevent the generation and/or depositing of calcium carbonate at the reference electrode 706.

Figure 14:
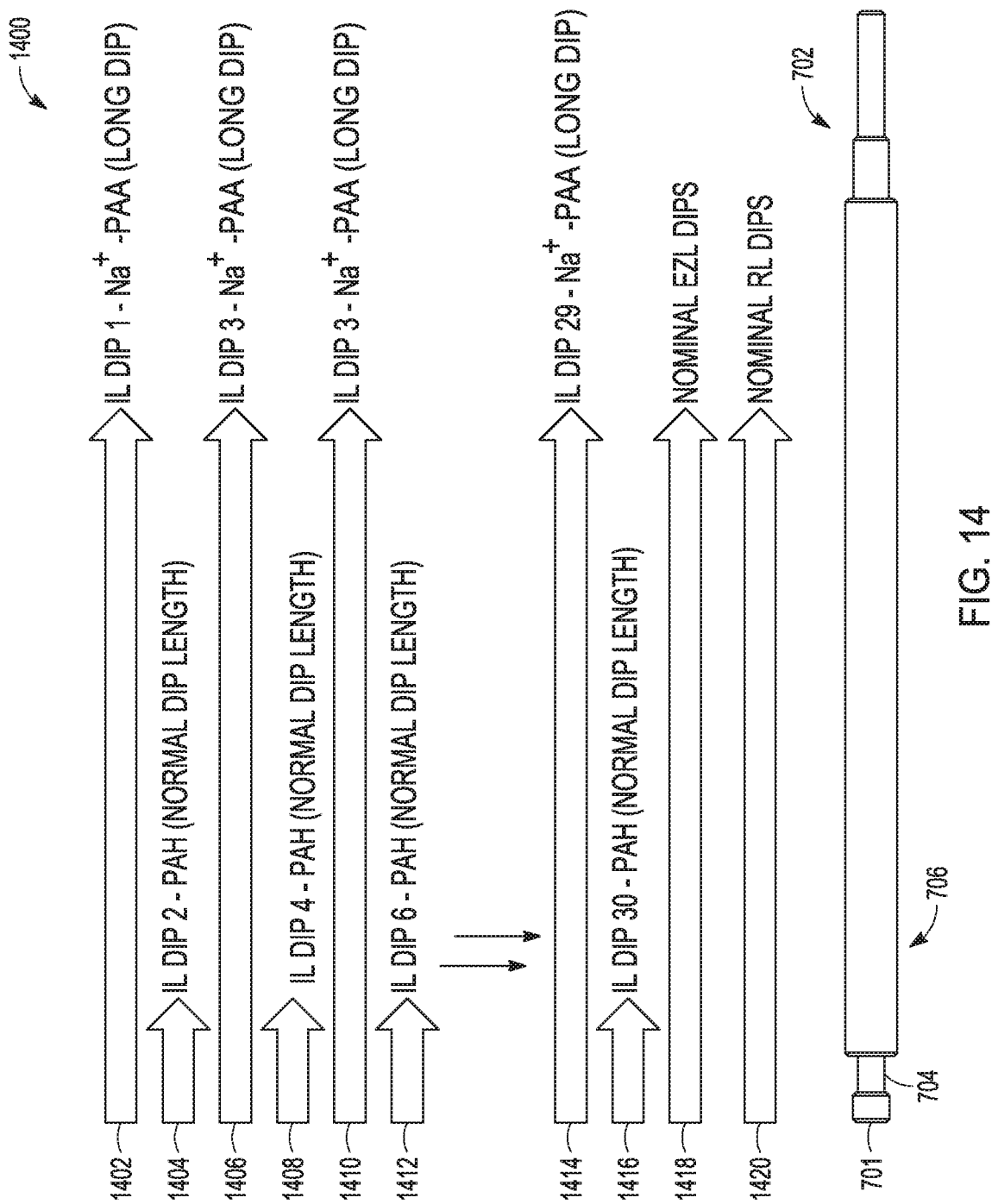
FIG. 14 is a diagram showing one example of a workflow that can be used to apply a membrane system including an anti-mineralization agent to a glucose sensor.

FIG. 14 is a diagram showing one example of a workflow 1400 that can be used to apply a membrane system including an anti-mineralization agent to the glucose sensor 702. The glucose sensor 702, including the working electrode 704 and reference electrode 706 is shown at the bottom portions of the workflow 1400. As described herein, the working electrode 704 is positioned near a distal end 701 of the sensor 702. The distal end 701 may be the end of the sensor 702 that is inserted first under the skin of a host. The workflow 1400 also shows a series of arrows indicating dips 1402, 1404, 1406, 1408, 1410, 1412, 1414, 1416, 1418, 1420 of the sensor 702 into various solutions. The lengths of the arrows Dips 1402, 1404, 1406, 1408, 1414, 1412, 1414, and 1416 may be provided to deposit an interference domain of a membrane system for the sensor 702. The interference domain may be provided to prevent interferents from reaching the working electrode 704. Interferents are molecules or other species that are reduced and/or oxidized at the electrochemically reactive surfaces of the sensor 702, either directly or via an electron transfer agent, to produce a false positive glucose signal. An interference domain may be provided to substantially restrict, resist, or block the flow of one or more interferents. Example interferents for glucose sensors include, acetaminophen, ascorbic acid, bilirubin, cholesterol, creatinine, dopamine, ephedrine, ibuprofen, L-dopa, methyl dopa, salicylate, tetracycline, tolazamide, tolbutamide, triglycerides, and uric acid. In general, the interference domain is less permeable to one or more of the interfering species than to the analyte, e.g., glucose.

In the example of FIG. 14, an interference domain can be formed by successively dipping the sensor 702 into an interference agent such as a polyallylamine solution (dips 1404, 1408, 1412, 1416) and into a polyacrylate acid solution (dips 1402, 1406, 1410, 1414). The polyacrylate acid solution may include, for example, a polyacrylate acid and water or another suitable solvent. Other example solvents that could be used in addition to or instead of water include organic solvents such as ethanol or another alcohol, or tetrahydraflorine (THF). The interference domain, in some examples, is formed over the working electrode 704 and not over the reference electrode. Polyacrylate, such as polyacrylate acid, however, is an anti-mineralization agent that decreases the rate and extent of calcium carbonate precipitation. Accordingly, in some examples, dips 1402, 1406, 1410, 1414 into the polyacrylate acid solution are extended, as shown in FIG. 14, such that the polyacrylate forms an anti-mineralization layer of the membrane system at the reference electrode 706.

For example, the sensor 702 may initially be dipped into the polyacrylate acid solution at dip 1402. The dip 1402, as shown, is a long dip. The sensor 702 may be submerged into the polyacrylate acid solution to a first depth that covers the working electrode and at least a portion of the reference electrode 706. The sensor 702 may be submerged into the polyacrylate acid up to a depth that covers the portion of the reference electrode 706 that is to be under the host's skin upon insertion. The dip 1402 deposits polyacrylate acid on the sensor 702 including the working electrode 704 and the portions of the reference electrode 706.

Following the dip 1402, the sensor 702 is dipped into the polyallylamine solution to a second depth that covers the working electrode 704, as shown, but does not cover a substantial portion of the reference electrode 706. In some examples, the dip 1402 covers less than about ¼ of the reference electrode 706 including, for example, less than about ¼ of the portion of the reference electrode 706 that is positioned under the host's skin upon insertion. Accordingly, polyallylamine is deposited at the working electrode 704. This process may be continued with alternate dips in the polyacrylate acid solution and the polyallylamine solution. In the example of FIG. 14, fifteen dips are made into each solution, although any suitable number may be performed. Upon completion of the dips 1402, 1404, 1406, 1408, 1410, 1412, 1414, 1416, 1418, 1420, polyacrylate and polyallylamine at the working electrode 704 may form an interference domain of a membrane system over the working electrode 704. Polyacrylate over the reference electrode may form an anti-mineralization domain.

The workflow 1400 of FIG. 14 also shows additional example dips 1418, 1420 that may be performed, for example, after the dips 1402, 1404, 1406, 1408, 1410, 1412, 1414, 1416, 1418, 1420. A dip 1418 may include dipping the sensor into an enzyme solution for providing an enzyme domain of the membrane system. The enzyme solution may include, for example, glucose oxidase or another suitable enzyme. The dip 1418 may be to a depth that covers the working electrode 704 and at least a portion of the reference electrode 706. In some examples, the dip 1418 is to the first depth used for the dip 1402 and other polyacrylate acid solution dips. A dip 1420 may include dipping the sensor into a resistance layer solution for providing a resistance domain of the membrane system. The dip 1420 may be to a depth covering the working electrode 704 and at least a portion of the reference electrode 706. In some examples, the dip 1418 is to the first depth used for the dip 1402 and other polyacrylate acid solution dips.

Figure 15:
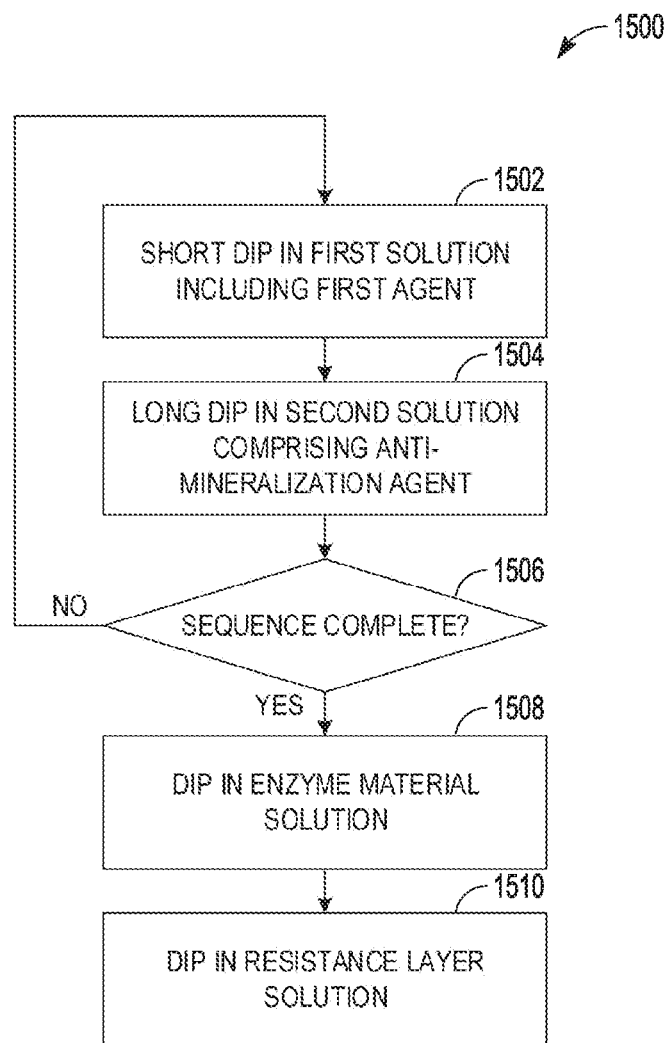
FIG. 15 is a flowchart showing one example of a process flow for treating a glucose sensor to provide a membrane system including an anti-mineralization domain at the reference electrode.

FIG. 15 is a flowchart showing one example of a process flow 1500 for treating a glucose sensor, such as the glucose sensor 702, to provide a membrane system including an anti-mineralization domain at the reference electrode 706. At operation 1502, the sensor is dipped into a first solution including a first agent. The dip at operation 1502 is a short dip to a depth that covers the working electrode 704. The first interference agent, when deposited at the working electrode 704, may form all or part of an interference domain of the membrane system. For example, the first agent may be or comprise polyallylamine. At operation 1504, the sensor 702 is dipped into a second solution comprising an anti-mineralization agent, such as polyacrylate. The dip at operation 1504 may be a long dip to a depth that covers the working electrode 704 and a portion (e.g., substantially all) of the reference electrode 704. In some examples, the order of the operation 1502 and 1504 may be reversed.

At operation 1506, it is determined whether the sequence of dips at operation 1502 and 1504 is complete. The sequence of dips may be complete, for example, when a predetermined number of short dips in the first solution and a predetermined number of long dips in the second solution are complete. If the sequence is not complete, the process flow 1500 returns to operation 1502. If the sequence is complete, the sensor 702 is dipped into an enzyme material solution at operation 1508. The dip into the enzyme material solution may be, for example, a long dip to a depth that covers the working electrode 704 and a portion of the reference electrode 704. The sensor 702 may be dipped into a resistance layer solution at operation 1510. For example, the dip at operation 1510 may be a long dip.

As described herein, the operating potential at the reference electrode 706 tends to drop when silver-catalyzed oxygen redox begins to dominate over silver chloride redox. As also described herein, this may be at least in part because at the oxygen concentrations encountered by the sensor 702 in vivo, the catalyst properties of the silver do not provide fast enough oxygen redox kinetics to match the potential generated by silver chloride redox.

The performance of silver as a catalyst for oxygen redox can be improved by increasing the surface area of available silver. In some examples, this can be accomplished by incorporating smaller-diameter silver particles into the binder material for the reference electrode 706. A larger number of smaller silver particles has a greater surface area of silver available to catalyze oxygen redox than an equivalent mass or volume of silver made up of larger particles. A challenge associated with using smaller silver particles, however, is maintaining electrical conductivity at the reference (e.g., counter-reference electrode) 706. The binder material, in some examples, is not electrically conductive. Accordingly, the electrical conductivity of the reference (e.g., counter-reference) electrode 706 may result from contact between silver particles, and sometimes silver chloride particles, in the binder material.

In various examples, the catalytic performance of silver for oxygen redox is improved by incorporating nanoscale silver particles with microscale silver and/or silver chloride particles in a binder material for the reference electrode 706. For example, as described herein, silver may be provided and incorporated into the binder materials as microscale flakes that are between about 0.5 microns and 1.5 microns thick and between about 5 microns and 15 microns wide. The average thickness of the silver particles may be about 1 micron and the average width is about 10 microns. Nanoscale silver particles may have an average size of between about 5 nanometers and about 500 nanometers. In some examples, nanoscale silver particles have an average diameter of less than 100 nanometers. Nanoscale silver particles can be incorporated into the binder material, for example, in the same way that the silver and silver chloride particles are incorporated into the binder material. In some examples, nanoscale particles of silver may make up between about 0.1% and about 10% by volume of the silver incorporated into the reference electrode 706. Nanoscale silver particles can be incorporated into examples of the reference electrode 706 including silver and silver chloride and, in various embodiments, can also be included into examples of the reference electrode 706 that include non-silver catalysts, as described herein.

In some examples, the reference electrode 706 is configured to promote aerobic silver chloride regeneration in vivo. In the presence of dissolved oxygen and chloride, a reference electrode 706 including silver and silver chloride may support an aerobic oxidation that regenerates silver chloride, also referred to herein as aerobic silver chloride regeneration. Examples of aerobic silver chloride generating reactions that may occur are given by [6] and [7] below:

$$2Ag+2Cl^-+O_2+2H^+ \rightarrow 2AgCl+H_2O_2 \quad [6]$$

$$4Ag+4Cl^-+O_2+4H^+ \rightarrow 4AgCl+2H_2O \quad [7]$$

The re-generated silver chloride can support silver chloride redox at the reference electrode 706, as described herein. Regenerating silver chloride can extend the life of the reference (e.g., counter-reference) electrode, for example, by extending the time during which the silver chloride redox dominates at the reference electrode 706, as described herein.

In many in vivo applications, however, the concentration of oxygen at the reference electrode 706 may not be high enough to support aerobic silver chloride regeneration at a reaction rate that is fast enough to complete with the rate of depletion of silver chloride due to silver chloride oxidation. For example, oxygen saturation in interstitial fluid may be between about 1% and 5%. At these concentrations, the impact of aerobic silver chloride regeneration may be greatly demised.

Various examples described herein are directed to reference electrodes 706 that a configured to increase the rate of aerobic silver chloride regeneration. For example, amounts of metallic transition metals such as zinc (Zn), aluminum (Al), manganese (Mn), magnesium (Mg), titanium (Ti), copper (Cu), etc. and/or alloys thereof, may be incorporated into silver provided at the reference electrode 706. This may change the bulk properties of the silver and make the silver particles more susceptible to aerobic oxidation. For example, the incorporation of metallic transition metal to silver particles at the reference electrode 706 may increase the oxidation rate of the resulting alloy. That, in turn, may tend to increase the reaction rate of aerobic silver chloride regeneration in vivo.

Transition metals can be incorporated into silver at the reference electrode 706 in any suitable manner. Consider one example in which silver particles are used, as described herein. The silver particles may be doped to include the selected transition metals. For example, silver and the selected transition metal or metals may be melted. The molten metals may be aspirated together, causing microparticles of silver with the dopant transition metal dissolved within the resulting solid phase silver. The aspiration may occur, for example, in an inert atmosphere, such as nitrogen or a noble gas. The resulting particles of silver and transition metal may be microscale flakes that are between about 0.5 microns and 1.5 microns thick and between about 5 microns and 15 microns wide. The average thickness of the silver/transition metal particles may be about 1 micron and the average width is about 10 microns.

In some examples, reference electrode capacity can be electrochemically enhanced by applying a high current density to the reference electrode 706. For example, experimental results suggest that the effective reference capacity of a reference electrode is increased at higher cathodic current densities at the reference electrode 706. The differences in reference electrode capacities for different current densities, in some examples, can be quite large. For example, high cathodic current densities result in large effective reference capacities while low current densities yield substantially lower effective reference capacities.

The current density dependence of reference electrode capacity, in some examples, arises from structural changes that occur within silver chloride microparticles are reduced (e.g., when charge is transferred to those particles). For example, every AgCl unit inside the solid that is reduced results in a redox-coupled loss of Cl— given by [8] below:

$$AgCl+e^- \rightarrow Ag+Cl^- \quad [8]$$

If silver chloride units are buried inside a bulk solid, such as silver chloride microparticles, the energy required to reduce the silver chloride may be higher, and sometimes significantly higher, to include the physical energy required to change the lattice structure of the silver chloride in such a way that the Cl— can percolate out. These changes in structure, in some examples, manifest as small cracks and pores in the solid silver chloride particles. The cracks and pores may act as ion transport channels that facilitate Cl— diffusion out of the solid particles and into the environment surrounding the silver chloride particle. When higher currents are driven into the silver chloride particles, a higher number of these cracks and channels may be formed and the resulting surface area of the silver chloride increases. Lower current densities, such as those encountered by the reference electrode 706 in vivo, may require fewer of these cracks and channels to keep up with the modest reaction rate of silver chloride redox, so the surface area of silver chloride may remain small.

Additionally, lower current densities at the reference electrode may lead to higher levels of crystallinity that slow current densities permit the requisite solid state phase change (AgCl to Ag) to occur in better accordance with thermodynamically determined stabilities (i.e. more crystallinity) rather than trapped as the kinetic product (i.e. more amorphous) that is observed when high current densities are driven. AgCl that is trapped in a very crystalline environment will be more difficult to reduce (i.e. need to apply a more negative current) because the entire extended crystal lattice has to adjust to permit Cl— diffusion out of the solid. AgCl in a more amorphous environment will have a lower solid state reorganization energy demand because there will be less long range order that needs to change to facilitate concomitant Cl— transport.

Referring back to the glucose sensor 702 of FIG. 7, the nominal current density at the reference electrode 706 in use may be low (<about 20 nA/inch). Accordingly, during normal use silver and silver chloride at the reference electrode 706 may not generate extensive cracks and channels in silver chloride and may support the silver chloride to silver solid state phase change in a way that results in a more crystalline structure. The effects of high current density may be Various examples are directed to treating a glucose sensor 702 including a reference electrode 706, with high current density reduction for a short time, for example, prior to use in vivo. This can be accomplished, for example, by passing a high current density through the reference electrode 706, for example, during a manufacturing process. The high current density may be selected to impart favorable material characteristics of high current density charging (e.g., high silver chloride surface area and amorphous crystalline structure) without dramatically reducing silver chloride loading at the reference electrode 706.

In some examples, the high current density may be applied to the reference electrode 706 in the presence of aqueous dissolved chloride (Cl—). This may provide the benefits of high current density and may also increase the silver chloride content at the reference (e.g., counter-reference) electrode, for example, due to reactions between the chloride and the silver of the reference (e.g., counter-reference) electrode 706.

Figure 16:
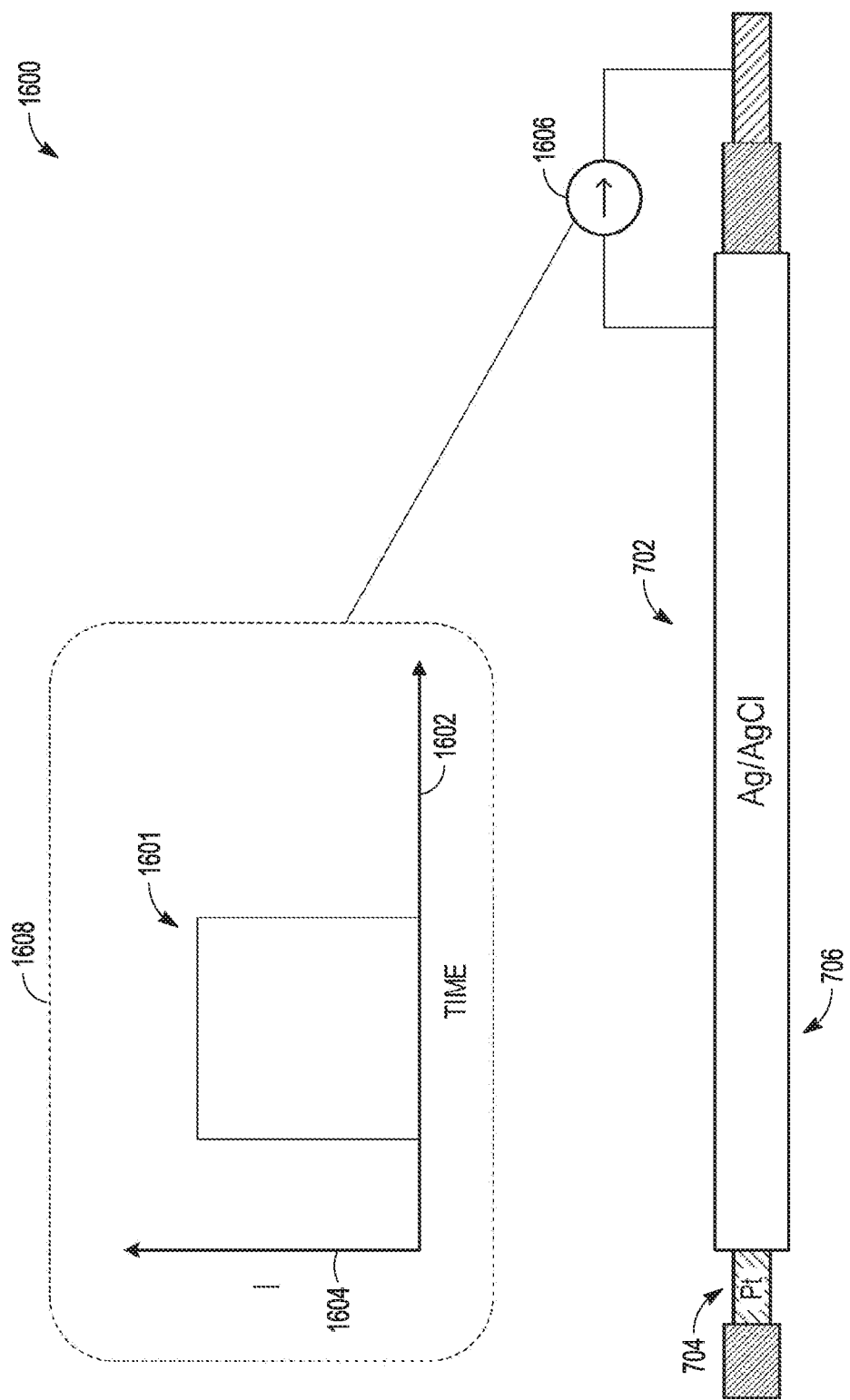
FIG. 16 is a diagram showing an example analyte sensor and illustrating the application of a high current density to the reference electrode.

FIG. 16 is a diagram 1600 showing an example analyte sensor and illustrating the application of a high current density to the reference electrode 706. The diagram 1600 includes a current source 1606 that provides a current to the sensor 702, for example, from the working electrode 704 to the reference electrode 706. In some examples, the current source 1606 may be configured to provide the current from the reference electrode 706 to the working electrode 704 in addition to or instead of what is shown in FIG. 16. Current diagram 1608 shows one example current pulse 1601 that can be provided by the current source 1606. The current pulse 1601 is shown on a plot including a horizontal axis 1602 indicating time and a vertical axis 1604 indicating current. Although one pulse is shown in FIG. 16, in some examples, multiple pulses may be provided.

In some examples, the magnitude of the current may be between about 100 nanoamps per inch of reference electrode 706 and about 1 milliamp per inch of reference electrode. In some examples, the current density is less than about 100 microamps. The length of the pulse may be, for example, between about one second and about five minutes. In some examples, current may be applied in waveforms other than a single pulse. The magnitude of the applied current, in some examples, leads to a current density at the reference electrode 706 that is greater than an average current density at the reference electrode 706 due to sensor current by a multiple of five or more.

In some examples, multiple pulses may be applied. In some examples, other current waveform shapes may be used. As described herein, the sensor 702, in some examples, is dipped into an aqueous solution including chloride while current is supplied.

In some examples, the capacity of the reference electrode 706 can be extended by increasing the loading of silver chloride. In some examples, this can include exposing the sensor 702 and/or the reference electrode thereof to hypochlorite ions (OCl⁻) and chloride ions (Cl—). When a silver/silver chloride reference electrode is exposed to hypochlorite ions and chloride ions. Hypochlorite ions (OCl⁻) and chloride ions (Cl—) can be provided from many suitable sources such as sodium hypochlorite (bleach) potassium hypochlorite, or lithium hypochlorite. The hypochlorite ions (OCl⁻) and chloride ions (Cl—) that can react with silver present at the silver/silver chloride reference electrode 706 to produce additional silver chloride, for example, as given by [9] below:

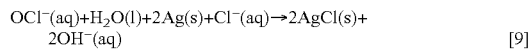

OCl⁻(aq)+H$_2$O(l)+2Ag(s)+Cl⁻(aq)→2AgCl(s)+ 2OH⁻(aq)   [9]

Figure 17A:
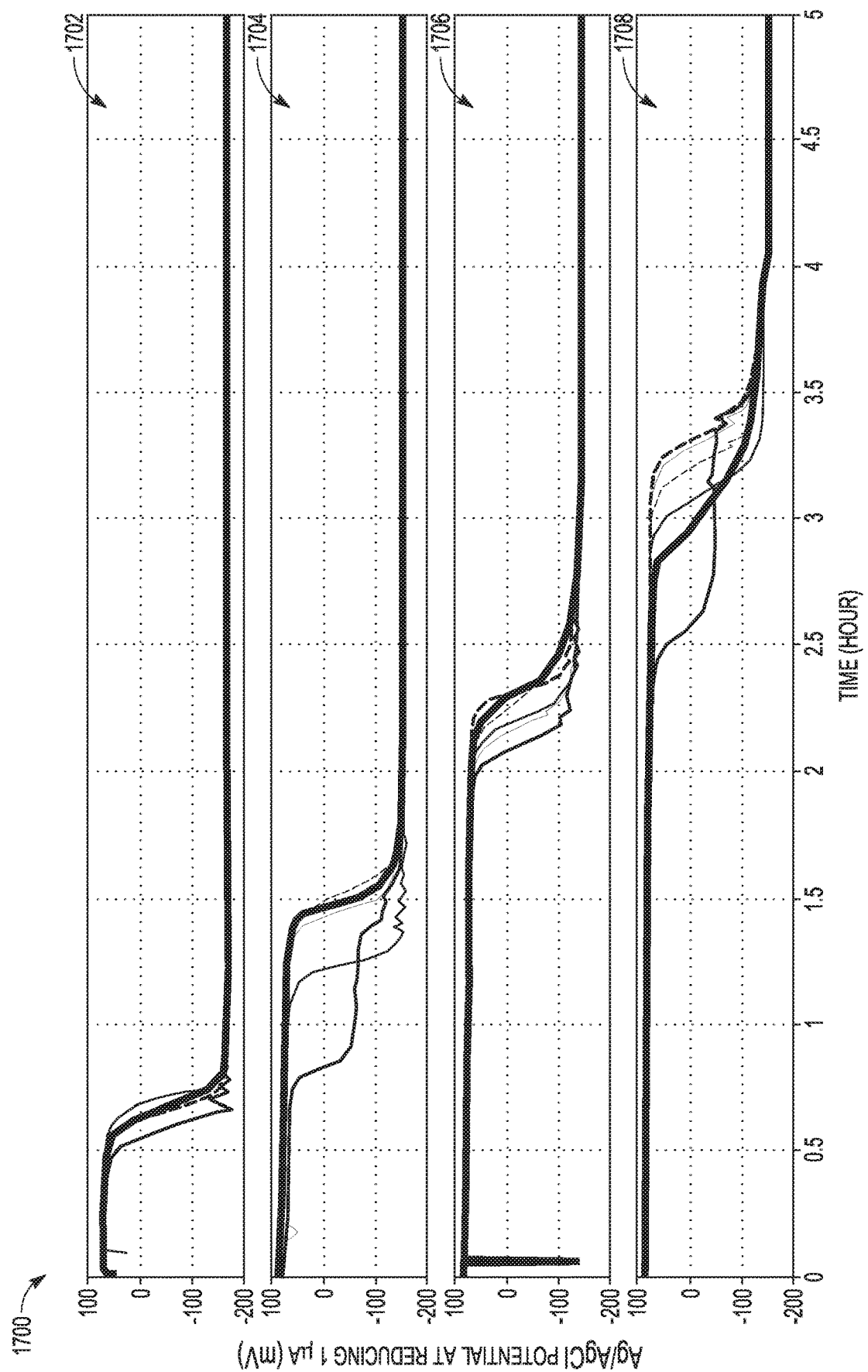
FIG. 17A is a plot showing examples of operating potential over time for glucose sensors, some of which were exposed to chlorine bleach.

FIG. 17A is a plot 1700 showing examples of operating potential over time for glucose sensors, similar to the sensor 702, some of which were exposed to chlorine bleach. The plot 1700 includes sub-plots 1702, 1704, 1706, 1708 showing trials of glucose sensors, including glucose sensors treated with chlorine bleach. In the sub-plots 1702, 1704, 1706, 1708, the horizontal axis indicates time in hours and the vertical axis indicates operating potential at the reference electrode with a sensor current of 1 microamp. The glucose sensors described by the sub-plots 1702 are similar to the sensor 702 and may include a membrane system, for example, similar to that described at FIGS. 4-5.

The sub-plot 1702 describes a set of glucose sensors that were not treated with chlorine bleach. The sub-plot 1704 describes a set of glucose sensors that were immersed for two minutes in a solution of 10% chlorine bleach. The sub-plot 1706 describes a set of sensors that were immersed for two minutes in a solution of 30% chlorine bleach. The sub-plot 1708 describes a set of sensors that were immersed for two minutes in 100% chlorine bleach. As shown, the untreated sensors described by the sub-plot 1702 began to show a drop in operating potential, indicating an exhaustion of silver chloride capacity after about 45 minutes. For the sensors treated in the 10% chlorine bleach solution, described by sub-plot 1704, the drop beings to appear at about 80 minutes. For the sensors treated in 30% bleach, described by sub-plot 1706, the drop appears even later, between two and two and one-half hours. The sensors treated in 100% bleach, described by sub-plot 1708, the drop begins around three hours. This may indicate that chlorine bleach immersion, as described herein, increases the effective capacity of glucose sensors and that higher concentrations of chlorine bleach may lead to greater increases.

Figure 17B:
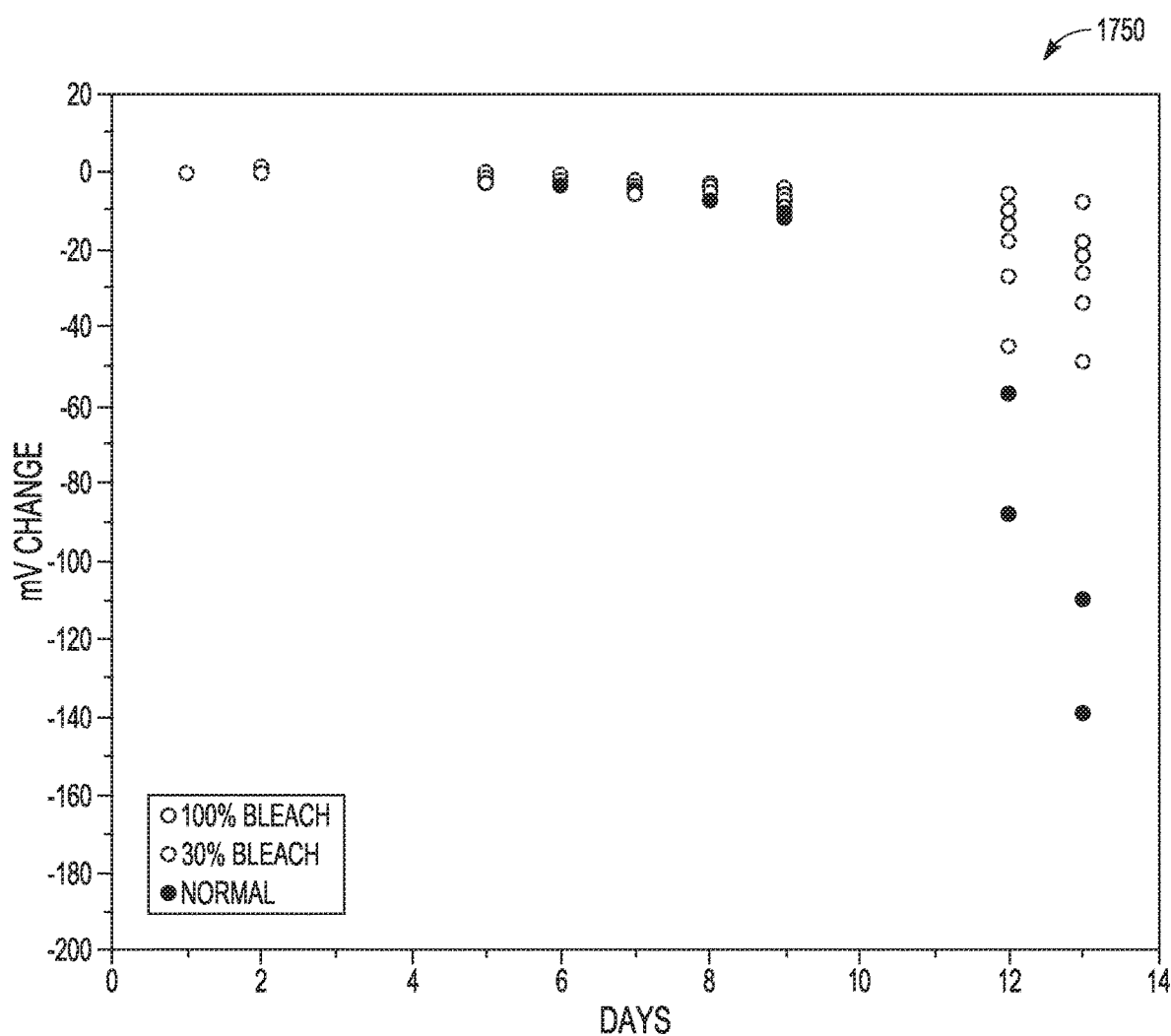
FIG. 17B is another plot showing changes in operating potential over time for glucose sensors, some of which were exposed to chlorine bleach.

FIG. 17B is a plot 1750 showing changes in operating potential over time for glucose sensors, similar to the sensor 702, some of which were exposed to chlorine bleach. FIG. 17B shows results of trials with three different categories of glucose sensors. A first category of glucose sensors were immersed for two minutes in a solution of 100% chlorine bleach. A second category of glucose sensors were immersed for two minutes in a solution of 30% chlorine bleach. A third category of glucose sensors were not treated with chlorine bleach. The glucose sensors of FIG. 17B were exposed to a glucose concentration of between about 100 mg/dl and 300 mg/dl.

The plot 1750 includes a horizontal axis indicating time, in days, and a vertical axis indicating a change in operating potential for the glucose sensors. As illustrated, the first category of glucose sensors treated with the solution of 100% chlorine bleach shows the smallest degradation in operating potential over time. The second category of glucose sensors treated with the solution of 30% chlorine bleach suffered greater operating potential degradation than the glucose sensors of the first category, but still experienced lesser degradation than the untreated third category.

A glucose sensor, such as the glucose sensor 702 includes a membrane system that may include a resistance domain. For example, in vivo, there may exist a molar excess of glucose relative to the amount of oxygen in the blood and, for example, in interstitial fluid. For example, for every free oxygen molecule in extracellular fluid, there are typically more than 100 glucose molecules present. However, an immobilized enzyme-based glucose sensor employing oxygen as a co-reactant (e.g., for oxidation at the working electrode 704), it may be desirable to provide sufficient oxygen that oxygen does not limit the rate of oxidation. Otherwise, the sensor current may not respond linearly to glucose concentration.

The glucose sensor may include a semipermeable resistance domain positioned over an enzyme domain. In this way, the resistance domain controls the flux of oxygen and glucose to the underlying enzyme domain, for example, in a manner that permits a ratio of oxygen to glucose such that oxygen does not limit the rate of oxidation. For example, the resistance domain may exhibit an oxygen to glucose permeability ratio of from about 50:1 or less to about 400:1. In some examples, the resistance domain exhibits an oxygen to glucose permeability ratio of about 200:1.

The resistance domain may include a polyurethane or other suitable membrane that has both hydrophilic and hydrophobic regions to control the diffusion of glucose and oxygen to the glucose sensor. A suitable hydrophobic polymer component is a polyurethane, or polyetherurethaneurea. As described herein, polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Example diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In some examples, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In some examples, the resistance domain is deposited onto the enzyme domain to yield a domain thickness of from about 0.05 microns or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, and more preferably still from about 2, 2.5 or 3 microns to about 3.5, 4, 4.5, or 5 microns. The resistance domain may be deposited onto the enzyme domain by spray coating or dip coating. In certain examples, spray coating is the preferred deposition technique. The spraying process atomizes and mists the solution, and therefore most or all of the solvent is evaporated prior to the coating material settling on the underlying domain, thereby minimizing contact of the solvent with the enzyme.

The hydrophobic and hydrophilic regions of the resistance domain allow the resistance domain to regulate the oxygen to glucose ratio at the enzyme domain, which ultimately affects a hydrogen peroxide to oxygen ratio at the working electrode leading to a suitably linear sensor current response. For example, both hydrophobic and hydrophilic regions may permit oxygen to diffuse through to the enzyme layer and ultimately to the working electrode 704. Only hydrophilic regions, however, support the diffusion of glucose.

Figure 18:
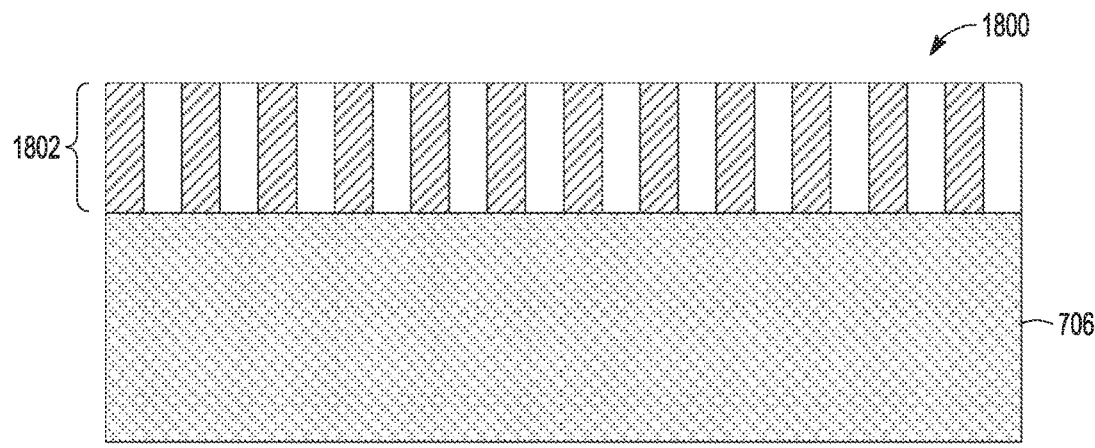
FIG. 18 is a diagram showing one example of a silver/silver chloride reference electrode having a resistance domain positioned thereover.

In many examples, the resistance layer is positioned over the working electrode 704 and also over at least a portion of the reference electrode 706. For example, the resistance layer may prevent the silver/silver-chloride of the reference electrode from directly contacting the body in vivo. When the resistance layer is positioned over the reference electrode 706, however, it may limit the availability of silver chloride for redox. This is shown by FIG. 18. FIG. 18 is a diagram 1800 showing one example of a silver/silver chloride reference electrode 706 having a resistance domain positioned thereover. The resistance domain 1802 includes hydrophilic regions (with no cross-hatching) and hydrophobic regions (with cross-hatching). It will be appreciated that, FIG. 18 shows a simplified arrangement of the resistance domain 1802. In practice, the hydrophobic and hydrophilic regions of the resistance domain 1802 may be more irregular than what is shown in FIG. 18.

The hydrophobic regions of the resistance domain 1802 may tend to limit ion transport. This can also limit the silver chloride at the reference electrode 706 that is available for redox. As a result, the effective silver chloride loading of the reference electrode 706 is reduced. Consider the example oxidation reaction given by [1] and example silver chloride redox reaction given by [2] above. As shown, electrons generated by oxidation at the working electrode 704 pass through the resistance domain 1802 to reach the reference electrode 706 and act as reactants in the silver chloride redox. Also, chloride ions ($Cl^-$) generated as products of the silver chloride redox diffuse out through the resistance domain 1802. For silver chloride positioned below hydrophobic regions of the resistance domain 1802, reduced ion transport may lead to a shortage of free electrons and/or a reduced diffusion of chloride ions, rendering the silver chloride under the hydrophobic regions less available or even unavailable for redox.

Figure 19:
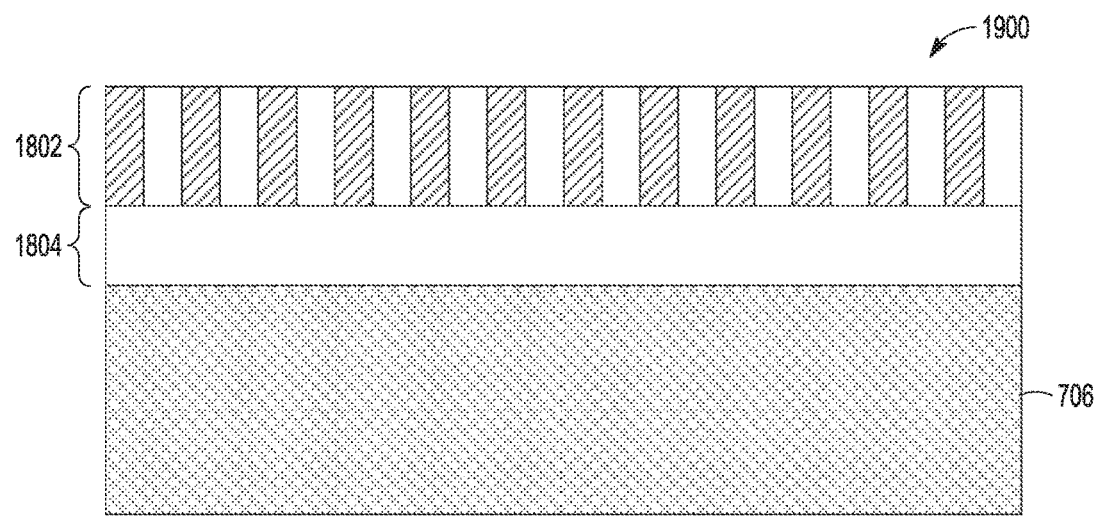
FIG. 19 is a diagram showing one example of an arrangement of the reference electrode and resistance domain including a hydrophilic layer positioned between the resistance layer and the reference electrode.

Various examples described herein address this and other issues by including a hydrophilic domain over at least a part of the reference electrode 706. FIG. 19 is a diagram 1900 showing one example of an arrangement of the reference electrode 706 and resistance domain 1802 including a hydrophilic domain 1804 positioned between the resistance domain 1802 and the reference electrode 706. The hydrophilic domain 1804 may create a hydrophilic path for ion transport through the resistance domain 1804 to a larger portion of the reference electrode 706 surface area. The hydrophilic domain 1804 can be or include any suitable hydrophilic material such as, for example, polyethylene oxide, a polyelectrolyte, or another hydrophilic polymer. In some examples, the hydrophilic domain 1804 includes an oxidase, such as glucose oxidase. For example, an enzyme domain covering the working electrode 704 may be extended to also cover all or part of the reference electrode 706 to constitute the hydrophilic domain 1804. Other example materials that may comprise some or all of the hydrophilic domain 1804 include any suitable polyurethane, any suitable polyvinylpyrrolidone (PVP), etc. The hydrophilic domain 1804 can be applied to the reference domain in any suitable manner including, for example, by dipping, spraying, printing, etc.

In some examples, the hydrophilic domain 1804 is made from an enzyme-infused polymer similar to an enzyme domain positioned over all or a part of the working electrode 704. For example, the enzyme domain positioned over the working electrode 704 can be extended to also cover some or all of the reference electrode 706. In examples in which the domains are applied by dipping, for example, as described with respect to FIGS. 14 and 15, this can be accomplished by extending a dip for applying the enzyme layer such that the solution for applying the enzyme layer submerges the working electrode 704 and the all or part of the reference electrode 706, for example, as shown in FIG. 14.

Figure 20:
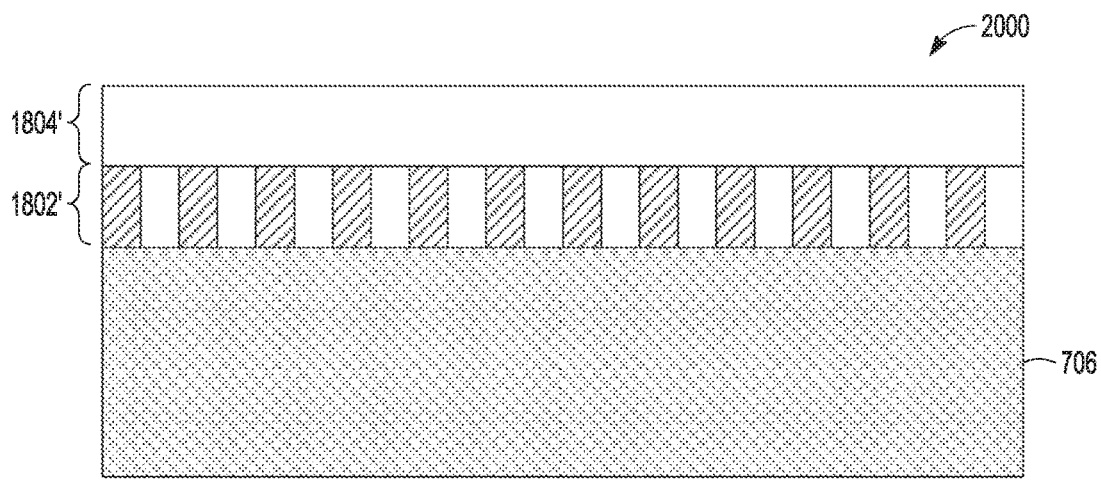
FIG. 20 is a diagram showing another example arrangement of a reference electrode and resistance domain in which the resistance domain is positioned between the reference electrode and a hydrophilic domain.

FIG. 20 is a diagram 2000 showing another example arrangement of a reference electrode 706 and resistance domain 1802' in which the resistance domain 1802' is positioned between the reference electrode 706 and a hydrophilic domain 1804'. In this example, the resistance domain 1802' has a reduced thickness relative to the resistance domain 1802. The reduced thickness of the resistance domain 1802' may facilitate higher levels of ion transport, making additional silver chloride available for redox. Consider an example in which the hydrophilic domain 1804' has a thickness of about 2 micrometers. The resistance layer 1802' may be reduced from less than about 7 micrometers to less than about 5 micrometers.

Figure 21:
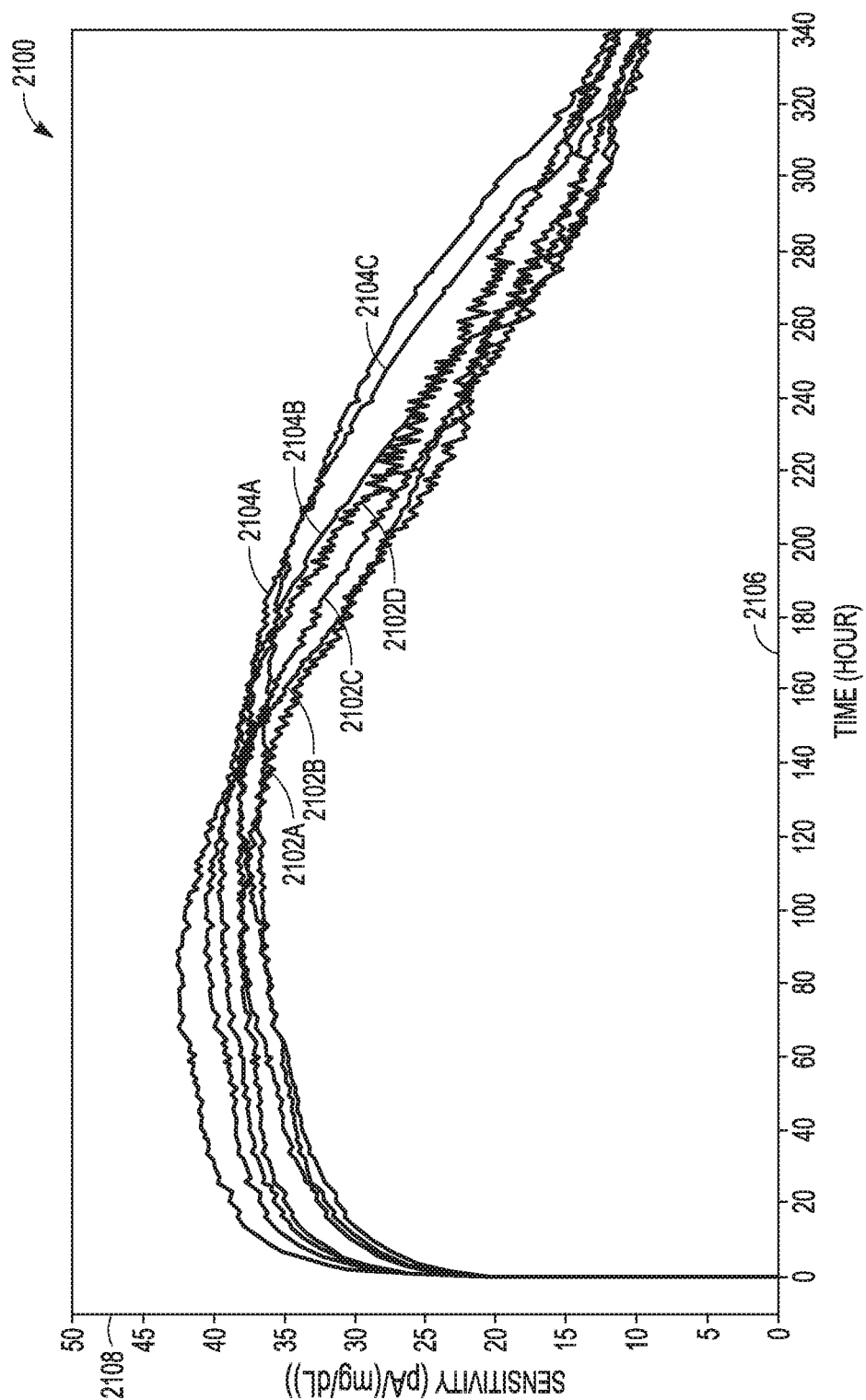
FIG. 21 is a plot showing example sensitivities of glucose sensors similar to the glucose sensor with different membrane system arrangements.

FIG. 21 is a plot 2100 showing example sensitivities of glucose sensors similar to the glucose sensor 702 with different membrane system arrangements. The plot 2100 includes a horizontal axis 2106 that indicates time and a vertical axis 2108 that indicates sensor sensitivity. Various trials 2102A, 2102B, 2102C, 2102D, 2104A, 2104B, 2104C are shown. Trials 2102A, 2102B, 2102C, 2102B utilize a membrane arrangement similar to the one shown in FIG. 18 in which a resistance layer is positioned over the reference electrode. Trials 2104A, 2104B, 2104C utilize a membrane arrangement similar to the one shown in FIG. 19 in which an enzyme domain over the working electrode is extended to also form a hydrophilic domain between the reference electrode 706 and the resistance layer 1814. As shown, the trials 2102A, 2102B, 2102C, 2102B begin showing noise around the midpoint of the test at about 180 hours. Trials 2104A, 2104B, 2104C including the hydrophilic layer described, however, have cleaner signals until later (e.g., between about 280 hours and 300 hours).

Figure 22:
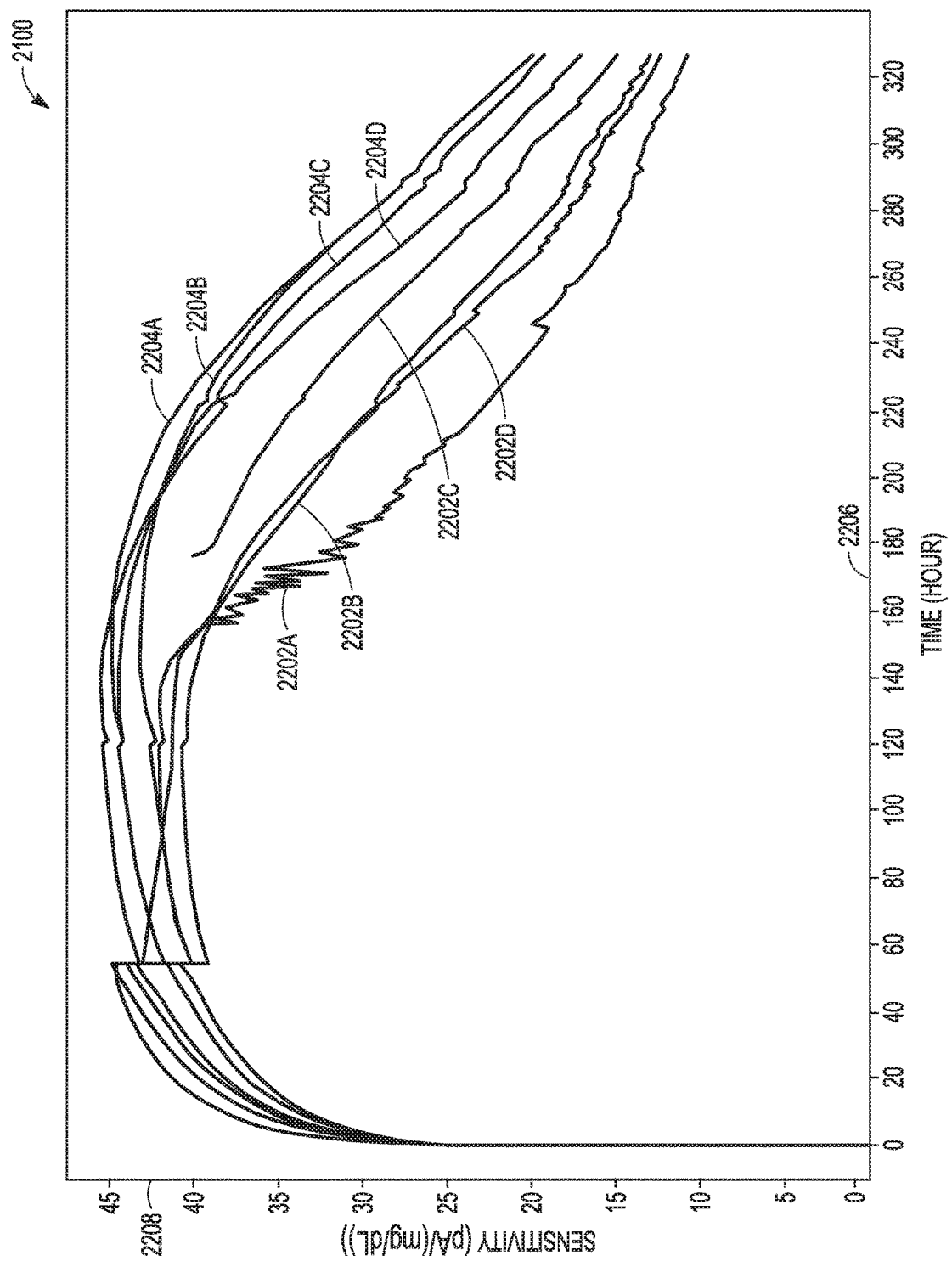
FIG. 22 is another plot showing example sensitivities of glucose sensors similar to the glucose sensor with different membrane system arrangements.

FIG. 22 is another plot 2200 showing example sensitivities of glucose sensors similar to the glucose sensor 702 with different membrane system arrangements. The plot 2200 includes a horizontal axis 2206 that indicates time and a vertical axis 2208 that indicates sensor sensitivity. Trials 2202A, 2202B, 2202C, 2202B utilize a membrane arrangement similar to the one shown in FIG. 18 in which a resistance layer is positioned over the reference electrode. Trials 2204A, 2204B, 2204C, 2204D utilize a membrane arrangement similar to the one shown in FIG. 20 in which a hydrophilic domain 2006 is deposited over the resistance layer 1812'. As shown, the trials 2202A, 2202B, 2202C, 2202B begin showing noise around the midpoint of the test at about 150 hours. Trials 2204A, 2204B, 2204C including the hydrophilic layer described, however, have cleaner signals throughout the test period.

In some analyte sensors, a reference electrode, such as the reference electrode 706 of the glucose sensor 102, is created by incorporating silver and silver chloride filler into a conductive ink or other binder material. The binder material, in some examples, is susceptible to micro cracking under repetitive bending in use. The probability of cracking may increase for reference electrodes with higher silver/silver chloride loading. Cracking at the reference electrode may lead to a noisy signal or the loss of signal altogether.

Figure 23:
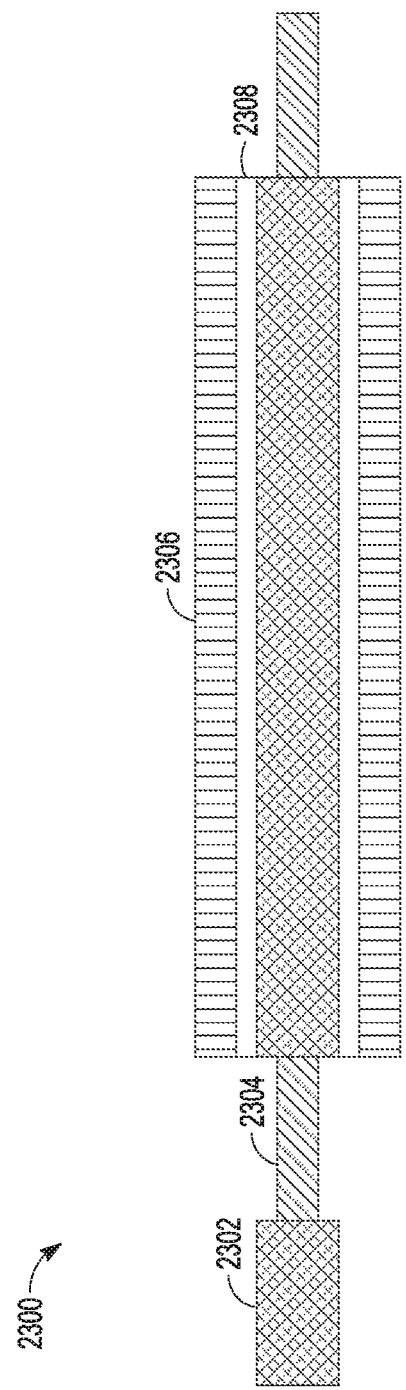
FIG. 23 is a diagram showing one example of an analyte sensor including a flexible layer positioned under the reference electrode.

In some examples, the probability of cracking at the reference electrode can be reduced by adding a flexible and/or stretchable conductive layer under the layer including the reference electrode. FIG. 23 is a diagram showing one example of an analyte sensor 2300 including a flexible layer 2308 positioned under the reference electrode 2306. The analyte sensor 2300 includes an elongate conductor 2304. In some examples, the elongate conductor 2304 is made of platinum and may make up all or part of a working electrode. In other examples, platinum or another suitable working electrode material is applied over an elongate conductor or other elongate material. An insulating layer 2302 is positioned over the elongate conductor 2304. The insulating layer 2302 may include an insulating polymer such as, for example, polyimide, polyurethane, parylene, or any other suitable insulating material or materials.

The flexible layer 2308 may include, for example, a flexible polymer such as a polythiophene derivative. In some examples, the flexible layer 2302 may be or include a stretchable ink such as silver paste. In some examples, the flexible layer is conductive. The reference electrode 2306 is positioned over the flexible layer 2302 and may include silver/silver chloride. The reference electrode 2306 may be applied over the flexible layer 2308, for example, via dipping, printing, ink deposition, etc.

In some examples, the flexible layer 2302 provides pliability and accordingly lessens the risk of cracking at the reference electrode 2306. Also, in examples in which the flexible layer 2302 is conductive, it may reduce or eliminate signal noise to wire fatigue including, for example, any cracking that may occur.

In some examples, the performance of an analyte sensor, such as for example, the glucose sensor 702, is affected by the eccentricity of the layer including the reference electrode. Referring, for example, to FIGS. 3 and 4, if the layer 343 including the reference electrode is eccentric (e.g., not having the same center as the elongated conductive body 341), the performance of the analyte sensor may suffer. For example, silver/silver chloride or other suitable material for the reference electrode may be unevenly distributed around the cross-sectional circumference of the elongated conductive body, causing uneven exhaustion of reactants and unpredictable behavior of the sensor.

In some examples, X-ray testing techniques can be used to detect eccentricity in the reference electrode layer of an analyte sensor. An X-Ray sensor can be positioned, for example, to capture in-line and/or cross-sectional images of an analyte sensor. FIGS. 24A and 24B show in-line X-ray images 2400A, 2400B showing example analyte sensors 2402A, 2402B. Sensors 2402A, 2402B include respective elongated conductive bodies 2404A, 2404B. In some examples, the elongated conductive bodies 2404A, 2404B are made of platinum or another suitable material for the working electrode or, in other examples, have a layer such as the layer 338 deposited thereon.

The X-ray images 2400A, 2400B also show respective insulating layers 2406A, 2406B. Insulating layers 2406A, 2406B may be similar to the layer 340 described herein. Reference layers 2408A, 2408B are positioned over the insulating layers 2406A, 2406B, for example, similar to the layer 343 described above.

The cross sectional X-ray images 2400A, 2400B can be used to identify sensors have eccentric reference layers. For example, the insulating layers 2406A, 2406B may be transparent in the X-ray images 2400A, 2400B. A computing device or other similar device can be programmed to analyze the images 2400A, 2400B and find a distance between the elongated conductive bodies 2404A, 2404B and the reference layers 2408A, 2408B on each side. If the distances are different, it indicates reference layer eccentricity. For example, the sensor 2402A does not have an eccentric reference layer 2406A because the distance from the elongated conductive body 2404A to the reference layer 2408A is substantially similar on both sides of the elongated conductive body 2404A. (In the orientation of FIGS. 24A and 24B, "both sides" refers to the top and the bottom.) On the other hand, the sensor 2402B shows an eccentric reference layer, for example, because the distance from the elongated conductive body 2404B to the reference layer 2408B is larger on one side (e.g., the bottom side) than on the other side (e.g., the top side).

FIG. 25 shows cross-sectional X-ray images 2500A, 2500B showing example analyte sensors 2502A, 2502B. In this example, the X-ray images 2500A, 2500B are taken, for example, at an edge or end of the sensors 2502A, 2502B to provide the cross section that is shown. In this example, the sensors 2502A, 2502B include elongated conductive bodies 2504A, 2504B, insulating layers 2506A, 2506B, and reference layers 2508A, 2508B similar to the arrangement shown in FIGS. 24A and 24B.

In this example, the sensor 2502A includes an eccentric reference layer 2508A. This is shown in the x-ray image 2500A because the distance from the elongated conductive body 2504A to the reference layer 2508A is not uniform around the circumference of the elongated conductive body 2405A. In contrast, the sensor 2502B does not include an eccentric reference layer 2508B because the distance from the elongated conductive body 2504B to the reference layer 2508B is substantially uniform about the circumference of the elongated conductive body 2504B. In some examples, a computing device is programmed to analyze the images 2500A, 2500B and identify the distance from the elongated conductive body 2504A 2504B to the reference layers 2508A, 2508B about the circumference of the elongated conductive body 2504A, 2504B. The computing device can generate an alert or alarm if the measured distance varies by more than a threshold amount about the circumference.

In some examples, X-ray images, such as those shown in FIGS. 24A, 24B, and 25 can be used to provide immediate feedback for die positioning during manufacturing of the sensors. In this way, any detected defects can be reduced or eliminated for future-generated sensors. Also, in some examples, X-ray images, such as those shown in FIGS. 24A, 24B, and 25 can be captured and used at a skiving station that cuts the elongated conductive body to generate multiple sensors. For example, the X-ray images can be used to determine how much to ablate the sensors at different angles. The X-ray image can indicate a level of non-uniformity in the reference coating thickness at different angular locations around the cylindrical wire. Using an angular datum, the laser pulses can be optimized to delivered known/required amount of energy to remove just the Ag/AgCl reference coating without the need to over ablate the polyurethane insulation.

Various examples are directed to alternative ways to provide a silver/silver chloride or other suitable reference electrode layer to analyte sensor. Referring again to FIG. 4, the working electrode is provided by the layer 338 and reference electrode is provided by the layer 343. A layer 340 is provided between the layer 338 and the layer 343 to act as an insulator between the working electrode, provided by layer 338, and the reference electrode. As shown in FIG. 4, the analyte sensor 334 includes a window 339 that exposes the layer 338. In some examples, the sensor 334 is manufactured by applying the layers 340 and 343. After the layers 340 and 343 are applied the window 339 is generated by removing portions of the layers 340 and 343 to expose the layer 338 as shown in FIG. 4. The removal of the layers 340 and 343 may be performed, for example, using laser skiving or another suitable technique.

Laser skiving or other removal techniques can add cost to the manufacturing of the analyte sensor 334. For example, the cost of laser skiving may be related to the amount of material to be removed. Accordingly, it may be desirable to reduce or eliminate material of the third layer 343 that is removed to form the window 339. Also, in some examples, it is desirable to increase the uniformity of the third layer 343. For example, it may be desirable for the layer 343 to be substantially uniform about the circumference of the elongated conductive body 341.

Figure 30:
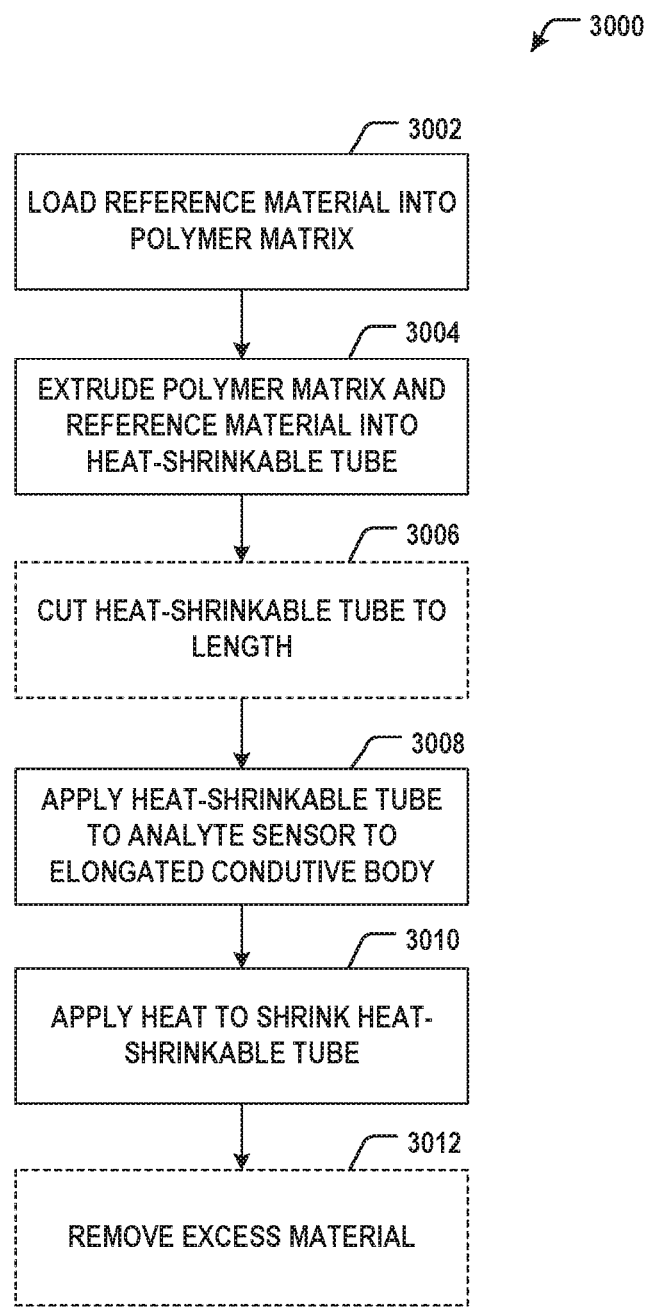
FIG. 30 is a flowchart showing one example of a process flow that may be executed to provide a reference electrode layer to an analyte sensor using heat-shrinkable tubing.

In some examples, the reference material, such as silver/silver chloride, is loaded into a binder material, as described herein. The binder material is extruded into a heat-shrinkable tubing that is then applied to the analyte sensor 334 to generate the third layer 343. This may reduce the amount of material to be removed by laser skiving or other techniques. It may also improve the uniformity of the reference material about the circumference of the elongated conductive body 341. FIG. 30 is a flowchart showing one example of a process flow 3000 that may be executed to provide a reference electrode layer, such as the layer 343, to an analyte sensor using heat-shrinkable tubing.

At operation 3002, a reference material is loaded into a polymer binder. In some examples, the polymer binder comprises a thermoplastic polymer such as, for example, a polyethylene terephthalate (PET), a polytetrafluoroethylene (PTFE), a fluorinated ethylene propylene (FEP), or a polyolefin. In some examples, the binder material is conductive. Any suitable reference material may be used including, for example, silver/silver chloride or another suitable material as described herein. At operation 3004, the polymer binder and reference material are extruded into heat-shrinkable tubing.

At optional operation 3006, the heat-shrinkable tubing may be cut to length. The selected length may be based on the desired length of the analyte sensor 334. For example, the heat-shrinkable tubing may be cut to a length that can be applied over the layer 340 while leaving an opening for the window 339. In some examples, the operation 3006 is omitted.

At operation 3008, the heat-shrinkable tubing is applied to the elongated conductive body 341. For example, the heat-shrinkable tubing may be applied around the elongate conductive body 341 over the layer 340. In some examples, multiple cut sections of heat-shrinkable tubing are applied to the elongate conductive body 341. Successive sections of heat-shrinkable tubing may be applied with a gap or spacing therebetween so as to form a break in the layer 343 corresponding to the window 339. The elongate conductive body 341 may be subsequently cut into sections with some or all of the sections forming separate analyte sensors 334, for example, as shown in FIG. 4. Each resulting analyte sensor 334 may include a window 339 with a portion of heat-shrinkable tubing making up the portion of the layer 343 positioned on a proximal side of the window 339 and another portion of the heat-shrinkable tubing making up the portion of the layer 343 positioned on a distal side of the window 339. In another example, the portion of the heat-shrinkable tubing positioned on the distal side of the window 339 may be omitted. In other examples, the heat-shrinkable tubing may be applied continuously. The window 339 may be formed by removing a portion of the heat-shrinkable tubing, as described herein at operation 3012. At operation 3010, heat is applied to the heat-shrinkable tubing. The application of heat may cause the heat-shrinkable tubing to shrink, thereby becoming fastened to the elongated conductive body 341.

At operation 3012, excess material may be removed from the elongated conductive body 341, now including the heat-shrinkable tubing. In some examples, as described herein, the heat-shrinkable tubing is spaced on the elongated conductive body 341 such that, after heat is applied, there is no heat-shrinkable tubing and included reference material over the window 339. If insulating material of the layer 340 is present over the window 339, this excess material may be removed at operation 3012. In other examples, heat-shrinkable tubing may be applied over all of the elongated conductive body 341 (e.g., without a gap). In these examples, heat-shrinkable tubing and included reference material may be removed from the window 339. Excess material may be removed at operation 3012 using any suitable technique such as, for example, laser skiving. In some examples, removing portions of the heat-shrinkable tubing using laser skiving may be less expensive than removing material that is coated or plated using other techniques. In some examples, the process flow 300 may also make it more likely that the reference layer is uniform (e.g., not eccentric) and may, in some examples, eliminate the need to trim or skive the reference layer. Upon completion of the process flow 3000, the analyte sensor 334 manufacturing may be completed. For example, the membrane system 332 may be applied using any suitable technique.

In some examples, instead of being used as a binder material, heat-shrinkable tubing has reference material, such as silver/silver chloride plated, bonded, or otherwise applied to an outside surface thereof. The heat-shrinkable tubing can be applied over the elongated conductive body 341. In this example, the heat-shrinkable tubing itself may act as all or part of the insulating layer 340 separating the working electrode from the reference electrode. When this arrangement is used with heat-shrinkable tubing that is cut to length as described at operation 3006, it may further reduce laser skiving because portions of the layer 340 corresponding to the window 339 may not need to be removed. In these and other examples described herein, the reference layer 343 can be initially applied with silver. Additional processing, such as the bleach treatment described herein, can be subsequently applied to generate silver chloride. Also, in some examples, a reference layer can be applied using inkjet printing.

Figure 26:
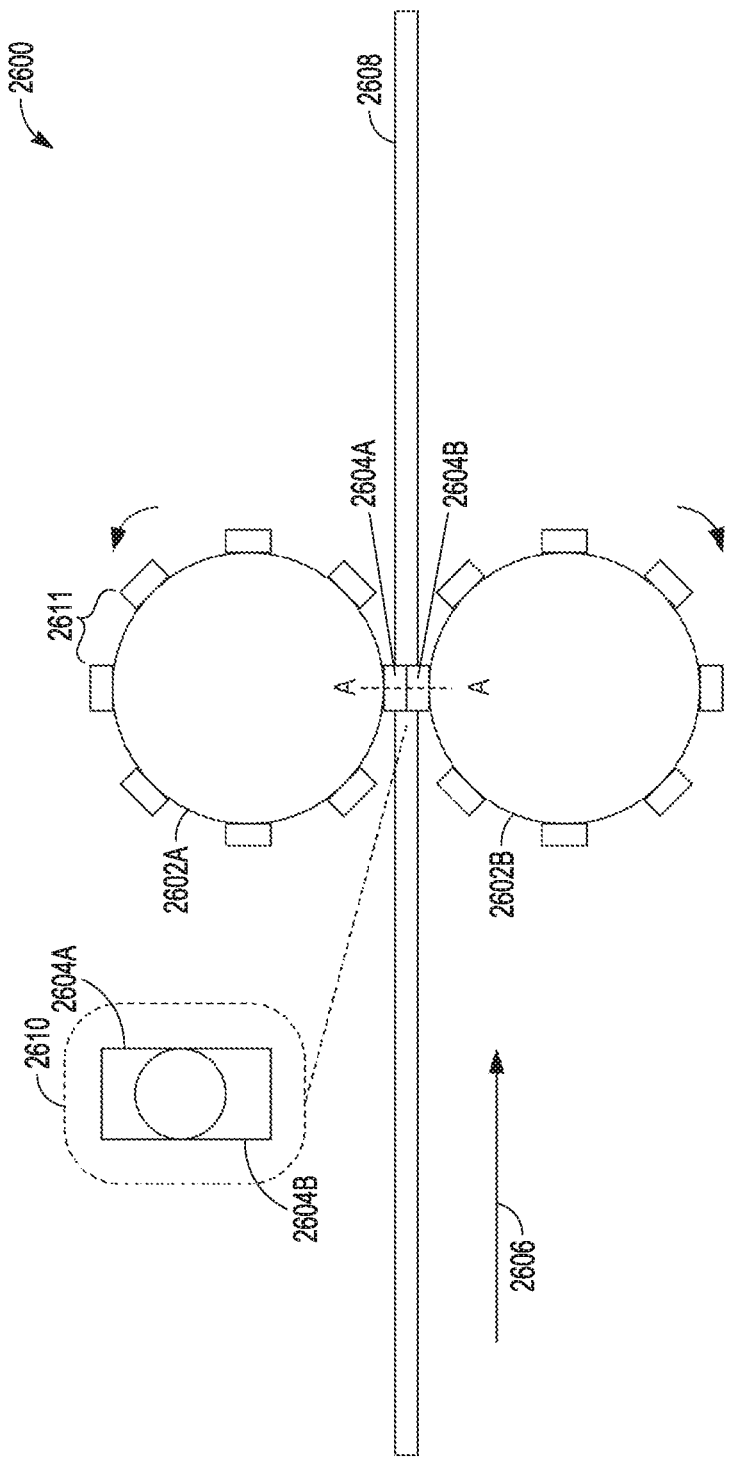
FIG. 26 is a diagram showing one example of a pad printing apparatus that can be used to apply a reference material to an analyte sensor.

In some examples, a reference layer including a reference material, such as silver/silver chloride, can be applied using a pad printing apparatus. FIG. 26 is a diagram showing one example of a pad printing apparatus 2600 that can be used to apply a reference material to an elongated conductive body 2608. The pad printing apparatus 2600 includes a first wheel 2602A and a second wheel 2602B. The wheels 2602A, 2602B including pads, such as pads 2604A and 2604B coupled, as shown around the respective circumferences of the wheels 2602A, 2602B. An elongated conductive body 2608 is passed between the wheels 2602A, 2602B in the direction indicated by arrow 2606. In some examples, the elongated conductive body 2608 includes a layer making up the working electrode, such as the layer 338 above, and a layer making up an insulating layer, such as the layer 340 above.

The pads, including pads 2604A and 2604B may be infused with a reference material, such as, for example, a binder material including silver and silver chloride, as described herein. As the elongated conductive body 2608 passes between the pad, reference material is deposited on the elongated conductive body 2608. The contour of the pads 2604A, 2604B may match the shape of the elongated conductive body 2608. For example, window 2610 shows a cross section of the pads 2604A, 2604B along the line A-A. As showing, a roughly circular opening between the pads 2604A, 2604B. The elongated conductive body 2608 passes through the circular opening, causing the pads to deposit reference material onto the elongated conductive body 2608 all around. In some examples, the elongated conductive body 2608 can have a flat or ribbon shaped cross-section. In these examples, the contour of the pads 2604A, 2604B may be modified to match the shape of the elongated conductive body 2608.

The pads may be spaced along the circumference of the wheels 2602A, 2602B in a manner that determines the length and spacing of reference material sections on the elongated conductive body 2608. For example, the width of the pads may determine the length of the reference material on the elongated conductive body 2608. The distance 2611 between pads may determine the distance between reference material sections. The elongated conductive body 2608 may be cut between reference material sections to generate multiple analyte sensors, with each reference material section corresponding to a reference electrode of an analyte sensor.

Some examples are directed to analyte sensors including reference electrodes with increased flexibility. For example, when electrodes are stiffer than human tissue, the electrodes can cause repeated injury to tissue. This can be painful and can cause tissue to become inflamed. Also, implanting materials with poor biocompatibility may also lead to increase inflammation and foreign body response, which can cause the body of the host to wall-off the reference electrode, impeding the flow of ions that are needed for oxidation and redox reactions, as described herein. In some examples, an analyte sensor includes a soft reference electrode. A binder material may be made with a tunable stiffness. The binder material may be infused with silver and silver chloride as described herein. In examples where the binder material lacks sufficient conductivity, a conductive filler could also be added, such as graphene, carbon black, or carbon nanotubes (CNT) material. Additional additives may be added to the binder material, such as anti-inflammatory drugs, a buffer to modulate pH, and/or free radical scavengers.

In various examples, an analyte sensor includes a reference electrode comprising a conductive polymer binder material. For example, when silver chloride at the reference electrode is consumed, the particle size of the silver chloride decreases. This can cause voids in the binder material that can increase the likelihood of fatigue-based structural failure or can simply cause electrical faults. In some examples, electrical faults can be reduced by utilizing a conductive binder material, such as a conductive epoxy, conductive polyurethane, or other conductive polymer.

Figure 27:
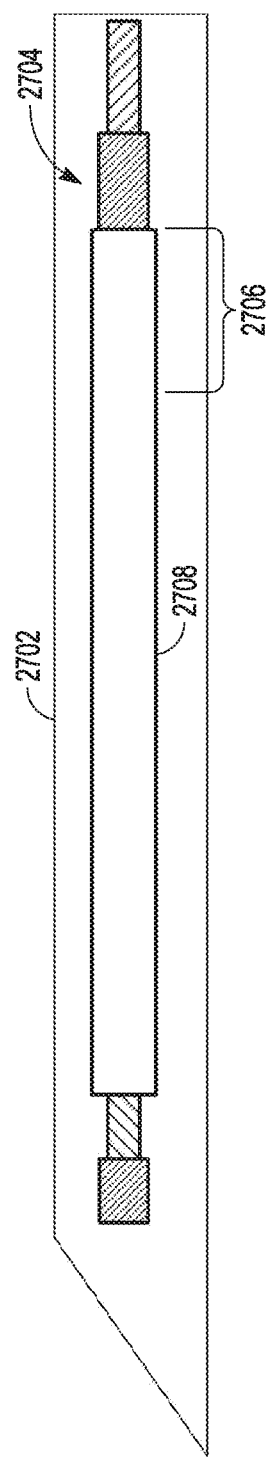
FIG. 27 shows an example analyte sensor within an applicator needle for inserting the sensor under the skin of a patient.

FIG. 27 shows an example analyte sensor 2704 within an applicator needle 2702 for inserting the sensor 2704 under the skin of a patient. The applicator needle 2702 may be any suitable hypodermic needle such as, for example, a 304 SS needle. In the example of FIG. 27, a proximal portion 2706 of a reference electrode 2708 of the sensor 2704 is treated to remove silver chloride. Removal of silver chloride from the proximal portion 2706 of the reference electrode 2708 may lessen the risk that the reference electrode 2708 will corrode while in the needle 2702.

Silver chloride in the presence of iron (such as in steel) may undergo a redox reaction leading to the formation iron oxide or rust, such as $Fe_2O_3$. As a result, increasing the loading of silver chloride in the reference electrode 2708 to increase the capacity of the reference electrode. However, silver chloride is a strong oxidizing agent and corrodes metals when in contact, especially at high humidity and temperature. Accordingly, when bare reference electrode 2708 comes into contact with the inside of the needle 2702, it acts as a reducer of the iron from the needle and generates rust. This can be mitigated, for example, by removing the silver chloride from the proximal portion 2706 of the sensor 2704. For example, the proximal portion 2706 may be most likely to come into direct contact with the needle 2702.

Removal of silver chloride from the sensor 2704 can be accomplished in any suitable manner. In some examples, the proximal portion 2706 of the reference electrode 2708 is exposed to ultraviolet radiation. This causes the silver chloride to degenerate into silver and chlorine radical, as given by [10] below:

$$AgCl(s) \rightarrow Ag(s) + Cl.\qquad [10]$$

More distal portions of the reference electrode 2708 may be screened by a mask or any other kind of light barrier. UV exposure may occur during skiving/singulation, when a single coated elongated conductive body is cut into separate sensors and/or after skiving.

In another example, silver chloride can be removed from the proximal portion 2706 of the reference electrode 2708 by immersing the proximal portion 2706 in ammonia ($NH_3$). For example, ammonia may ligate the silver atoms at begin to dissolve the reference coating comprising silver chloride. This removes silver chloride from the surface and mitigates the oxidizing of iron in the needle.

Another arrangement to address reference electrode fatigue and the resulting lack of electrical connectivity in the reference electrode includes applying all or part of the reference electrode material or layer as a pure silver ink. The pure silver ink may be applied to the insulating layer in any suitable manner. Upon application of the silver ink, the reference electrode may be cured, for example, at 300 C or more. This may sinter the ink to form a network of silver. The resulting silver may be chloridized in any suitable manner to form a suitable level of silver chloride.

Figure 28:
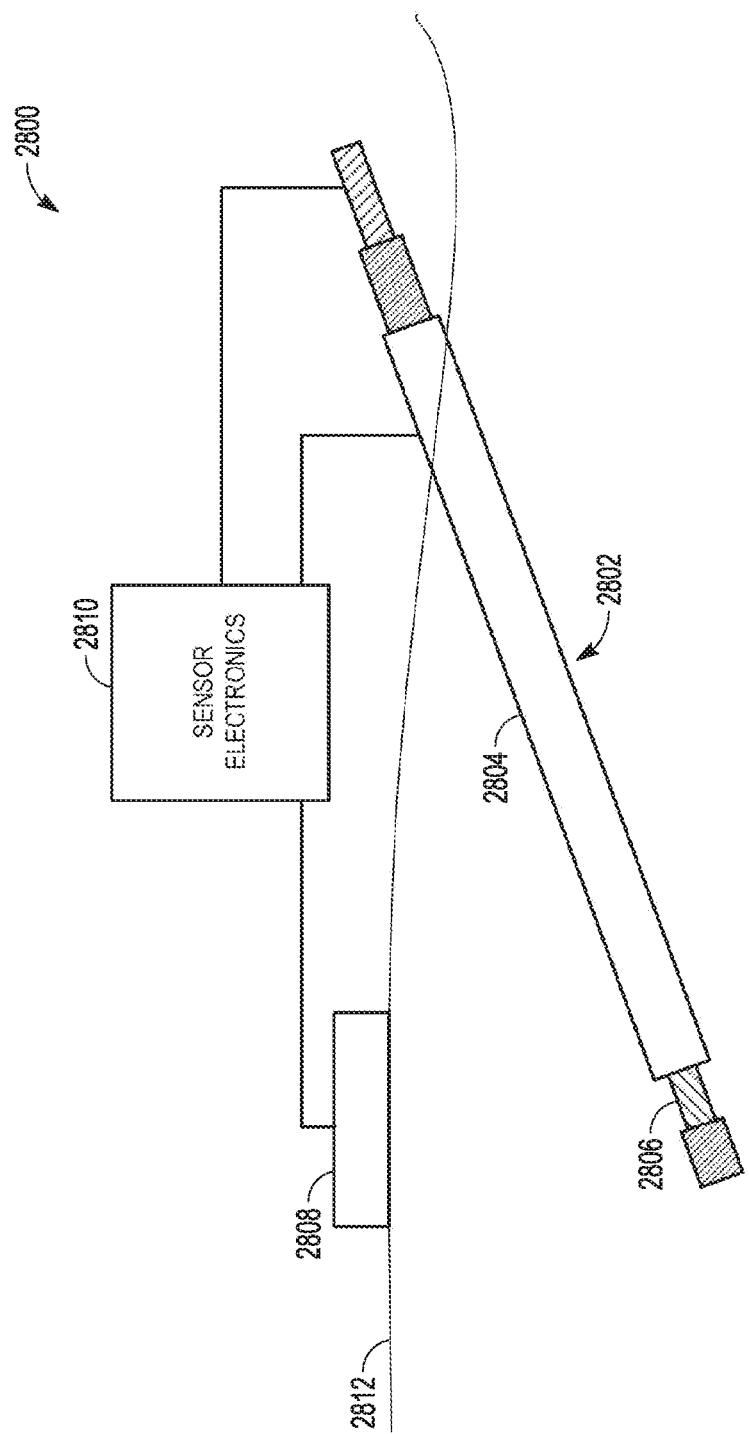
FIG. 28 is a diagram showing an example arrangement including an analyte sensor with a third electrode.

FIG. 28 is a diagram showing an example arrangement 2800 including an analyte sensor 2802 with a third electrode 2808. The analyte sensor 2802 includes a working electrode 2806, a reference electrode 2804 and the third electrode 2808. The third electrode 2808, in some examples, may include the same reference material as the reference electrode 2804. In the arrangement 2800, the working electrode 2806 and reference electrode 2804 are positioned under skin 2812 of a host. The third electrode 2808 is positioned on the skin 2812. In some examples, an electrolyte gel or other suitable electrically conductive material is positioned between the third electrode 2808 and the skin 2812.

Sensor electronics 2810 may receive signals from the various electrodes 2804, 2806, 2808. In various examples, the sensor electronics 2810 generates an electrical connection between the reference electrode 2804 and the third electrode 2808. (In some examples, the electrodes 2804, 2808 are hard wired together.) In this way, both electrodes 2808, 2804 act as reference electrodes, thus increasing the reference capacity of the analyte sensor 2802.

In another arrangement, the third electrode 2808 is used as a counter electrode. In yet another example arrangement, the sensor electronics switch the sensor 2802 between the configuration in which the electrodes 2808 and 2804 are electrically connected with both serving as reference electrodes and a three electrode arrangement in which the third electrode 2808 acts as a counter electrode. For example, the third electrode 2808 may be connected as an additional reference electrode when the capacity of the reference electrode 2804 is below a threshold level.

Figure 29:
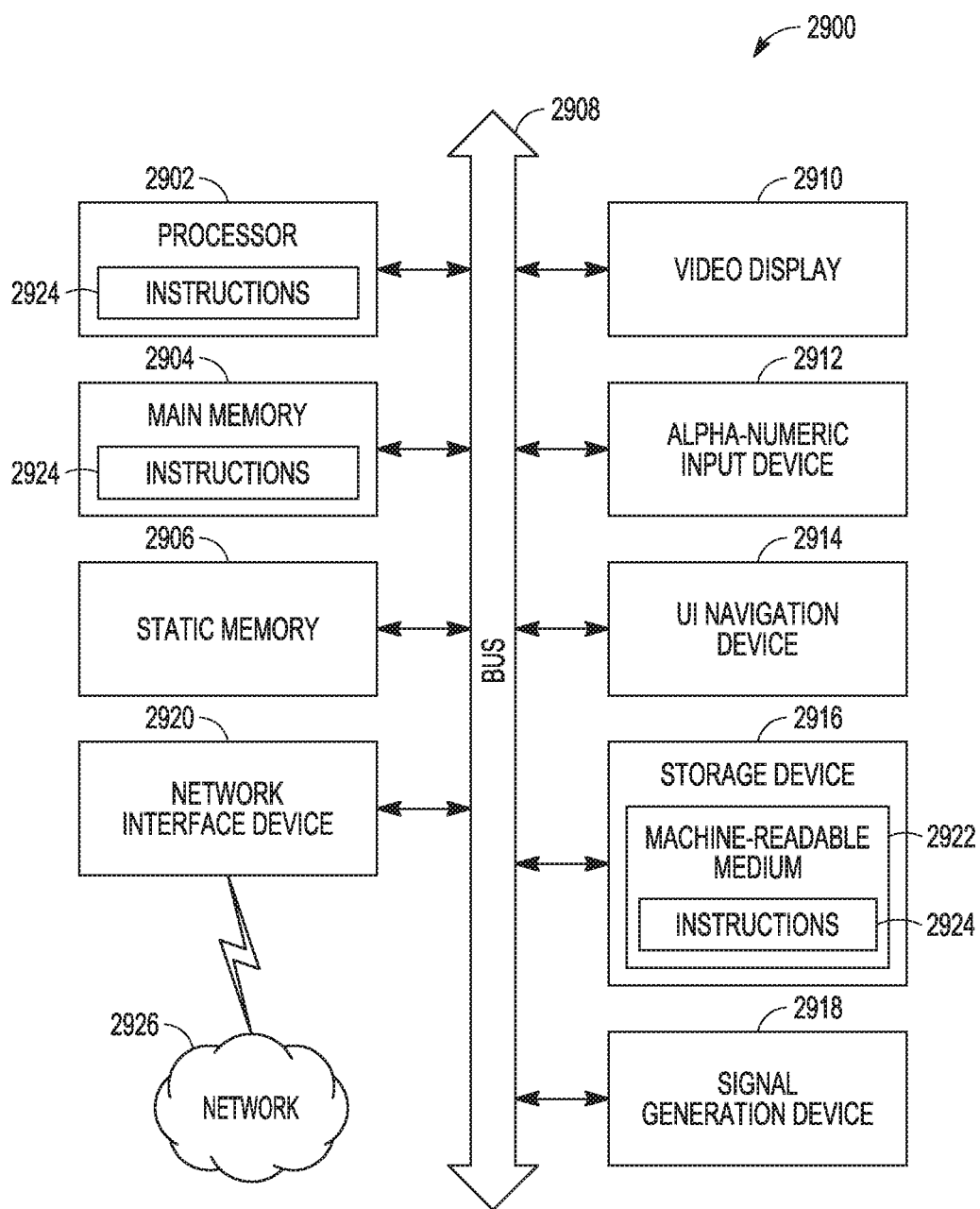
FIG. 29 is a block diagram illustrating a computing device hardware architecture, within which a set or sequence of instructions can be executed to cause a machine to perform examples of any one of the methodologies discussed herein.

FIG. 29 is a block diagram illustrating a computing device hardware architecture 2900, within which a set or sequence of instructions can be executed to cause a machine to perform examples of any one of the methodologies discussed herein. The hardware architecture 2900 can describe various computing devices including, for example, the sensor electronics 106, the peripheral medical device 122, the smart device 112, the tablet 114, etc.

The architecture 2900 may operate as a standalone device or may be connected (e.g., networked) to other machines. In a networked deployment, the architecture 2900 may operate in the capacity of either a server or a client machine in server-client network environments, or it may act as a peer machine in peer-to-peer (or distributed) network environments. The architecture 2900 can be implemented in a personal computer (PC), a tablet PC, a hybrid tablet, a set-top box (STB), a personal digital assistant (PDA), a mobile telephone, a web appliance, a network router, a network switch, a network bridge, or any machine capable of executing instructions (sequential or otherwise) that specify operations to be taken by that machine.

The example architecture 2900 includes a processor unit 2902 comprising at least one processor (e.g., a central processing unit (CPU), a graphics processing unit (GPU), or both, processor cores, compute nodes). The architecture 2900 may further comprise a main memory 2904 and a static memory 2906, which communicate with each other via a link 2908 (e.g., bus). The architecture 2900 can further include a video display unit 2910, an input device 2912 (e.g., a keyboard), and a UI navigation device 2914 (e.g., a mouse). In some examples, the video display unit 2910, input device 2912, and UI navigation device 2914 are incorporated into a touchscreen display. The architecture 2900 may additionally include a storage device 2916 (e.g., a drive unit), a signal generation device 2918 (e.g., a speaker), a network interface device 2920, and one or more sensors (not shown), such as a Global Positioning System (GPS) sensor, compass, accelerometer, or other sensor.

In some examples, the processor unit 2902 or another suitable hardware component may support a hardware interrupt. In response to a hardware interrupt, the processor unit 2902 may pause its processing and execute an ISR, for example, as described herein.

The storage device 2916 includes a machine-readable medium 2922 on which is stored one or more sets of data structures and instructions 2924 (e.g., software) embodying or used by any one or more of the methodologies or functions described herein. The instructions 2924 can also reside, completely or at least partially, within the main memory 2904, within the static memory 2906, and/or within the processor unit 2902 during execution thereof by the architecture 2900, with the main memory 2904, the static memory 2906, and the processor unit 2902 also constituting machine-readable media.

Executable Instructions and Machine-Storage Medium

The various memories (i.e., 2904, 2906, and/or memory of the processor unit(s) 2902) and/or storage device 2916 may store one or more sets of instructions and data structures (e.g., instructions) 2924 embodying or used by any one or more of the methodologies or functions described herein.

These instructions, when executed by processor unit(s) 2902 cause various operations to implement the disclosed examples.

As used herein, the terms "machine-storage medium," "device-storage medium," "computer-storage medium" (referred to collectively as "machine-storage medium 2922") mean the same thing and may be used interchangeably in this disclosure. The terms refer to a single or multiple storage devices and/or media (e.g., a centralized or distributed database, and/or associated caches and servers) that store executable instructions and/or data, as well as cloud-based storage systems or storage networks that include multiple storage apparatus or devices. The terms shall accordingly be taken to include, but not be limited to, solid-state memories, and optical and magnetic media, including memory internal or external to processors. Specific examples of machine-storage media, computer-storage media, and/or device-storage media 2922 include non-volatile memory, including by way of example semiconductor memory devices, e.g., erasable programmable read-only memory (EPROM), electrically erasable programmable read-only memory (EEPROM), FPGA, and flash memory devices; magnetic disks such as internal hard disks and removable disks; magneto-optical disks; and CD-ROM and DVD-ROM disks. The terms machine-storage media, computer-storage media, and device-storage media 2922 specifically exclude carrier waves, modulated data signals, and other such media, at least some of which are covered under the term "signal medium" discussed below.

Signal Medium

The term "signal medium" or "transmission medium" shall be taken to include any form of modulated data signal, carrier wave, and so forth. The term "modulated data signal" means a signal that has one or more of its characteristics set or changed in such a matter as to encode information in the signal.

Computer-Readable Medium

The terms "machine-readable medium," "computer-readable medium" and "device-readable medium" mean the same thing and may be used interchangeably in this disclosure. The terms are defined to include both machine-storage media and signal media. Thus, the terms include both storage devices/media and carrier waves/modulated data signals.

The instructions 2924 can further be transmitted or received over a communications network 2926 using a transmission medium via the network interface device 2920 using any one of a number of well-known transfer protocols (e.g., HTTP). Examples of communication networks include a LAN, a WAN, the Internet, mobile telephone networks, plain old telephone service (POTS) networks, and wireless data networks (e.g., Wi-Fi, 3G, 4G LTE/LTE-A, 5G or WiMAX networks). The term "transmission medium" shall be taken to include any intangible medium that is capable of storing, encoding, or carrying instructions for execution by the machine, and includes digital or analog communications signals or other intangible media to facilitate communication of such software.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Various components are described in the present disclosure as being configured in a particular way. A component may be configured in any suitable manner. For example, a component that is or that includes a computing device may be configured with suitable software instructions that program the computing device. A component may also be configured by virtue of its hardware arrangement or in any other suitable manner.

The above description is intended to be illustrative, and not restrictive. For example, the above-described examples (or one or more aspects thereof) can be used in combination with others. Other examples can be used, such as by one of ordinary skill in the art upon reviewing the above description. The Abstract is to allow the reader to quickly ascertain the nature of the technical disclosure, for example, to comply with 37 C.F.R. § 1.72(b) in the United States of America. It is submitted with the understanding that it will not be used to interpret or limit the scope or meaning of the claims.

Also, in the above Detailed Description, various features can be grouped together to streamline the disclosure. However, the claims cannot set forth every feature disclosed herein, as examples can feature a subset of said features. Further, examples can include fewer features than those disclosed in a particular example. Thus, the following claims are hereby incorporated into the Detailed Description, with each claim standing on its own as a separate example. The scope of the examples disclosed herein is to be determined with reference to the appended claims, along with the full scope of equivalents to which such claims are entitled.

Each of these non-limiting examples in any portion of the above description may stand on its own or may be combined in various permutations or combinations with one or more of the other examples.

The above detailed description includes references to the accompanying drawings, which form a part of the detailed description. The drawings show, by way of illustration, specific embodiments in which the subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," "third," etc., are used merely as labels, and are not intended to impose numerical requirements on their objects.

Geometric terms, such as "parallel", "perpendicular", "round", or "square" are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

The term "substituted" as used herein in conjunction with a molecule in which one or more hydrogen atoms contained therein are replaced by one or more non-hydrogen atoms. Examples of substituents or functional groups that can be substituted include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The polymers described herein can terminate in any suitable way. In some embodiments, the polymers can terminate with an end group that is independently chosen from a suitable polymerization initiator, —H, —OH, a substituted or unsubstituted $(C_1-C_{20})$hydrocarbyl (e.g., $(C_1-C_{10})$alkyl or $(C_6-C_{20})$aryl) interrupted with 0, 1, 2, or 3 groups independently selected from —O—, substituted or unsubstituted —NH—, and —S—, a poly(substituted or unsubstituted $(C_1-C_{20})$hydrocarbyloxy), and a poly(substituted or unsubstituted $(C_1-C_{20})$hydrocarbylamino).

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, gel permeation chromatography, and sedimentation velocity.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the subject matter should be determined with reference to the claims, along with the full scope of equivalents to which such claims are entitled.

What is claimed is:

1. A glucose sensor comprising:
    a working electrode to support an oxidation reaction; and
    a reference electrode to support a redox reaction, the reference electrode comprising:
    silver and silver chloride, wherein the silver comprises microscale silver particles having an average width of between about 1 micron and about 10 microns, and nanoscale silver particles having an average size that is less than 100 nanometers, wherein the nanoscale silver particles make up between about 0.1% and about 10% of the silver by volume; and
    an anti-mineralization agent positioned at the reference electrode to reduce formation of calcium carbonate at the reference electrode.

2. The glucose sensor of claim 1, wherein the reference electrode further comprises a mediator material to catalyze oxygen redox at the reference electrode at least in part with the silver.

3. The glucose sensor of claim 1, wherein the anti-mineralization agent is selected from the group consisting of a polyacrylate and a carboxylate-containing polymer.

4. The glucose sensor of claim 1, further comprising a membrane system comprising an anti-mineralization layer positioned at least in part over the reference electrode, the anti-mineralization layer comprising at least a portion of the anti-mineralization agent.

5. The glucose sensor of claim 4, wherein the membrane system further comprises an interference domain positioned at least in part over the working electrode, the interference domain comprising a first interference agent and at least a portion of the anti-mineralization agent.

6. The glucose sensor of claim 1, wherein the reference electrode comprises a binder material, and wherein the silver, the silver chloride, and the anti-mineralization agent are positioned within the binder material.

7. The glucose sensor of claim 1, wherein the anti-mineralization agent comprises a polyacrylate.

8. The glucose sensor of claim 1, wherein the anti-mineralization agent comprises a carboxylate-containing polymer.

9. The glucose sensor of claim 8, wherein the carboxylate-containing polymer is selected from the group consisting of a poly(maleate), a polysulfonate, and a polyphosphonate.

10. The glucose sensor of claim 1, further comprising a membrane system, the membrane system comprising:
    a resistance domain positioned at least in part over the reference electrode; and
    a hydrophilic domain positioned at least in part over the reference electrode.

11. The glucose sensor of claim 1, wherein the silver chloride comprises particles of silver chloride having a diameter of between 0.5 microns and 5 microns.

12. A method of manufacturing a glucose sensor, comprising:
dipping a distal end of the glucose sensor into a first solution to a first depth from a distal end, the glucose sensor comprising a working electrode and a reference electrode comprising silver and silver chloride, wherein the silver comprises microscale silver particles having an average width of between about 1 micron and about 10 microns, and nanoscale silver particles having an average size that is less than 100 nanometers, wherein the nanoscale silver particles make up between about 0.1% and about 10% of the silver by volume, and wherein the first solution comprises a first agent, wherein, at the first depth, the first solution is positioned to cover the working electrode; and
dipping the distal end of the glucose sensor into a second solution to a second depth from the distal end, the second solution comprising an anti-mineralization agent, wherein, at the second depth, the second solution is positioned to cover the working electrode and to cover at least a portion of the reference electrode, wherein the first agent and an anti-mineralization agent form an interference domain over the working electrode.

13. The method of claim 12, wherein the dipping of the distal end of the glucose sensor into the second solution is after the dipping of the distal end of the glucose sensor into the first solution, further comprising, after dipping the distal end of the glucose sensor into the second solution, re-dipping the distal end of the glucose sensor into the first solution to the first depth.

14. The method of claim 12, wherein the dipping of the distal end the glucose sensor into the first solution is after the dipping of the distal end of the glucose sensor into the second solution, further comprising, after dipping the distal end of the glucose sensor into the first solution, re-dipping the distal end of the glucose sensor into the second solution to the second depth.

15. The method of claim 12, further comprising dipping the distal end of the glucose sensor into a third solution comprising glucose oxidase.

16. The method of claim 12, wherein the anti-mineralization agent comprises a polyacrylate.

17. The method of claim 12, wherein the anti-mineralization agent comprises a carboxylate-containing polymer.

18. The method of claim 17, wherein the carboxylate-containing polymer is selected from the group consisting of a poly(maleate), a polysulfonate, a polyphosphonate.

19. The method of claim 12, further comprising:
applying a first current between the working electrode and the reference electrode; and
after applying the first current, generating a sensor current with the glucose sensor, a magnitude of the sensor current indicating glucose concentration at the glucose sensor, the first current being larger than the sensor current.

20. The method of claim 12, further comprising:
immersing at least the reference electrode in a solution of chlorine bleach; and
after the immersing, generating a sensor current with the glucose sensor, a magnitude of the sensor current indicating glucose concentration at the glucose sensor.

* * * * *